US008912335B2

(12) United States Patent
Colca et al.

(10) Patent No.: US 8,912,335 B2
(45) Date of Patent: Dec. 16, 2014

(54) PPAR-SPARING THIAZOLIDINEDIONE SALTS FOR THE TREATMENT OF METABOLIC DISEASES

(75) Inventors: Gerard R. Colca, Kalamazoo, MI (US); Steven P. Tanis, Carlsbad, CA (US); Scott D. Larsen, South Lyon, MI (US)

(73) Assignee: Metabolic Solutions Development Company, LLC, Kalamazoo, MI (US)

( * ) Notice: Subject to any disclaimer, the term of this patent is extended or adjusted under 35 U.S.C. 154(b) by 141 days.

(21) Appl. No.: 13/515,508

(22) PCT Filed: Dec. 15, 2010

(86) PCT No.: PCT/US2010/060439
§ 371 (c)(1),
(2), (4) Date: Aug. 20, 2012

(87) PCT Pub. No.: WO2011/084453
PCT Pub. Date: Jul. 14, 2011

(65) Prior Publication Data
US 2012/0309975 A1    Dec. 6, 2012

Related U.S. Application Data

(60) Provisional application No. 61/286,765, filed on Dec. 15, 2009.

(51) Int. Cl.
*C07D 417/12* (2006.01)
*C07D 277/34* (2006.01)

(52) U.S. Cl.
CPC ............ *C07D 417/12* (2013.01); *C07D 277/34* (2013.01)
USPC ..................................................... 546/269.7

(58) Field of Classification Search
USPC ..................................................... 546/269.7
See application file for complete search history.

(56) References Cited

U.S. PATENT DOCUMENTS

| | | | |
|---|---|---|---|
| 4,287,200 A | 9/1981 | Kawamatsu et al. |
| 4,582,839 A | 4/1986 | Meguro et al. |
| 4,687,777 A | 8/1987 | Meguro et al. |
| 4,725,610 A | 2/1988 | Meguro et al. |
| 5,304,212 A | 4/1994 | Czeisler et al. |
| 5,441,971 A | 8/1995 | Sohda et al. |
| 5,886,026 A | 3/1999 | Hunter et al. |
| 5,929,101 A | 7/1999 | Colca |
| 6,099,562 A | 8/2000 | Ding et al. |
| 6,693,106 B2 | 2/2004 | Rahbar et al. |
| 8,067,450 B2 | 11/2011 | Colca et al. |
| 2006/0083784 A1 | 4/2006 | Ignatious et al. |
| 2007/0043094 A1 | 2/2007 | Wizel et al. |
| 2007/0078170 A1 | 4/2007 | Khanduri et al. |
| 2008/0319024 A1 | 12/2008 | Greil et al. |
| 2009/0082405 A1 | 3/2009 | Czarnik |
| 2009/0137638 A1 | 5/2009 | Colca et al. |
| 2009/0143441 A1 | 6/2009 | Colca |
| 2009/0143442 A1 | 6/2009 | Colca et al. |
| 2012/0015982 A1 | 1/2012 | Colca et al. |
| 2012/0129896 A1 | 5/2012 | Colca et al. |

FOREIGN PATENT DOCUMENTS

| | | |
|---|---|---|
| EP | 0008203 | 2/1980 |
| EP | 0155845 | 9/1985 |
| EP | 0193256 | 9/1986 |
| EP | 0441605 | 8/1991 |
| EP | 0549365 | 6/1993 |
| EP | 0753298 | 1/1997 |
| JP | 2005 247740 | 9/2005 |
| WO | 85/04170 | 9/1985 |
| WO | 86/02073 | 4/1986 |
| WO | 92/18501 | 10/1992 |
| WO | 01/00579 | 1/2001 |
| WO | 01/00689 | 1/2001 |
| WO | 01/82916 | 11/2001 |
| WO | 02/088120 | 11/2002 |
| WO | 02/043807 | 8/2003 |
| WO | 2004/007490 | 1/2004 |
| WO | 2004/033438 | 4/2004 |
| WO | 2004/101561 | 11/2004 |
| WO | 2006/035954 | 4/2006 |
| WO | 2007/109024 | 9/2007 |
| WO | 2009/038681 | 3/2009 |
| WO | 2010/015818 | 2/2010 |
| WO | 2010/105048 | 9/2010 |
| WO | 2011/017244 | 2/2011 |
| WO | 2011/075514 | 6/2011 |
| WO | 2011/084456 | 7/2011 |
| WO | 2011/084459 | 7/2011 |
| WO | 2011/133611 | 10/2011 |

OTHER PUBLICATIONS

Agarwal, Rajiv, "Anti-Inflammatory Effects of Short-Term Pioglitazone Therapy in Men with Advanced Diabetic Nephropathy", American Journal of Physiology—Renal Physiology, vol. 290, No. 3 (2006). pp. F600-F605.

Bailey, Clifford J., et al., "Thiazolidinediones today", The British Journal of Diabetes and Vascular Disease, vol. 1, No. 1, Aug. 2001, pp. 7-13.

Bastin, R J, et al., "Salt Selection and Optimisation for Pharmaceutical New Chemical Entities", Organic Process Research and development, Cambridge GB, vol. 4, No. 5, Jan. 1, 2000, pp. 427-435.

Ben-Bassat, Avraham A., et al., "Quaternary Pilocarpine Derivatives as Potential Acetylcholine Antagonist. 2. Alterations in the Lactone and Imidazole Moieties", Journal of Medicinal Chemistry, vol. 19, No. 7, 1976, pp. 928-933.

Berge, S.M., "Pharmaceutical Salts", Journal Pharmaceutical Sciences, vol. 66, No. 1 (1977), pp. 1-19.

(Continued)

Primary Examiner — Patricia L Morris
(74) Attorney, Agent, or Firm — Honigman Miller Schwartz & Cohn LLP; Andrew N. Weber; Jonathan P. O'Brien

(57) ABSTRACT

The present invention relates to novel salts of thiazolidinediones and other pharmaceutical agents that are useful for treating and/or preventing metabolic diseases (e.g., diabetes, or neurodegenerative diseases (e.g., Alzheimer's Disease).

1 Claim, 14 Drawing Sheets

(56) References Cited

OTHER PUBLICATIONS

Berger, Joel, et al., "Thiazolidinediones Produce a Conformational Change in Peroxisomal Proliferator-Activated Receptor-y: Binding and Activation Correlate with Antidiabetic Actions in db/db Mice", Endocrinology, vol. 137, No. 10, 1996, pp. 4189-41995.

Blocker, <http://dictionary.reference.com/browse/blocker>, accessed Apr. 6, 2011, Office Action Summary dated Apr. 13, 2011 for U.S. Appl. No. 12/677,541.

Bogacka, Iwona, et al., "The Effect of Pioglitazone on Peroxisome Proliferator-Activated Receptor-y Target Genes Related to Lipid Storage In Vivo", Diabetes Care, vol. 27, No. 7, Jul. 2004, pp. 1660-1667.

Bolten, Charles W., et al., "Insulin sensitizing pharmacology of thiazolidinediones correlates with mitochondrial gene expression rather than activation of PPAR gamma", Gene Regulation and Systems Biology 2007, Lnkd-Pubmed: 19936080, vol. 1, 2001, pp. 73-82, XP002633659, ISSN: 1177-6250.

Bower, Vicki, "Like a snake in the grass: As the incidence of type 2 diabetes escalates, new developments offer hope for better treatments", European Molecular Biology Organization, EMBO Reports, vol. 5, No. 6, 2004, pp. 555-558.

Campbell, I. W., "Pioglitazone—An Oral Antidiabetic Agent and Metabolic Syndrome Modulator, Can Theory Translate into Practice?", British Journal of Diabetes and Vascular Disease, Medinews, GB vol. 5, No. 4 (2005), pp. 209-216.

Carpenter, Donald, E., et al., "Process Development and Scale-Up of the Potential Thiazolidinedione Antidiabetic Candidate PNU-91325", Organic Process Research and Development, American Chemical Society, (2002), vol. 6, pp. 721-728.

Chawla, Ajay, et al., "Peroxisome Proliferator-Activated Receptor (PPAR) y: Adipose-Predominant Expression and Induction Early in Adipocyte Differentiation", Endocrinology, vol. 135, No. 2, 1994, pp. 798-800.

Chawla, Ajay, et al., "PPAR-y dependent and independent effects on macrophage-gene expression in lipid metabolism and inflammation", Nature Publishing Group, Nature Medicine, vol. 7, No. 1, Jan. 2001, pp. 48-52.

Colca, J. R., et al., "What has Prevented the Expansion of Insulin Sensitisers?", Expert Opinion on Investigational Drugs, 2006, United Kingdom, vol. 15, No. 3 (2006), pp. 205-210.

Colca, Jerry R., "Insulin sensitizers may prevent metabolic inflammation", Biochemical Pharmacology, Pergamon, Oxford, GB, vol. 72, No. 2, Jul. 14, 2006, pp. 125-131, XP025043395, ISSN: 0006-2952.

Colca, Jerry R., et al., "Identification of a Novel Mitochondrial Protein ("mitoNEET") cross-linked specifically by a thiazolidinedione photoprobe", American Journal of Physiology, Endocrinology and Metabolism, Feb. 2004, vol. 286, No. 2, pp. E252-E260, XP002997343, ISSN: 0193-1849.

Coussens, Lisa M., et al., "Inflammatory Cells and Cancer: Think Different!", J. Experimental Medicine, 2001, The Rockefeller University Press, vol. 196, No. 6, pp. F23-F26.

Diuretic, <http://www.medterms.com/script/main/art.asp?articlekey=7103>, accessed Apr. 6, 2011, Office Action Summary dated Apr. 13, 2011 for U.S. Appl. No. 12/677,541.

Einhorn, MD, Daniel, et al. "Pioglitazone Hydrochloride in Combination With Metformin in the Treatment of Type 2 Diabetes Mellitus: A Randomized, Placebo-Controlled Study", Clinical Therapeutics, vol. 22, No. 12, 2000, pp. 1398-1409.

Feinstein, D.L., "Receptor-independent actions of PPAR thiazolidinedione agonists: Is mitochondrial function the key?" Biochemical Pharmacology, Pergamon, Oxford, GB, vol. 70, No. 2, Jul. 15, 2005, pp. 177-188.

Freireich, D.L., "Quantative Comparisons of Toxicity of Anticancer Agents in Mouse, Rate, Hamster, Dog, Monkey and Man", Cancer Chemotherapy Reports, vol. 50, No. 4 (1966), p. 219-244.

Geldmacher, D.S., "Pioglitazone in Alzheimer's Disease: Rationale and Clinical Trial Design", Neurobiology of Aging, Tarrytown, NY, US, vol. 25 (2004), pp. S211-S212.

Gerber, Pietro, et al., "Effects of Pioglitazone on Metabolic Control and Blood Pressure: A Randomized Study in Patients with Type 2 Diabetes Mellitus", Current Medical Research and Opinion, Hants, GB, vol. 19, No. 6 (2003), pp. 532-539.

Harrigan, George G., et al., "PNU-91325 Increases Fatty Acid Syntheses from Glucose and Mitochondrial Long Chain Fatty Acid Degradation: A Comparative Tracer-Based Metabolomics Study with Rosiglitazone and Pioglitazone in hepG2 Cells", Metabolomics, Kluwer Academic Publishers—Plenum Publishers, NE, vol. 2, No. 1 (2006) pp. 21-29.

Heneka, Michael T., et al., "Acute treatment with the PPARy agonist pioglitazone and ibuprofen reduces glial inflammation and AB1-42 levels in APPV717I transgenic mice", Brain, vol. 128, 2005, pp. 1442-1453.

Hofmann, C., "Glucose Transport Deficiency Corrected by Treatment with the Oral Anti-Hyperglycemic Agent Pioglitazone", Endocrinology, 129 (1991), pp. 1915-1925.

Inhibitor, <http://www.biology-online.org/dictionary/Inhibitor>, accessed Apr. 6, 2011, Office Action Summary dated Apr. 13, 2011 for U.S. Appl. No. 12/677,541.

International Search Report for PCT/US2007/006321 dated Sep. 3, 2007.

International Search Report for PCT/US2007/006385 dated Sep. 10, 2007.

International Search Report for PCT/US2007/006508 dated Sep. 7, 2007.

International Search Report for PCT/US2008/010723 dated Mar. 2, 2009.

International Search Report for PCT/US2010/026971 dated Jul. 22, 2010.

International Search Report for PCT/US2010/044066 dated Sep. 16, 2010.

International Search Report for PCT/US2010/060439 dated May 23, 2011.

International Search Report for PCT/US2010/060449 dated Mar. 7, 2011.

International Search Report for PCT/US2010/060453 dated Mar. 28, 2011.

International Search Report for PCT/US2010/060459 dated Mar. 2, 2011.

International Search Report for PCT/US2011/033145 dated Jul. 22, 2011.

Kahn, Barbara B., et al., "Rosiglitazone, PPARy, and Type 2 Diabetes", The New England Journal of Medicine, vol. 363, No. 27, Dec. 30, 2010 pp. 2667-2669.

Kulkarni, Santosh S., et al., "Three-Dimensional Quantitative Structure Activity Relationship (3-D-QSAR) of Antihyperglycemic Agents" Bioorganic & Medicinal Chemistry, Elsevier Science Ltd, GB, vol. 7 (1999), pp. 1475-1485.

Lan, Hong, et al., "GPR119 is required for physiological regulation of glucagon-like peptide-1 secretion but not for metabolic homeostasis", Journal of Endocrinology, vol. 201, 2009, pp. 219-230.

Leff, Todd, et al., "The Antidiabetic PPARy Ligands: An Update on Compounds in Development", Current Medicinal Chemistry: Immunology, Endocrine & Metabolic Agents, vol. 2, No. 1, 2002, pp. 33-47.

Lehmann, J.M., "An Antidiabetic Thiazolidinedione is a High Affinity Ligand for Peroxisome Proliferator-activated Receptor y (PPARy)", The Journal of Biological Chemistry, vol. 270, No. 22, 1995, pp. 12953-12956.

Maorong, Jiang, et al., "The molecular characterization of the brain protein 44-like (Brp441) gene of Gekko japonicus and its expression changes in spinal cord after tail amputation", Molecular Biology Reports, An International Journal of Molecular and Cellular Biology, Kluwer Academic Publishers, DO, vol. 36, No. 2, Nov. 18, 2007, pp. 215-220, XP019647202, ISSN: 1573-4978.

Matsusue, K., "Liver Specific Disruption of PPAR in Leptin-Deficient Mice Improves Fatty Liver but Aggravates Diabetic Phenotypes", J. Clim. Invest., 111 (2003), p. 737.

(56) References Cited

OTHER PUBLICATIONS

Meirhaeghe, Aline, et al., "Association Between Peroxisome Proliferator-Activated Receptor y Haplotypes and the Metabolic Syndrome in French Men and Women", Diabetes, vol. 54, Oct. 2005, pp. 3043-3048.

Miles, Phillip D. G., "Effect of heterozygous PPARy deficiency and TZD treatment on insulin resistance associated with age and high-fat feeding", American Journal of Physiology, Endocrinology and Metabolism, vol. 284, Mar. 2003, pp. E618-E626.

Misra, Parimal, et al., "PAT5A: A Partial Agonist of Peroxisome Proliferator-Activated Receptor y Is a Potent Antidabetic Thiazolidinedione Yet Weakly Adipogenic", The Journal of Pharmacology and experimental Therapeutics, vol. 306, No. 2, 2003, pp. 763-771.

Oakley, Holley, et al., "Intraneuronal β-Amyloid Aggregates, Nuerodegeneration, and Neuron Loss in Transgenic Mice with Five Familial Alzheimer's Disease Mutations: Potential Factors in Amyloid Plaque Formation", The Journal of Neuroscience, vol. 26, No. 40, Oct. 4, 2006, pp. 10129-10140.

Oguchi, M., et al., "Molecular Design, Synthesis, and hypoglycemic Activity of a Series of Thiazolidine-2, 4-diones", Journal of Medicinal Chemistry, (2000)vol. 43 No. 16, pp. 3052-3066.

Olefsky, Jerrold M., et al., "PPARy and the Treatment of Insulin Resistance", TEM, Elsevier Science Ltd., vol. 11, No. 9, 2000, pp. 362-368.

Owens, David R., "Thiazolidinediones: A Pharmacological Overview", Clinical Drug Investigation, vol. 22, No. 8, 2002, pp. 485-505.

Pershadsingh, H., "Effect of Pioglitazone Treatment in a patient with Secondary Multiple Sclerosis", Journal of Neuorinflammation Biomed Central Ltd, London, GB, vol. 1, No. 1 (2004), p. 3.

Pershadsingh, H., "Peroxisome Proliferator-Activated Receptor-Gamma: Therapeutic Target for Diseases Beyond Diabetes: Quo Vadis?" Expert Opinion on Investigational Drugs, vol. 13, No. 3 (2004), pp. 215-228.

Pioglitazone, http://www.medicinenet.com/scriptimain/art.asp?articlekey=11577, retrieved Mar. 13, 2012, Office Action Summary dated Mar. 22, 2012 for U.S. Appl. No. 13/279,657.

Pirat, Celine, et al. "Targeting Peroxisome Proliferator-Activated Receptors (PPARs): Development of Modulators", Journal of Medicinal Chemistry, Perspective, Oct. 19, 2010, p. A-AI.

Proposal for the Process Development and Non-GMP Production of a 1 Kg Lot of 2-bromo-1-[5-ethylpyridin-2-yl] ethanone hydrobromide [BEPE] dated Sep. 28, 2011.

Proposal for the Process development and Scale up of 2-bromo-1-[5-ethylpyridin-2-yl]ethanone hydrobromide dated Sep. 26, 2011.

Reginato, Mauricio J., et al., "A Potent Antidiabetic Thiazolidinedione with Unique Peroxisome Proliferator-activated Receptor y-activating Properties", The Journal of Biological Chemistry, vol. 273, No. 49, Dec. 1998, pp. 32679-32684.

Risner, Me, et al., "Efficacy of rosiglitazone in a genetically defined population with mild-to-moderate Alzheimer's disease", The Pharmacogenomics Journal, Nature Publishing Group, vol. 6, 2006, pp. 246-254.

Sapadin, Allen N., et al., "Treatment of Scleroderma", Archives of Dermatology, American Medical Association, Jan. 2002, vol. 138, pp. 99-105.

Savage, David B., et al., "Human Metabolic Syndrome Resulting From Dominant-Negative Mutations in the Nuclear Receptor Peroxisome Proliferator-Activated Receptor-y", Diabetes vol. 52, 2003, pp. 910-917.

Schubert, Markus, et al., "Role for neuronal insulin resistance in neurodegenerative diseases", Proc Natl Acad Sci USA, vol. 101, No. 9, Mar. 2, 2004, pp. 3100-3105.

Sohda, T., "Studies on Antidiabetic Agents. Synthesis and Hypoglycemic Activity of 5-[4-(Pyridylalkoxy)Benzy1]-2,4-Thiazolidinediones", Arzneimittel Forshung Drug Research, ECV Editio. Cantor Verlag, Aulendoef, DE, vol. 40, No. 1 (1990), pp. 37-42.

Sohda, T., et al., "Studies on Antidiabetic Agents. II. Synthesis of 5-[4-(1-Methylcyclohexylmethoxy)-benzyl] thiazolidine-2,4-dione (ADD-3878) and Its Derivatives", Chemical and Pharmaceutical Bulletin, Pharmaceutical Society of Japan, Tokyo, (1982) vol. 30, No. 10, pp. 3580-3600.

Song, M. K., et al., "Exploring the Meaning of Chronic Rejection After Lung Transplantation and Its Impact on Clinical Management and Caregiving", J. Pain Symptom Management, Jun. 10, 2010, vol. 39 (abstract).

Sorensen, Henrik Toft, et al., "Skin Cancers and Non-Hodgkin Lymphoma Among Users of Systemic Glucocorticoids: A Population-Based Cohort Study", Journal of the National Cancer Institute, Oxford University Press, May 5, 2004, vol. 96, No. 9, pp. 709-711.

Spiegelman, B. M., et al., "PPAR-y: Adipogenic Regulator and Thiazolidinedione Receptor", Diabetes, vol. 47, Apr. 1998, pp. 507-514.

Statin, <http://www.amswers.com/topic/statin>, accessed Apr. 6, 2011, Office Action Summary dated Apr. 13, 2011 for U.S. Appl. No. 12/677,541.

Tanis, Steven P., et al., "Synthesis and Biological Activity of Metabolites of the Antidiabetic, Antihyperglycemic Agent Pioglitazone", Journal of Medicinal Chemistry, American Chemical Society, US, vol. 39, No. 26, 1996, pp. 5053-5063.

Tuppo, Ehab E., et al., "The role of inflammation in Alzheimer's Disease", The International Journal of Biochemistry & Cell Biology, 2005, Elsevier, vol. 37, pp. 289-305.

Vosper, H., "The Peroxisome Proliferators Activated Receptor D is Required for the Differentiation of THP-1 Monocytic Cells by Phorbol Ester", Nuclear Receptor, I (2003), p. 9.

Willi, S.M., "Effective Use of Thiazolidinedione for the Treatment of Glucocorticoid-Induced Diabetes", Diabetes Research and Clinical Practice, vol. 58, No. 2 (2002), pp. 87-96 & pp. 91-94.

Wilson, Timothy M., et al., "The Structure-Activity Relationship between Peroxisome Proliferator-Activated Receptor y Agonism and the Antihyperglycemic Activity of Thiazolidinediones", Journal of Medicinal Chemistry, vol. 39, No. 3, 1996, pp. 665-668.

Yamamoto, Shigeki, et al., "Effects of Pioglitazone on Steroid-Induced Diabetes Mellitus", Journal of the Japan Diabetes Society, vol. 47, No. 8, Aug. 2004, pp. 643-648.

Kumar, L, et al., "Salt Selection in Drug Development", Pharmaceutical Technology. vol. 3, No. 32, Mar. 2, 2008.

Stahl, P.H., et al., editors, Handbook of Pharmaceutical Salts: Properties, Selection and Use, Weinheim/Zurich: Wiley-VCH/VCHA. Apr. 2011: revised second edition.

Wouters, J., e al., editors, Pharmaceutical salts and Co-crystals, RSC Publishing. 2011, p. 139.

Moisture Sorption Analysis of Compound B Sodium Salt

| | |
|---|---|
| Experiment | Temp-RH |
| Notes | Range 5% to 95%<br>25°C at 10% increments |
| Drying | OFF |
| Max Equil Time | 180 min |
| Equil Crit | 0.0100 wt % in 5.00 min |
| T-RH Steps | 25,5;2515;25,25;25,35;25,45;25,55;25,65;<br>25,75;25,85;25,95;25,85;25,75;25,65;25,55;<br>25,45;25,35;25,25;25,15;25,5 |
| Data Logging Interval | 2.00 min or 0.0100 wt% |
| Expt Started | 1/29/2010 |
| Run Started | 9:54:19 |

PPAR-SPARING THIAZOLIDINEDIONE SALTS FOR THE TREATMENT OF METABOLIC DISEASES

CROSS-REFERENCE TO RELATED APPLICATION

This U.S. patent application claims the benefit of PCT application no. PCT/US2010/060,439 filed on Dec. 15, 2010, wich claims priority to U.S. Application Ser. No. 61/286,765 ,filed on Dec. 15, 2009.The contents of the aforementioned applications are incorporated herein by reference in its entireties.

TECHNICAL FIELD OF THE INVENTION

The present invention provides a novel salt of thiazolidinediones wherein the salt is useful for treating and/or preventing metabolic disease states (e.g., diabetes, obesity, and neurodegenerative disorders (e.g., Alzheimer's Disease)).

BACKGROUND OF THE INVENTION

Over the past several decades, scientists have postulated that PPARγ is the generally accepted site of action for insulin sensitizing thiazolidinedione compounds.

Peroxisome Proliferator Activated Receptors (PPARs) are members of the nuclear hormone receptor super family, which are ligand-activated transcription factors regulating gene expression. PPARs have been implicated in autoimmune diseases and other diseases, i.e. diabetes mellitus, cardiovascular and gastrointestinal disease, and Alzheimer's disease.

PPARγ is a key regulator of adipocyte differentiation and lipid metabolism. PPARγ is also found in other cell types including fibroblasts, myocytes, breast cells, human bone-marrow precursors, and macrophages/monocytes. In addition, PPARγ has been shown in macrophage foam cells in atherosclerotic plaques.

Thiazolidinediones, developed originally for the treatment of type-2 diabetes, generally exhibit high-affinity as PPARγ ligands. The finding that thiazolidinediones might mediate their therapeutic effects through direct interactions with PPARγ helped to establish the concept that PPARγ is a key regulator of glucose and lipid homeostasis. However, compounds that involve the activation of PPARγ also trigger sodium reabsorption and other unpleasant side effects.

SUMMARY OF THE INVENTION

The present invention provides a salt of a thiazolidinedione. Compounds of Formula I have reduced binding and activation of the nuclear transcription factor PPARγ, as do their respective salts. The salts of compounds of this invention have reduced binding or activation of the nuclear transcription factor PPARγ, do not augment sodium re-absorption, and are useful in treating or preventing obesity, diabetes, neurodegenerative diseases, and other metabolic diseases. Advantageously, the compounds having lower PPARγ activity exhibit fewer side effects than compounds having higher levels of PPARγ activity. Most specifically, by lacking PPARγ binding and activation activity, these compound salts are particularly useful for treating and/or preventing obesity or diabetes both as a single therapeutic agent or in combination with other agents that affect cellular cyclic nucleotide levels including phosphodiesterase inhibitors, adrenergic agonists, or various hormones. Moreover salts of the present invention are amenable to further processing to generate co-crystals of compound salts having Formula I.

Moreover, in some instances, the compound salts possess improved biological and physical properties over their free acid counterparts. For example, some compound salts demonstrate improved bioavailability over their free acid counterparts. Other salts possess a single polymorph, whereas the free acid compound has several polymorphs.

In one aspect, the present invention provides a hydrogen chloride (HCl) salt of a compound of Formula I:

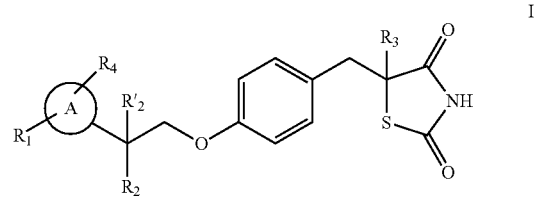

wherein each of $R_1$ and $R_4$ is independently selected from H, halo, aliphatic, and alkoxy, wherein the aliphatic or alkoxy is optionally substituted with 1-3 of halo; $R'_2$ is H and $R_2$ is H, halo, hydroxy, or optionally substituted aliphatic, —O-acyl, —O-aroyl, —O-heteroaroyl, —O(SO$_2$)NH$_2$, —O—CH($R_m$)OC(O)$R_n$, —O—CH($R_m$)OP(O)(O$R_n$)$_2$, —O—P(O)(O$R_n$)$_2$, or

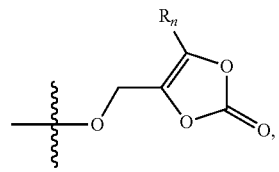

wherein each $R_m$ is independently $C_{1-6}$ alkyl, each $R_n$ is independently $C_{1-12}$ alkyl, $C_{3-8}$ cycloalkyl, or phenyl, each of which is optionally substituted; or $R_2$ and $R'_2$ together may form oxo; $R_3$ is H or $C_{1-3}$ alkyl; and ring A is phenyl, pyridin-2-yl, pyridin-3-yl or pyridin-4-yl, each of which is substituted with an $R_1$ group and an $R_4$ group at any chemically feasible position on ring A.

Another aspect of the present invention provides a dihydrogen sulfate (H$_2$SO$_4$) salt of a compound of Formula I:

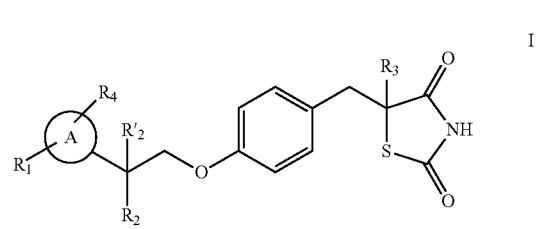

wherein each of $R_1$ and $R_4$ is independently selected from H, halo, aliphatic, and alkoxy, wherein the aliphatic or alkoxy is optionally substituted with 1-3 of halo; $R'_2$ is H and $R_2$ is H, halo, hydroxy, or optionally substituted aliphatic, —O-acyl, —O-aroyl, —O-heteroaroyl, —O(SO$_2$)NH$_2$, —O—CH($R_m$)OC(O)$R_n$, —O—CH($R_m$)OP(O)O$R_n$)$_2$, —O—P(O)(O$R_n$)$_2$, or

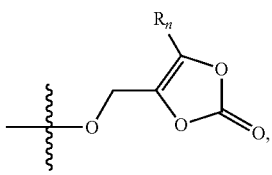

wherein each $R_m$ is independently $C_{1-6}$ alkyl, each $R_n$ is independently $C_{1-12}$ alkyl, $C_{3-8}$ cycloalkyl, or phenyl, each of which is optionally substituted; or $R_2$ and $R'_2$ together may form oxo; $R_3$ is H or $C_{1-3}$ alkyl; and ring A is phenyl, pyridin-2-yl, pyridin-3-yl or pyridin-4-yl, each of which is substituted with an $R_1$ group and an $R_4$ group at any chemically feasible position on ring A.

In some embodiments, $R_3$ is H.

In some embodiments, $R_3$ is $CH_3$.

In some embodiments, $R_4$ is H, methyl, methoxy, ethoxy, —O-isopropyl, —$CF_3$, —$OCHF_2$ or —$OCF_3$.

In some embodiments, $R_4$ is H.

In some embodiments, $R_1$ is H, alkyl, halo or alkoxy.

In some embodiments, $R_1$ is H.

In some embodiments, $R_1$ is halo.

In some embodiments, $R_1$ is $C_{1-3}$ alkyl.

In some embodiments, ring A is phenyl that is substituted with $R_1$ and $R_4$ groups at any chemically feasible position on ring A. In some examples, ring A is phenyl, and one of $R_1$ or $R_4$ is attached to the para or meta position of ring A. In other examples, ring A is phenyl, and one of $R_1$ or $R_4$ is attached to the meta position of ring A. In some examples, $R_1$ is attached to the para or meta position of ring A. And, in some examples, $R_1$ is F or Cl, either of which is attached to the para or meta position of ring A. In other examples, $R_1$ is alkoxy (e.g., methoxy, ethoxy, propoxy, —O-isopropyl, butoxy, or —O-tertbutyl) that is attached to the para or meta position of ring A. In other examples, ring A is phenyl, and $R_1$ is attached to the meta or ortho position of the phenyl ring. For instance, ring A is phenyl, and $R_1$ is attached to the ortho position of the phenyl ring. In some instances, ring A is phenyl, and $R_1$ is methoxy, ethoxy, or —O-isopropyl, any of which is attached to the ortho position of ring A. In other instances, $R_1$ is —$CF_3$, —$OCHF_2$ or —$OCF_3$.

In some embodiments, ring A is optionally substituted pyridin-2-yl or optionally substituted pyridin-3-yl, either of which is substituted with $R_1$ and $R_4$ groups at any chemically feasible position on ring A. In some examples, ring A is pyridin-2-yl, and one of $R_1$ or $R_4$ is attached to the 5 position of the ring. In other examples, ring A is pyridin-3-yl, and one of $R_1$ or $R_4$ is attached to the 6 position of the ring. In some examples, ring A is pyridin-2-yl, and $R_1$ is attached to the 5 position of the ring. For instance, ring A is pyridin-2-yl, and $R_1$ is alkyl or alkoxy, either of which is attached to the 5 position of ring A. In other instances, ring A is pyridin-2-yl, and $R_1$ is methyl, ethyl, propyl, isopropyl, butyl, or tertbutyl, any of which are attached to the 5 position of ring A.

In some embodiments, $R'_2$ is H.

In some embodiments, $R_2$ is hydroxy.

In some embodiments, $R_2$ is —O-acyl, —O-aroyl, or —O-heteroaroyl.

In some embodiments, $R_2$ and $R'_2$ together form oxo.

In some embodiments, the compound of Formula I is one selected from:

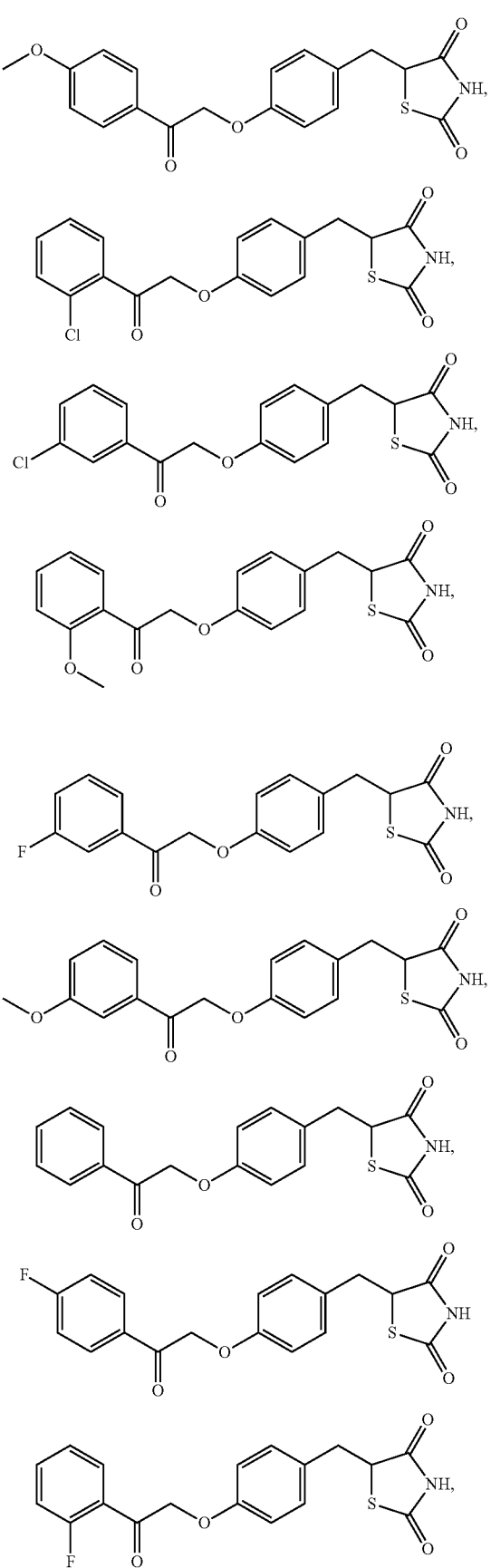

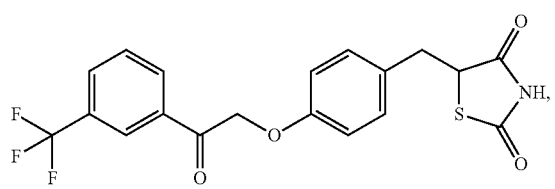
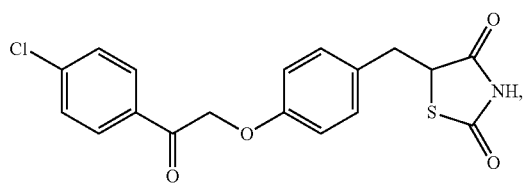 [SMILES: O=C1NC(=O)C(Cc2ccc(OCC(=O)c3ccc(Cl)cc3)cc2)S1]
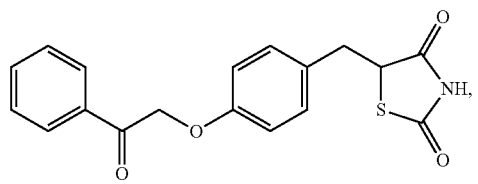 [SMILES: O=C1NC(=O)C(Cc2ccc(OCC(=O)c3ccccc3)cc2)S1]
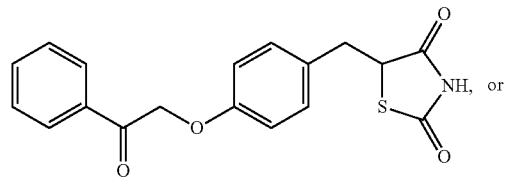 or
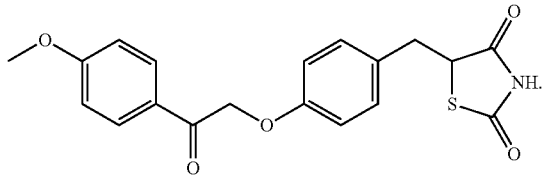 [SMILES: COc1ccc(C(=O)COc2ccc(CC3SC(=O)NC3=O)cc2)cc1]
In some embodiments, the compound of Formula I is one selected from:
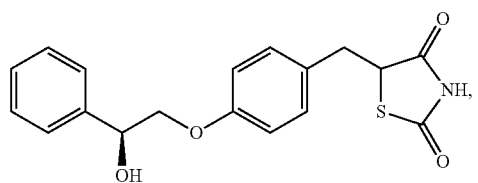 [SMILES: O=C1NC(=O)C(Cc2ccc(OC[C@@H](O)c3ccccc3)cc2)S1]
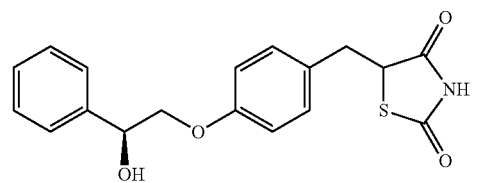
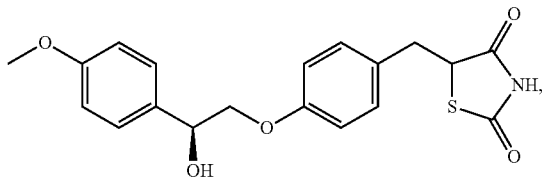
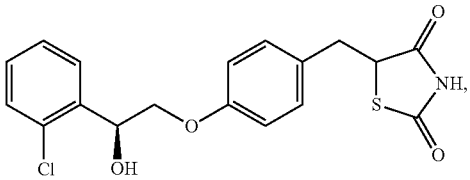 [SMILES: O=C1NC(=O)C(Cc2ccc(OC[C@@H](O)c3ccccc3Cl)cc2)S1]
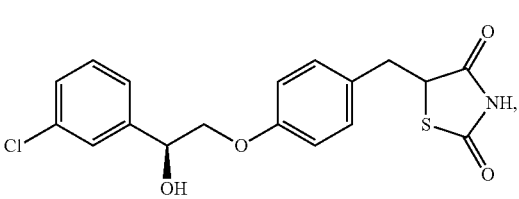
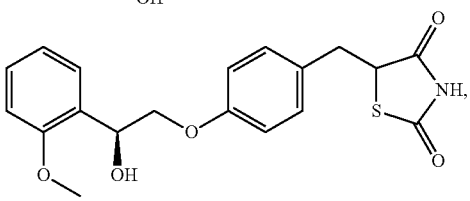
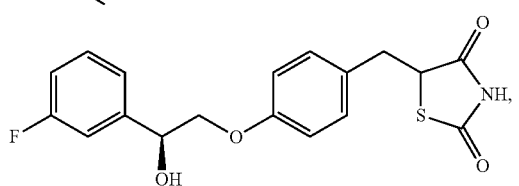
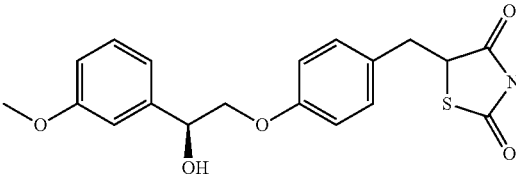
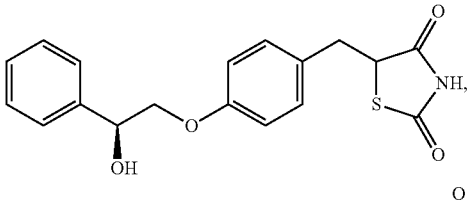

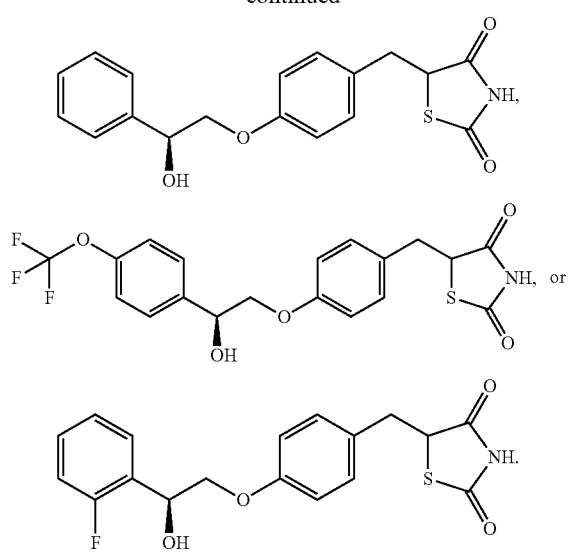
In some embodiments, the compound of Formula I is one selected from:
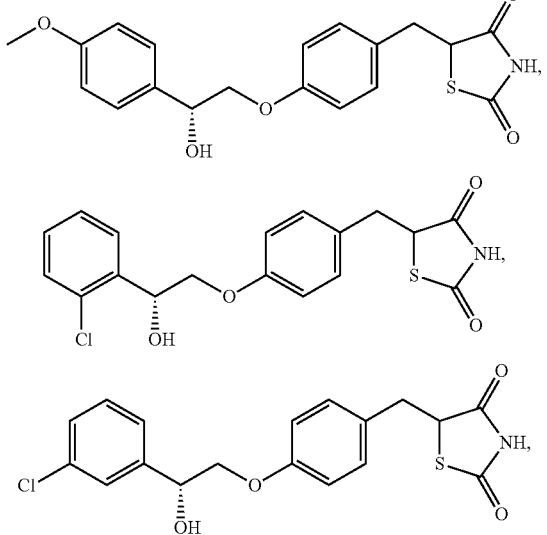
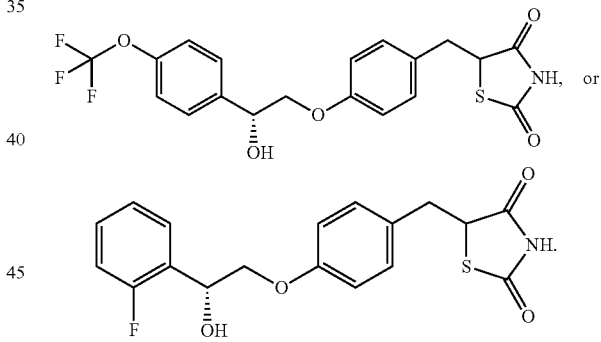
In some embodiments, the compound of Formula I is one selected from:
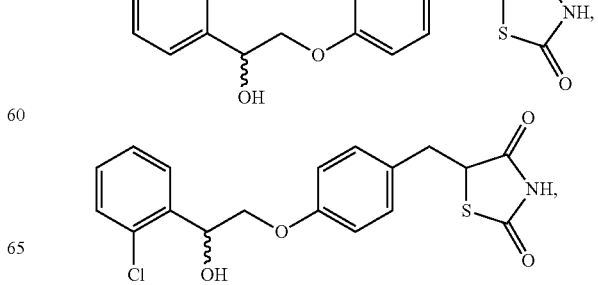

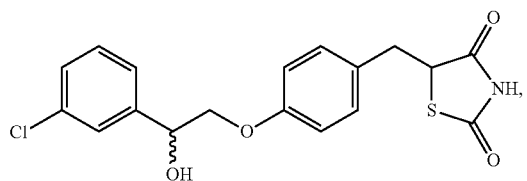 [SMILES: O=C1NC(=O)C(Cc2ccc(OCC(O)c3cccc(Cl)c3)cc2)S1]
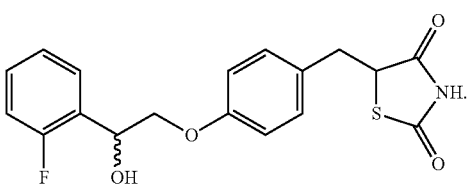
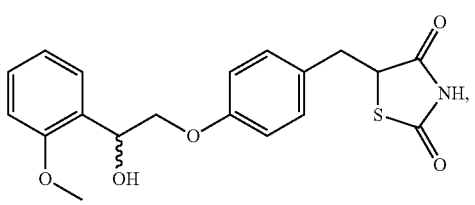 [SMILES: COc1ccccc1C(O)COc1ccc(CC2SC(=O)NC2=O)cc1]
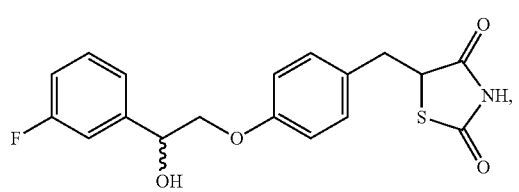 [SMILES: O=C1NC(=O)C(Cc2ccc(OCC(O)c3cccc(F)c3)cc2)S1]
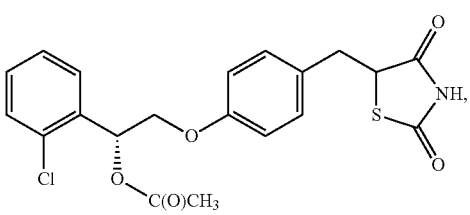
In some embodiments, the compound of Formula I is one selected from:
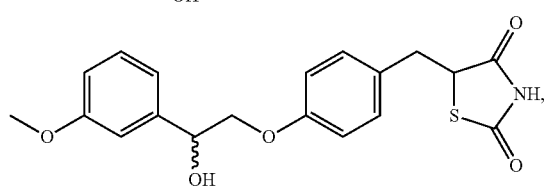
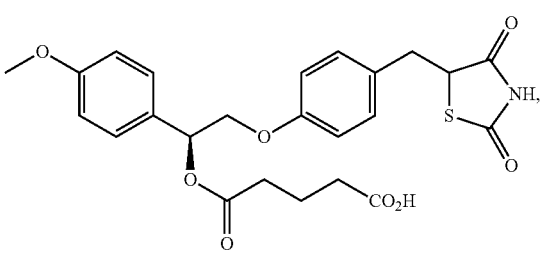
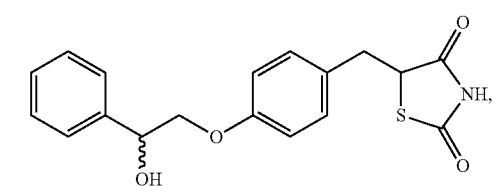
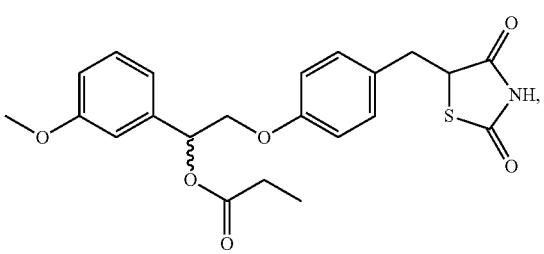
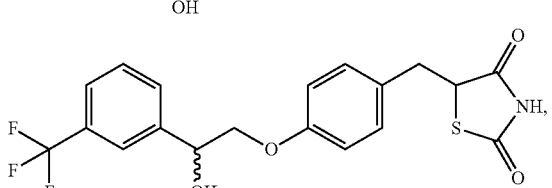
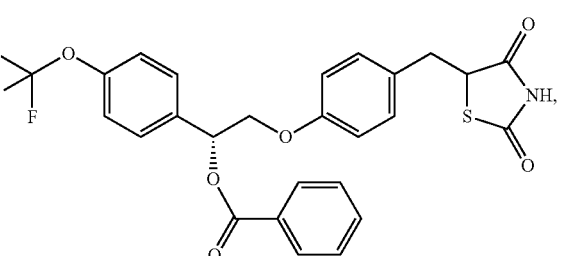
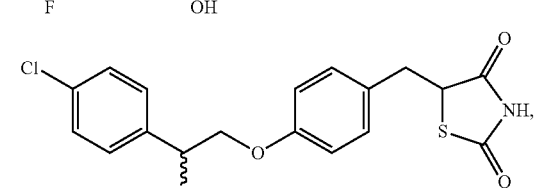
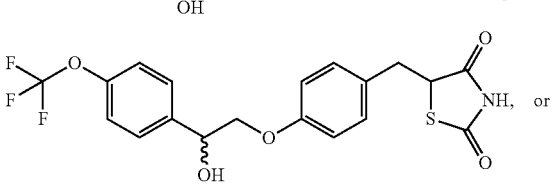
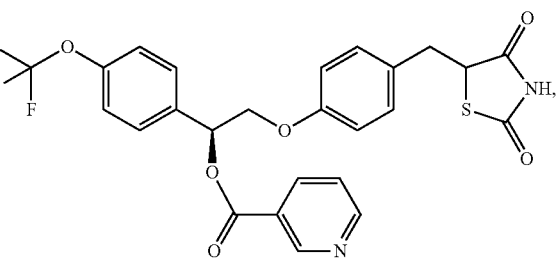

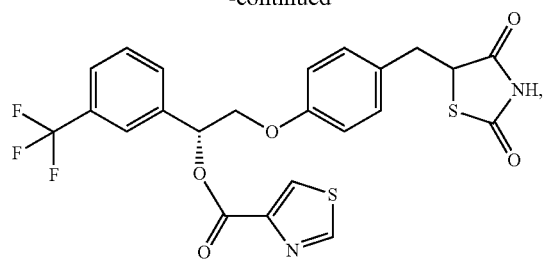
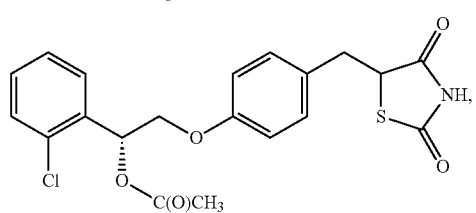
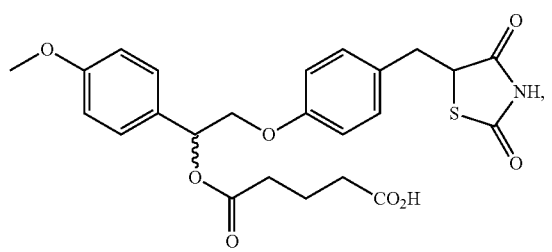
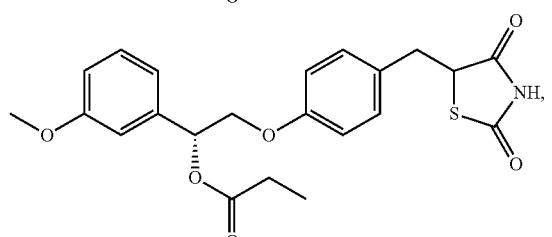
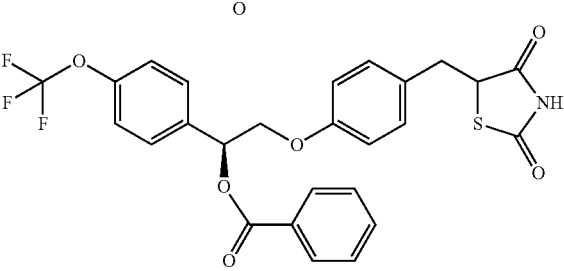
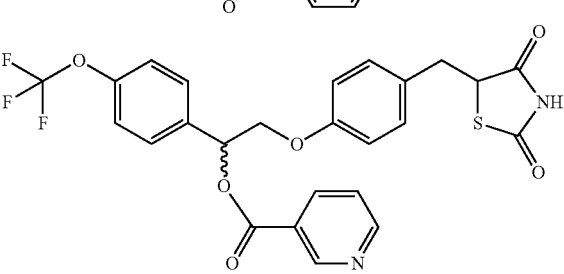
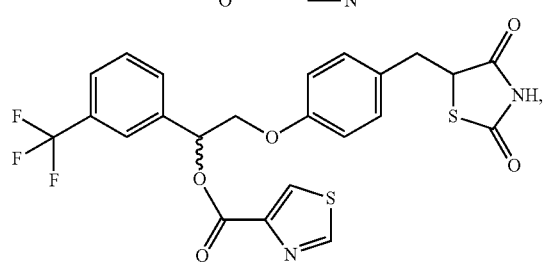
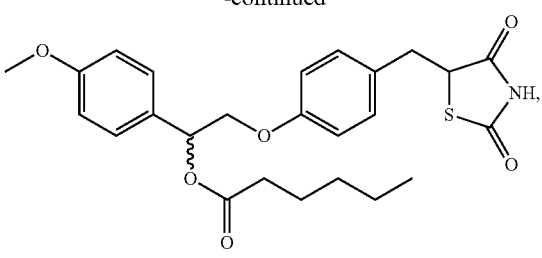
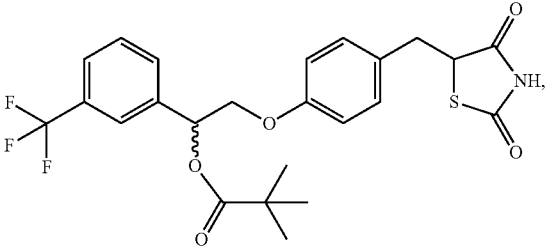
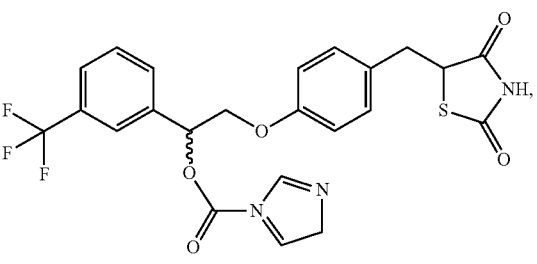
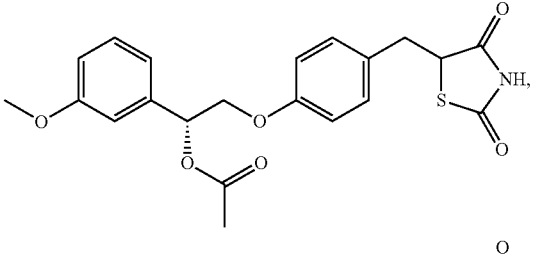
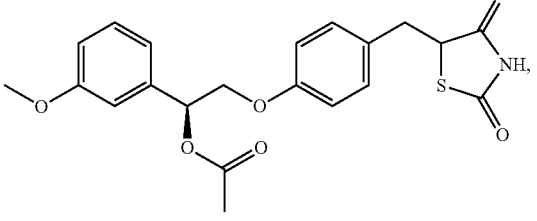
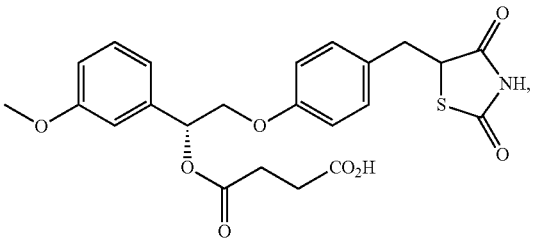
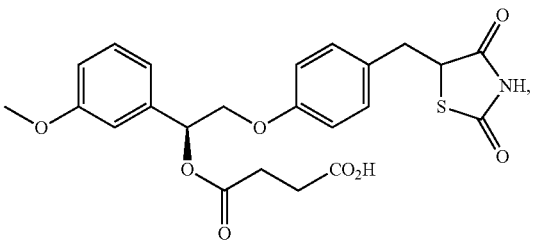

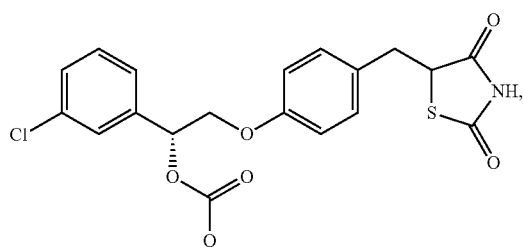
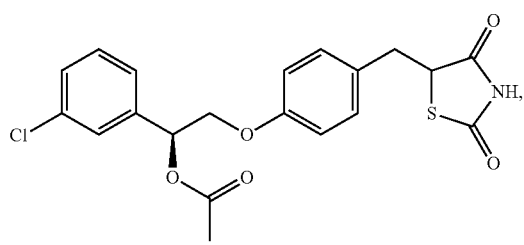
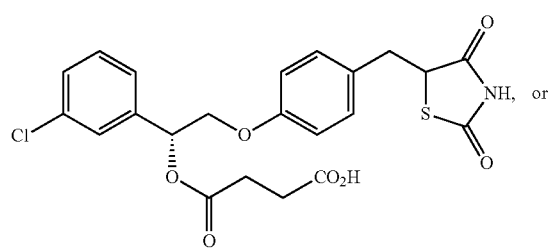
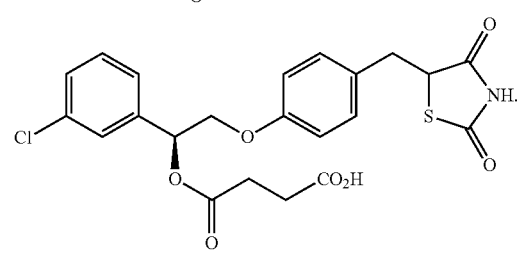
In some embodiments, the compound of Formula I is one selected from:
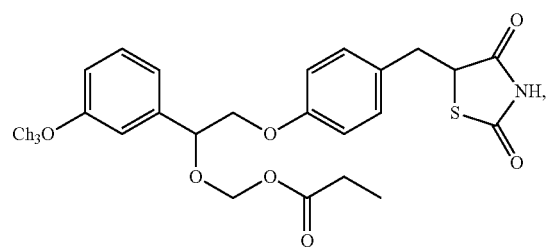
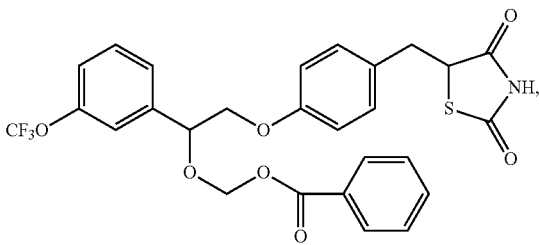
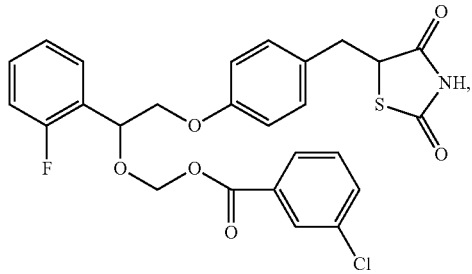
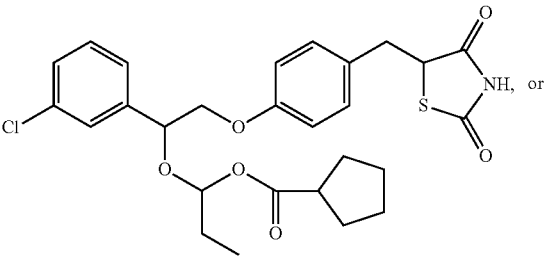
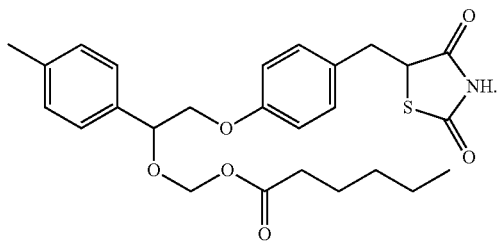
In some embodiments, the compound of Formula I is one selected from:
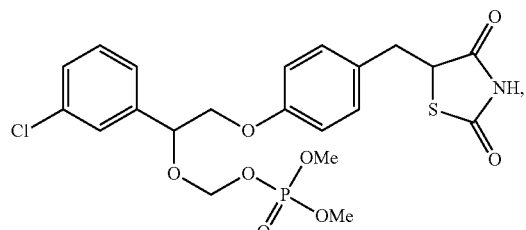
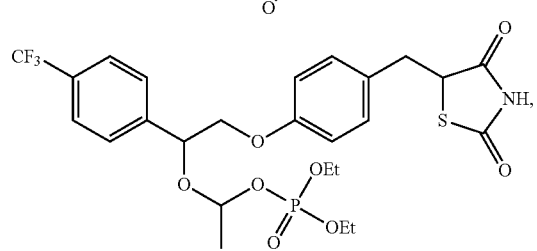

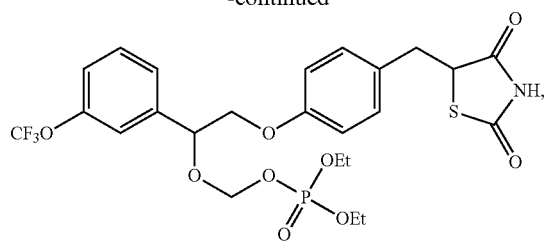
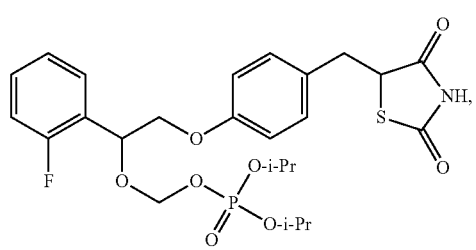
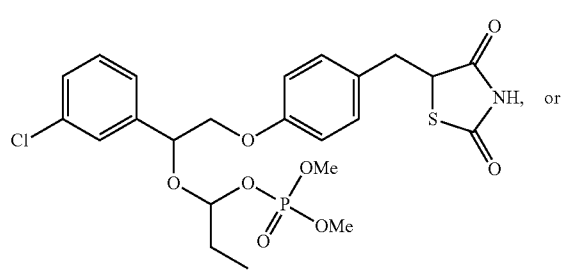
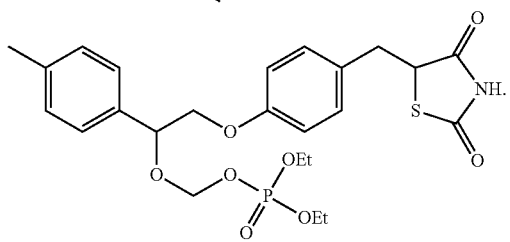
In some embodiments, the compound of Formula I is one selected from:
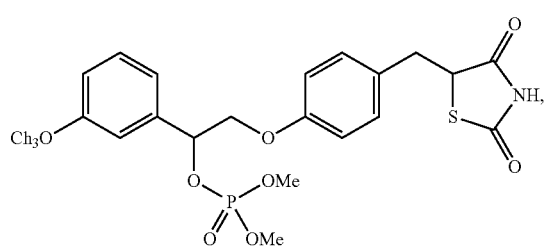
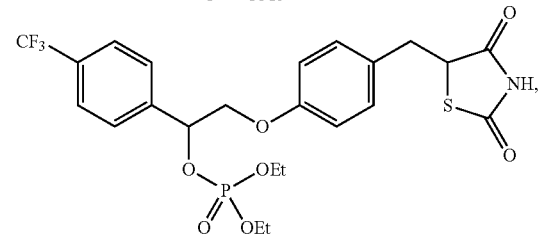
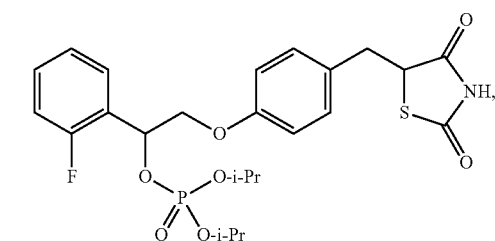
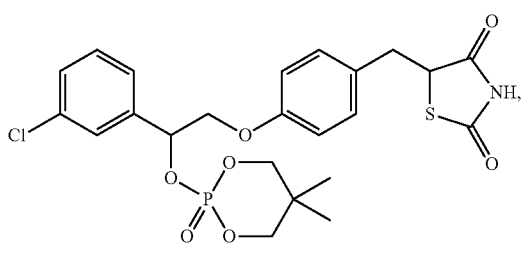
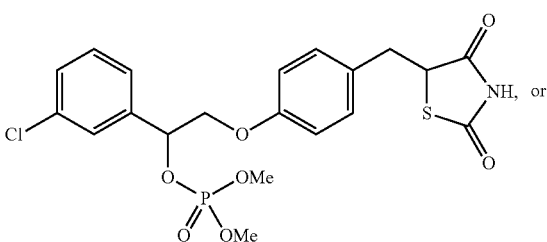
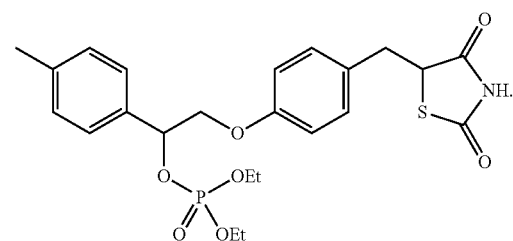
In some embodiments, the compound of Formula I is one selected from:
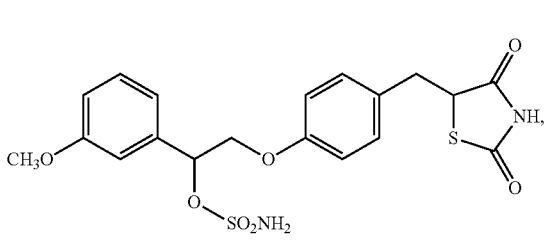

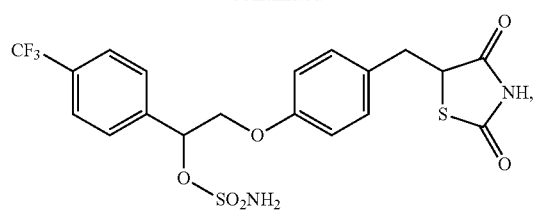
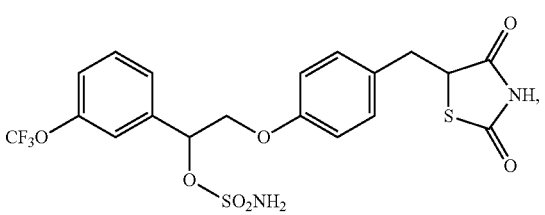
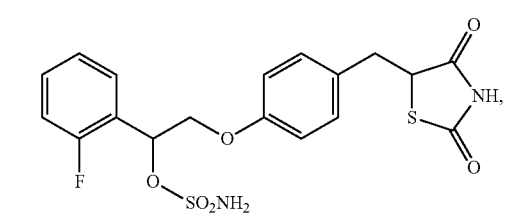
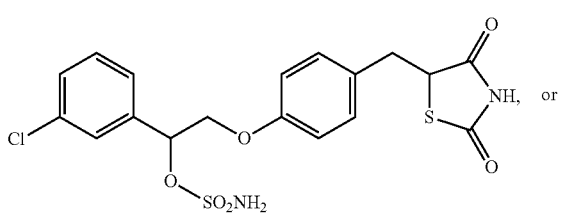
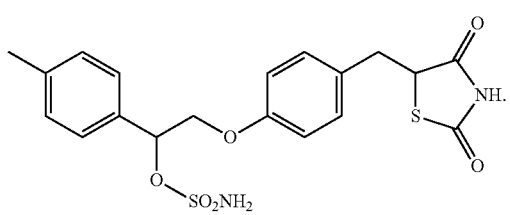
In some embodiments, the compound of Formula I is one selected from:
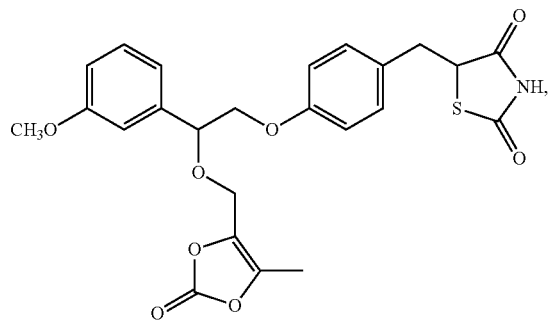
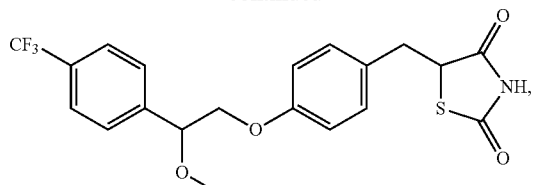
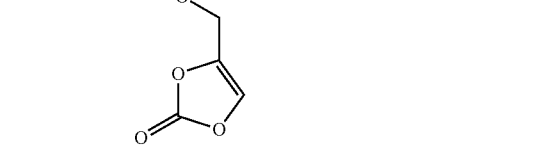
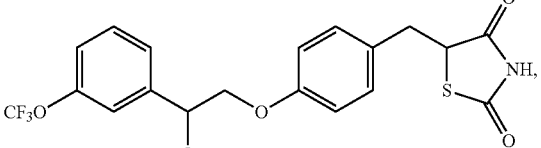
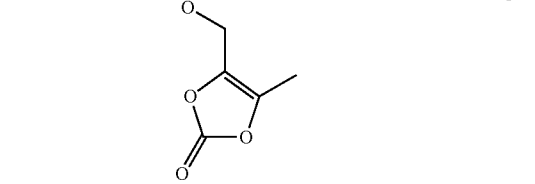
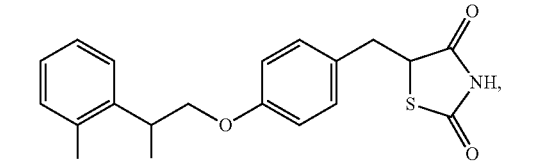
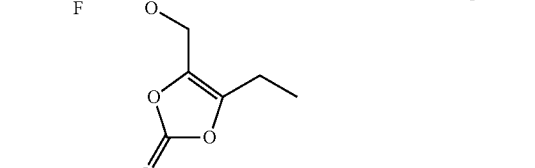
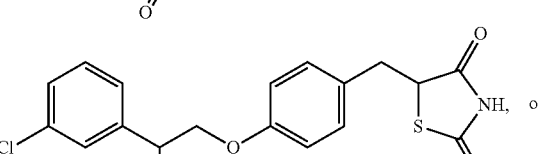
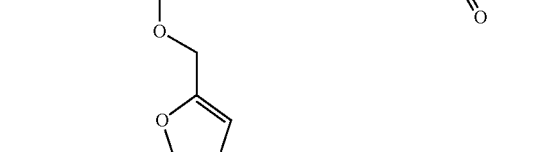
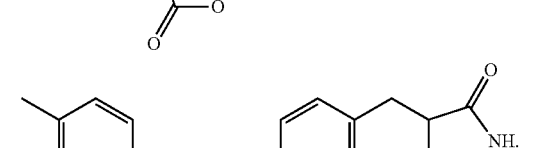
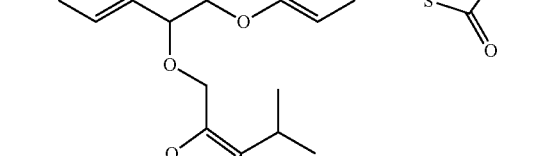

In some embodiments, the compound of Formula I is one selected from:
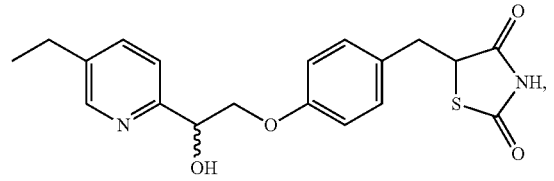
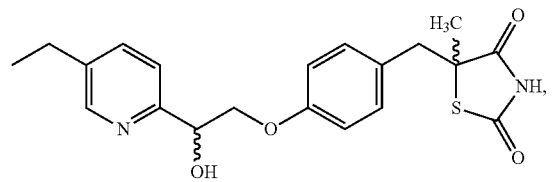
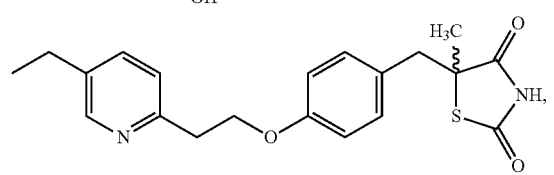
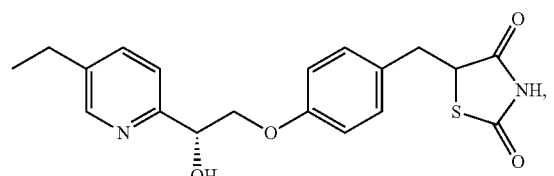
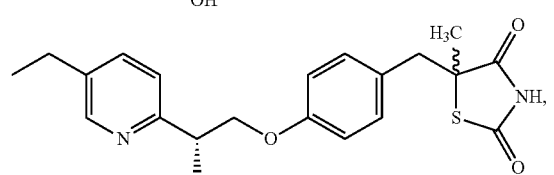
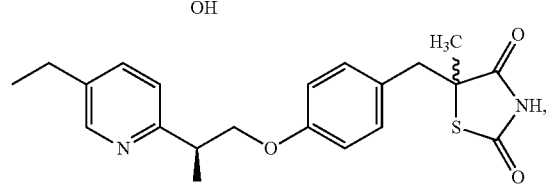
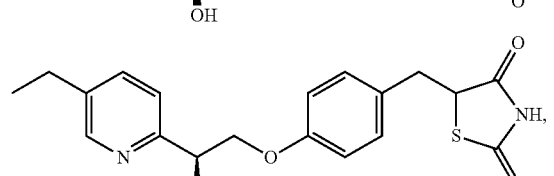
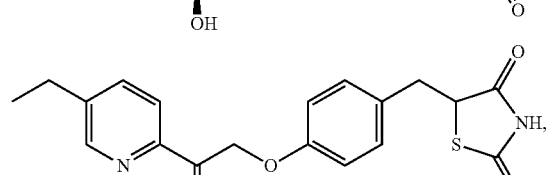
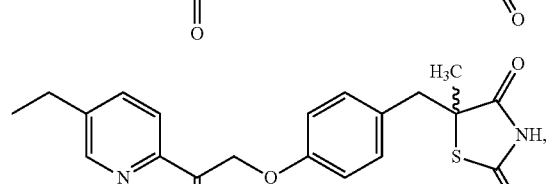
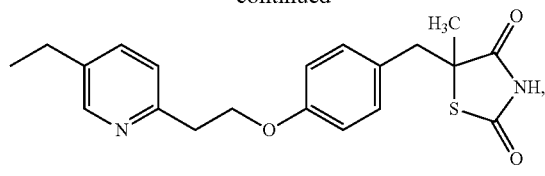
(+)-enantiomer
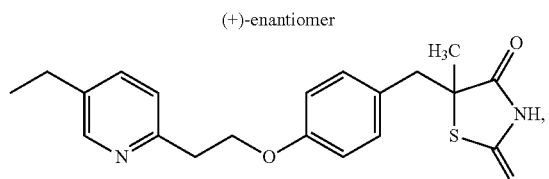
(−)-enantiomer
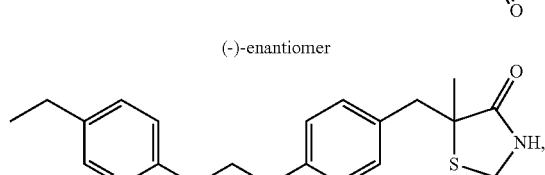
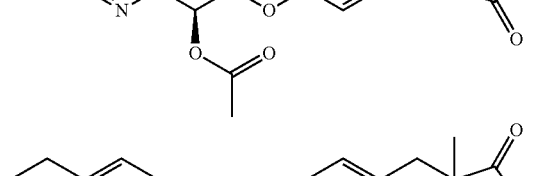
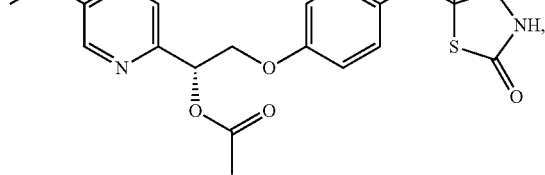
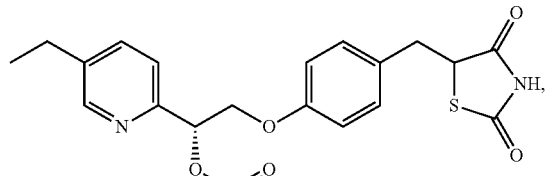
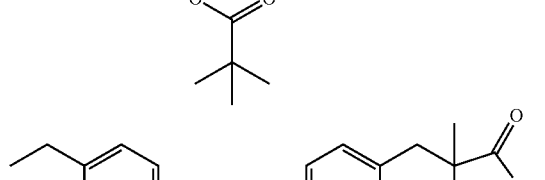
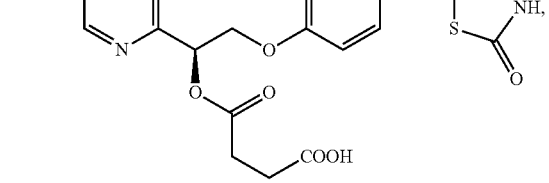
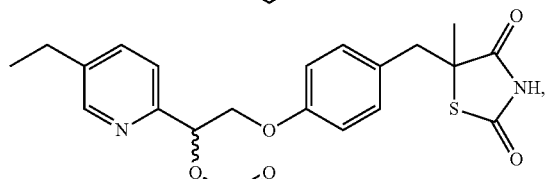
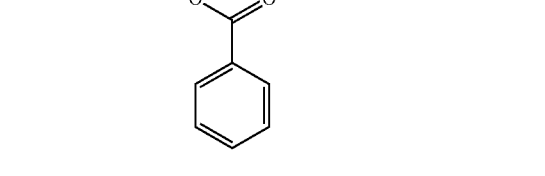

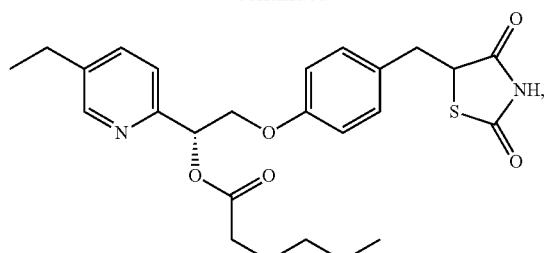
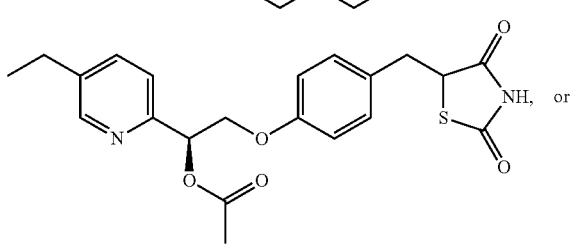
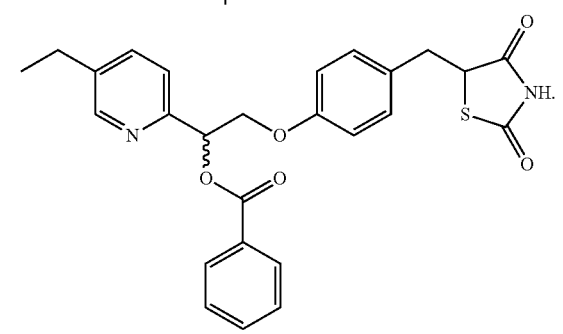
In some embodiments, the compound of Formula I is one selected from:
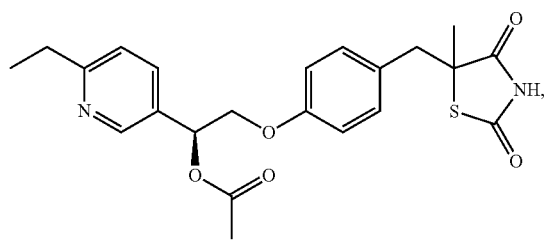
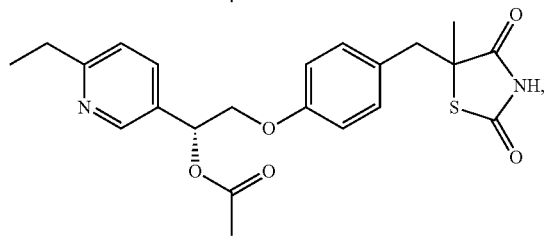
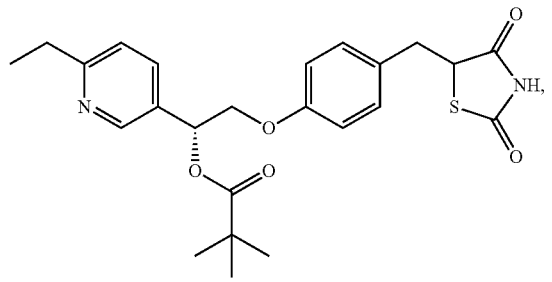
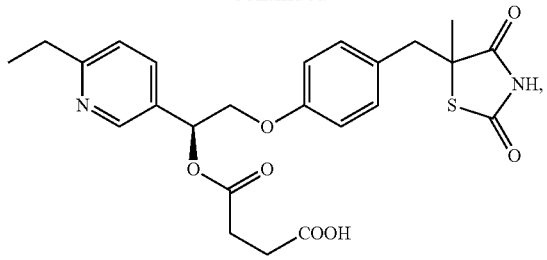
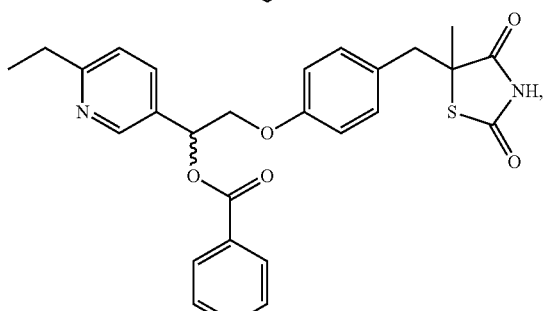
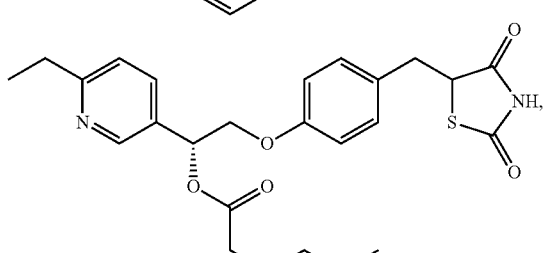
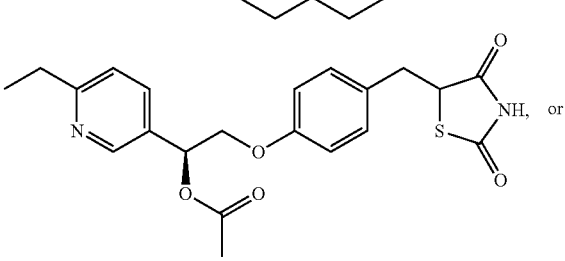
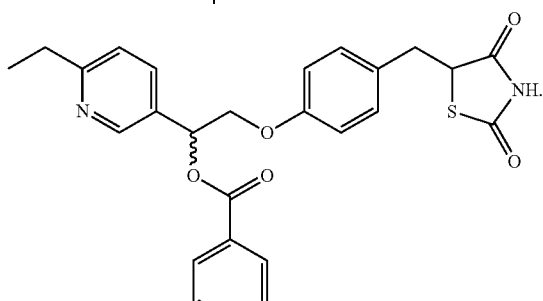
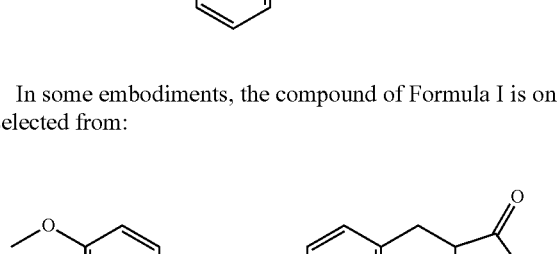
In some embodiments, the compound of Formula I is one selected from:
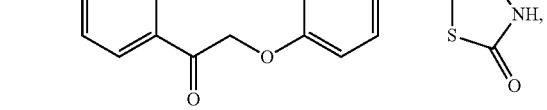

-continued
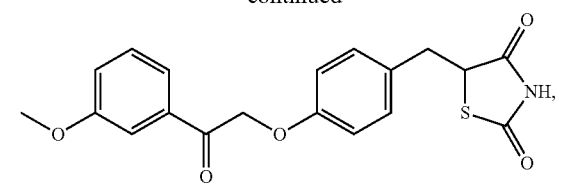
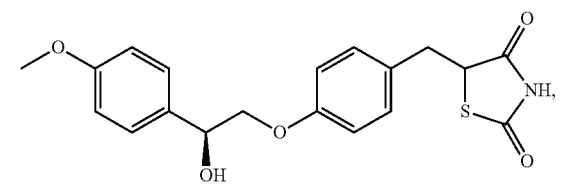
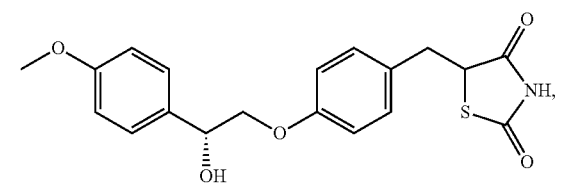
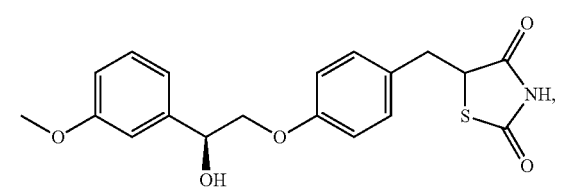
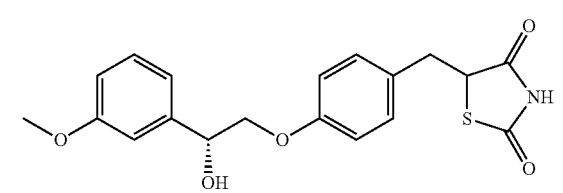
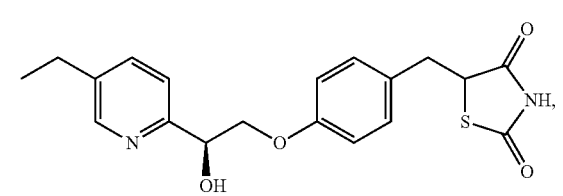
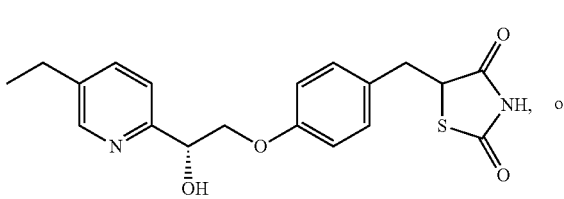
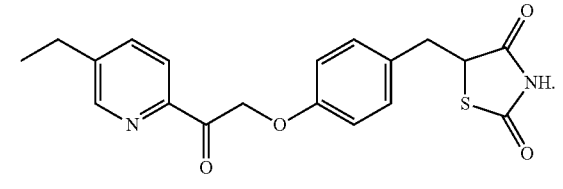
Another aspect of the present invention provides a hydrogen chloride salt of a compound selected from:
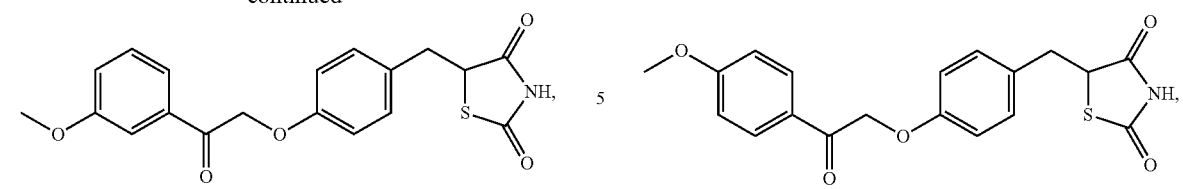
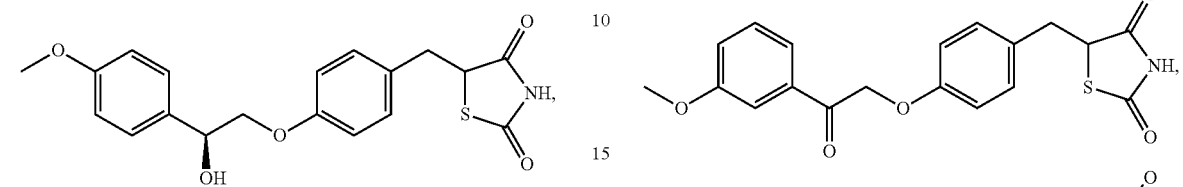
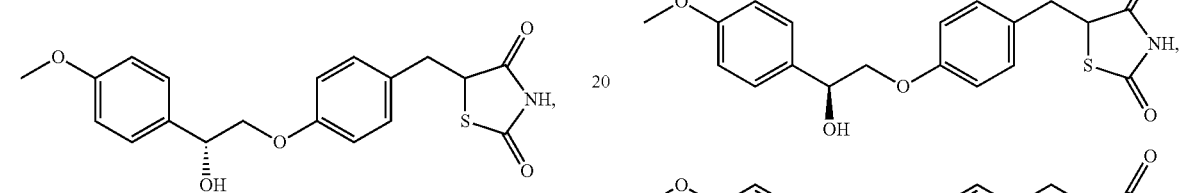
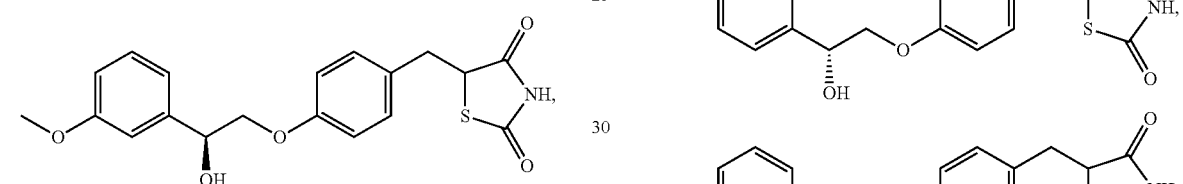
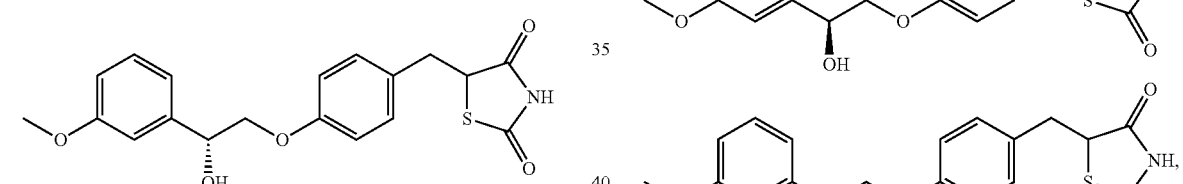
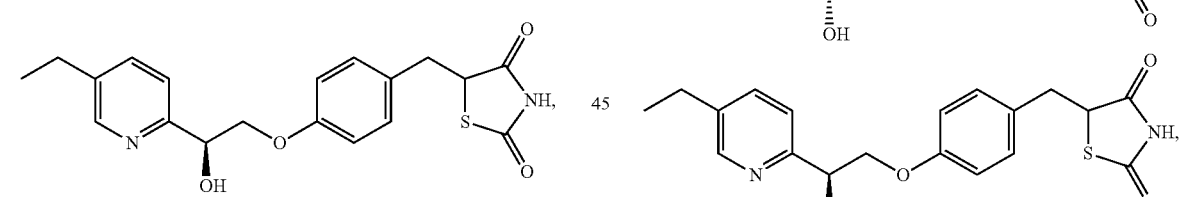
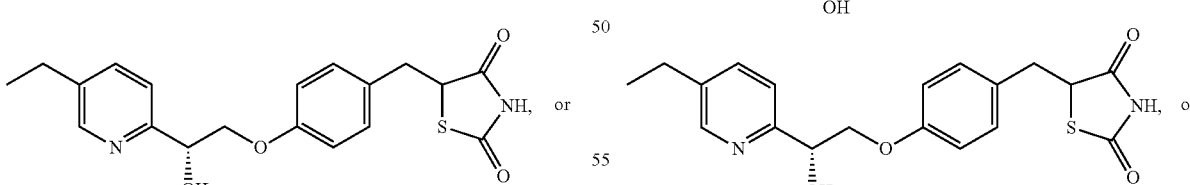
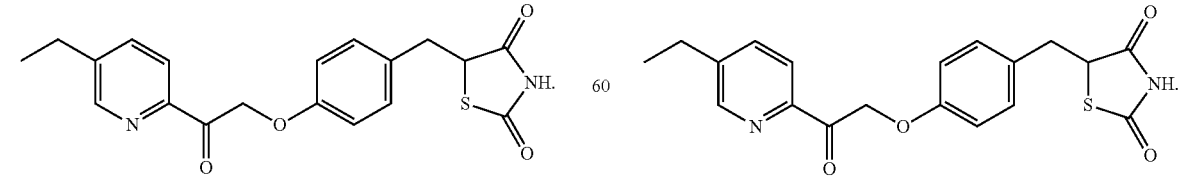
Another aspect of the present invention provides a dihydrogen sulfate salt of a compound selected from:

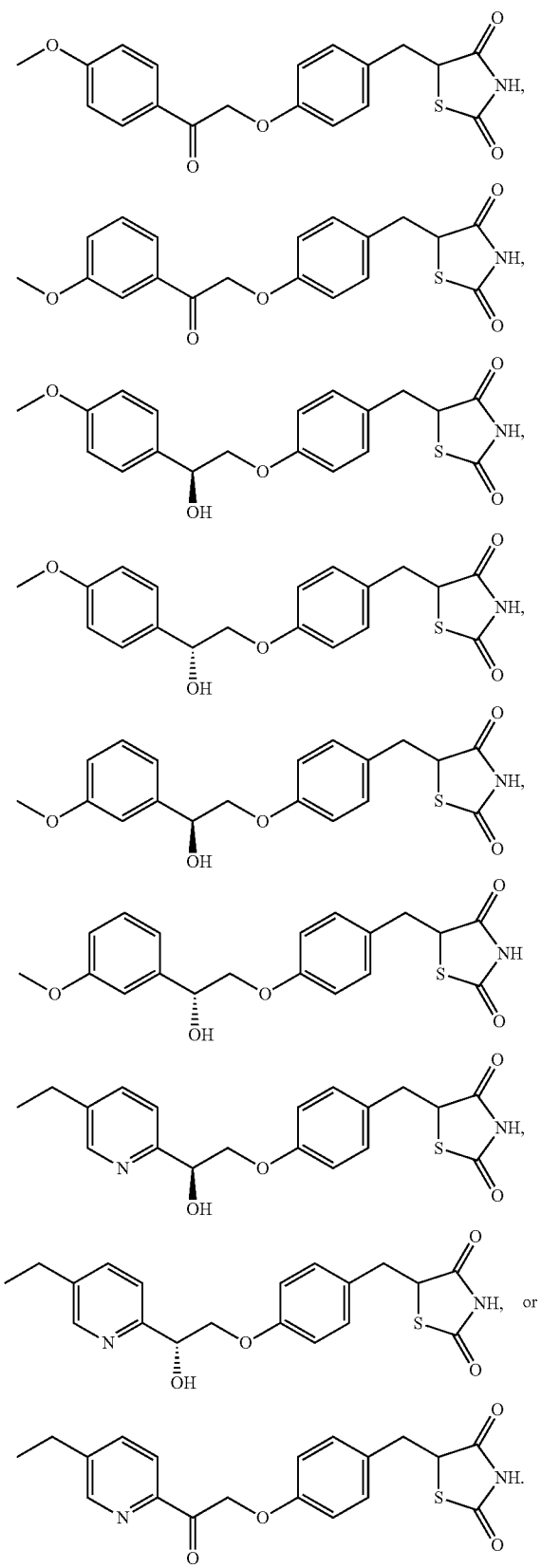

Another aspect of the present invention provides a hydrogen chloride salt of a compound of Formula IIIA or IIIB:

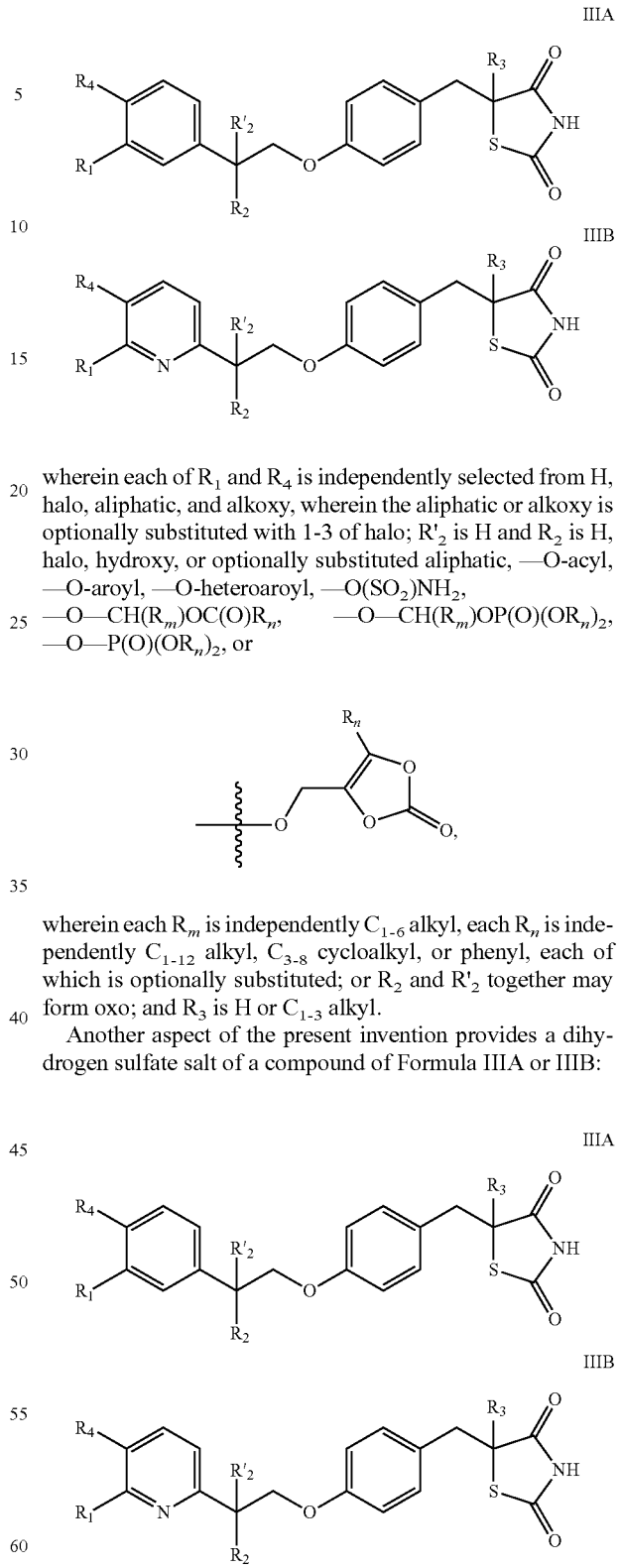

wherein each of $R_1$ and $R_4$ is independently selected from H, halo, aliphatic, and alkoxy, wherein the aliphatic or alkoxy is optionally substituted with 1-3 of halo; $R'_2$ is H and $R_2$ is H, halo, hydroxy, or optionally substituted aliphatic, —O-acyl, —O-aroyl, —O-heteroaroyl, —O(SO$_2$)NH$_2$, —O—CH(R$_m$)OC(O)R$_n$, —O—CH(R$_m$)OP(O)(OR$_n$)$_2$, —O—P(O)(OR$_n$)$_2$, or $$\begin{array}{c}\text{[structure]}\end{array}$$

wherein each $R_m$ is independently $C_{1-6}$ alkyl, each $R_n$ is independently $C_{1-12}$ alkyl, $C_{3-8}$ cycloalkyl, or phenyl, each of which is optionally substituted; or $R_2$ and $R'_2$ together may form oxo; and $R_3$ is H or $C_{1-3}$ alkyl.

Another aspect of the present invention provides a dihydrogen sulfate salt of a compound of Formula IIIA or IIIB:

wherein each of $R_1$ and $R_4$ is independently selected from H, halo, aliphatic, and alkoxy, wherein the aliphatic or alkoxy is optionally substituted with 1-3 of halo; $R'_2$ is H and $R_2$ is H, halo, hydroxy, or optionally substituted aliphatic, —O-acyl, —O-aroyl, —O-heteroaroyl, —O(SO$_2$)NH$_2$, —O—CH($R_m$)OC(O)$R_n$,    —O—CH($R_m$)OP(O)(O$R_n$)$_2$,
—O—P(O)(O$R_n$)$_2$, or

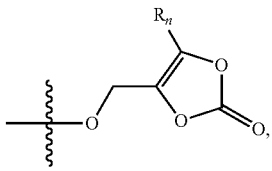

wherein each $R_m$ is independently $C_{1-6}$ alkyl, each $R_n$ is independently $C_{1-12}$ alkyl, $C_{3-8}$ cycloalkyl, or phenyl, each of which is optionally substituted; or $R_2$ and $R'_2$ together may form oxo; and $R_3$ is H or $C_{1-3}$ alkyl.

Another aspect of the present invention provides an alkali earth metal salt of a compound of Formula I:

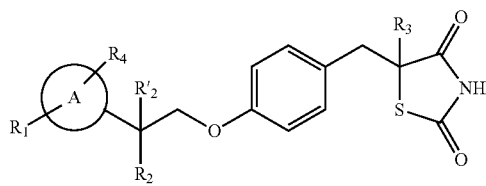

wherein each of $R_1$ and $R_4$ is independently selected from H, halo, aliphatic, and alkoxy, wherein the aliphatic or alkoxy is optionally substituted with 1-3 of halo; $R'_2$ is H and $R_2$ is H, halo, hydroxy, or optionally substituted aliphatic, —O-acyl, —O-aroyl, —O-heteroaroyl, —O(SO$_2$)NH$_2$,
—O—CH($R_m$)OC(O)$R_n$,    —O—CH($R_m$)OP(O)(O$R_n$)$_2$,
—O—P(O)(O$R_n$)$_2$, or

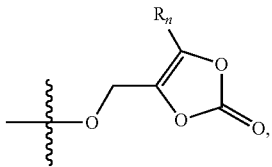

wherein each $R_m$ is independently $C_{1-6}$ alkyl, each $R_n$ is independently $C_{1-12}$ alkyl, $C_{3-8}$ cycloalkyl, or phenyl, each of which is optionally substituted; or $R_2$ and $R'_2$ together may form oxo; $R_3$ is H or $C_{1-3}$ alkyl; and ring A is phenyl, pyridin-2-yl, pyridin-3-yl or pyridin-4-yl, each of which is substituted with an $R_1$ group and an $R_4$ group at any chemically feasible position on ring A.

In some embodiments, the alkali earth metal is potassium.
In some embodiments, the alkali earth metal is sodium.
In some embodiments, $R_3$ is H.
In some embodiments, $R_3$ is CH$_3$.
In some embodiments, $R_4$ is H, methyl, methoxy, ethoxy, —O-isopropyl, —CF$_3$, —OCHF$_2$ or —OCF$_3$.
In some embodiments, $R_4$ is H.
In some embodiments, $R_1$ is H, alkyl, halo or alkoxy.
In some embodiments, $R_1$ is H.
In some embodiments, $R_1$ is halo.
In some embodiments, $R_1$ is $C_{1-3}$ alkyl.
In some embodiments, ring A is phenyl that is substituted with $R_1$ and $R_4$ groups at any chemically feasible position on ring A. In some examples, ring A is phenyl, and one of $R_1$ or $R_4$ is attached to the para or meta position of ring A. In other examples, ring A is phenyl, and one of $R_1$ or $R_4$ is attached to the meta position of ring A. In some examples, $R_1$ is attached to the para or meta position of ring A. And, in some examples, $R_1$ is F or Cl, either of which is attached to the para or meta position of ring A. In other examples, $R_1$ is alkoxy (e.g., methoxy, ethoxy, propoxy, —O-isopropyl, butoxy, or —O-tertbutyl) that is attached to the para or meta position of ring A. In other examples, ring A is phenyl, and $R_1$ is attached to the meta or ortho position of the phenyl ring. For instance, ring A is phenyl, and $R_1$ is attached to the ortho position of the phenyl ring. In some instances, ring A is phenyl, and $R_1$ is methoxy, ethoxy, or —O-isopropyl, any of which is attached to the ortho position of ring A. In other instances, $R_1$ is —CF$_3$, —OCHF$_2$ or —OCF$_3$.

In some embodiments, ring A is optionally substituted pyridin-2-yl or optionally substituted pyridin-3-yl, either of which is substituted with $R_1$ and $R_4$ groups at any chemically feasible position on ring A. In some examples, ring A is pyridin-2-yl, and one of $R_1$ or $R_4$ is attached to the 5 position of the ring. In other examples, ring A is pyridin-3-yl, and one of $R_1$ or $R_4$ is attached to the 6 position of the ring. In some examples, ring A is pyridin-2-yl, and $R_1$ is attached to the 5 position of the ring. For instance, ring A is pyridin-2-yl, and $R_1$ is alkyl or alkoxy, either of which is attached to the 5 position of ring A. In other instances, ring A is pyridin-2-yl, and $R_1$ is methyl, ethyl, propyl, isopropyl, butyl, or tertbutyl, any of which are attached to the 5 position of ring A.

In some embodiments, $R'_2$ is H.
In some embodiments, $R_2$ is hydroxy.
In some embodiments, $R_2$ is —O-acyl, —O-aroyl, or —O-heteroaroyl.
In some embodiments, $R_2$ and $R'_2$ together form oxo.
In some embodiments, the compound of Formula I is one selected from:

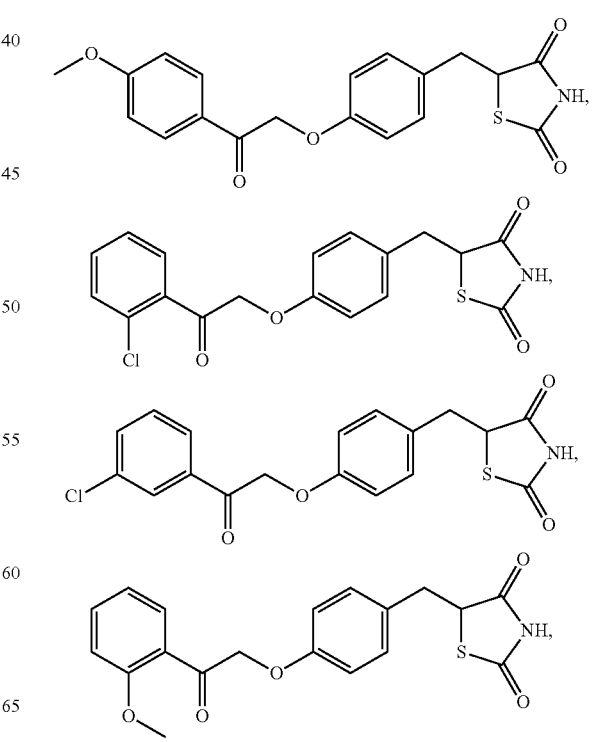

-continued
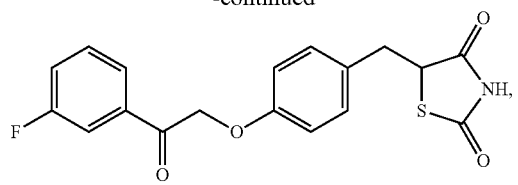
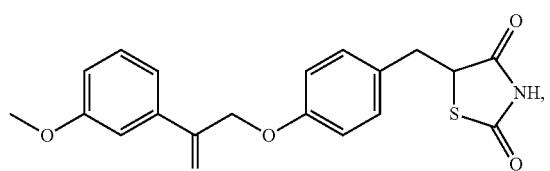
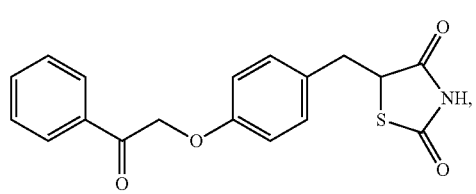
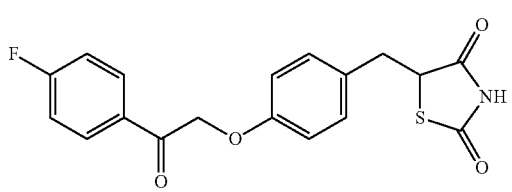
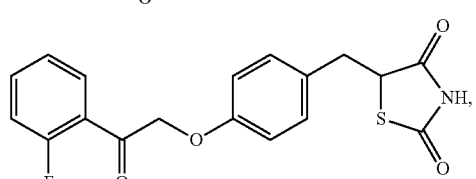
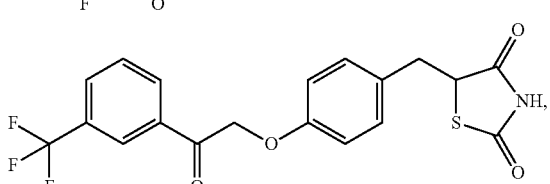
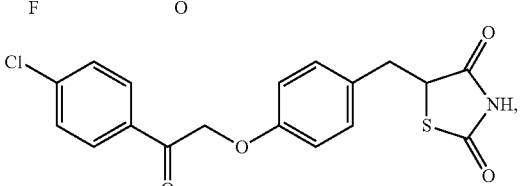
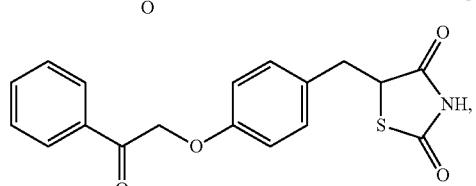
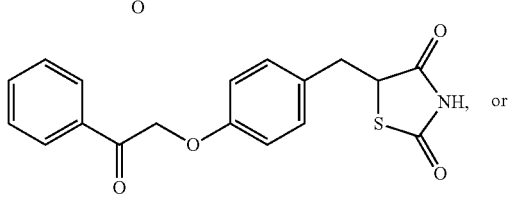 or
-continued
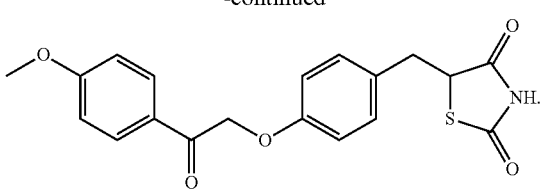
In some embodiments, the compound of Formula I is one selected from:
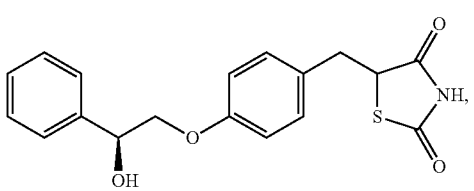
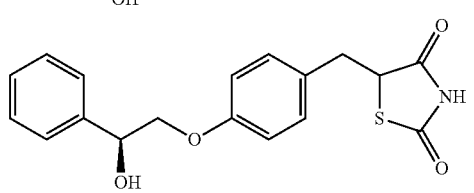
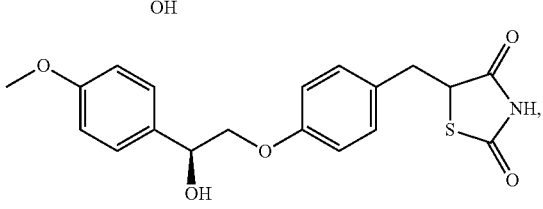
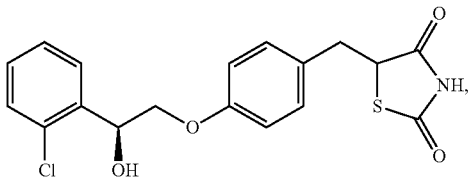
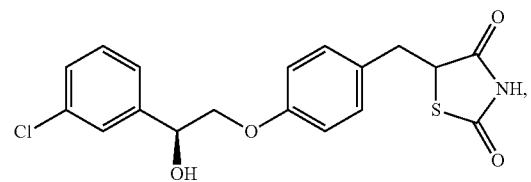
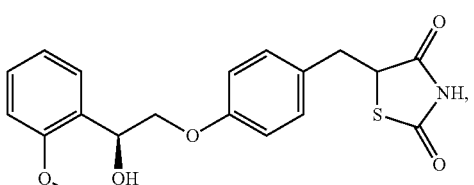
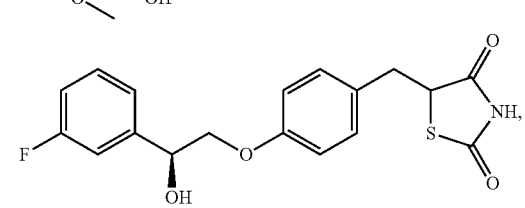

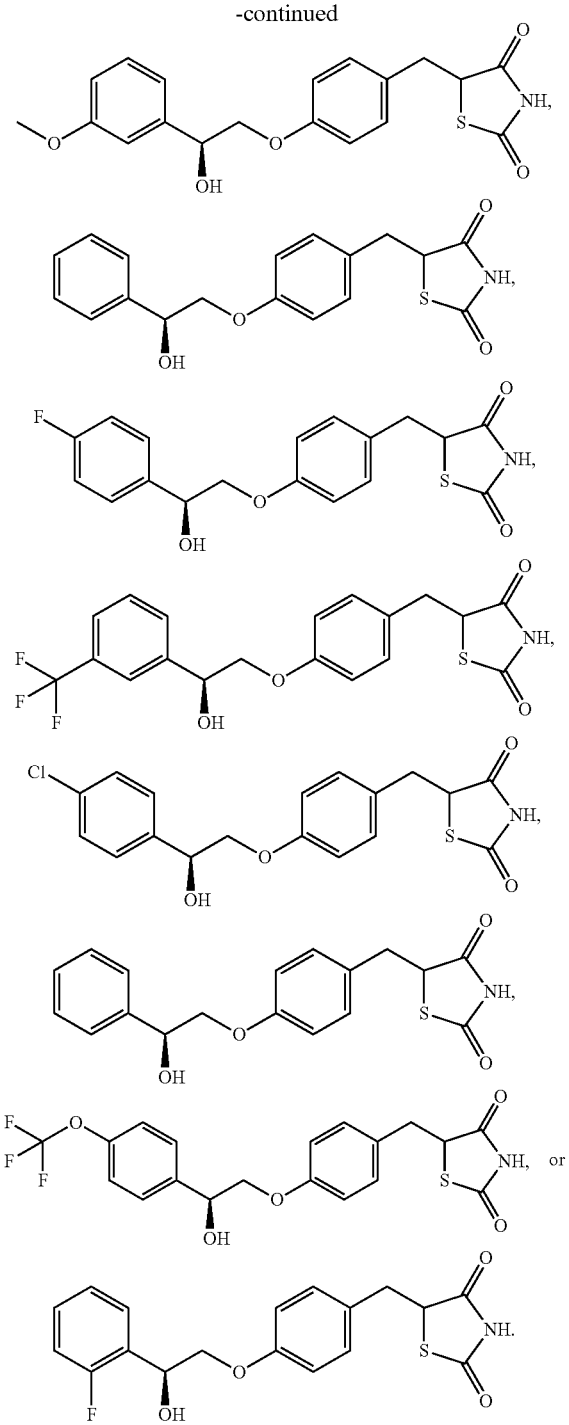
In some embodiments, the compound of Formula I is one selected from:
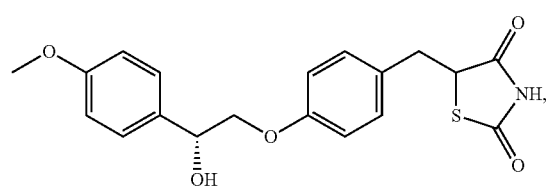
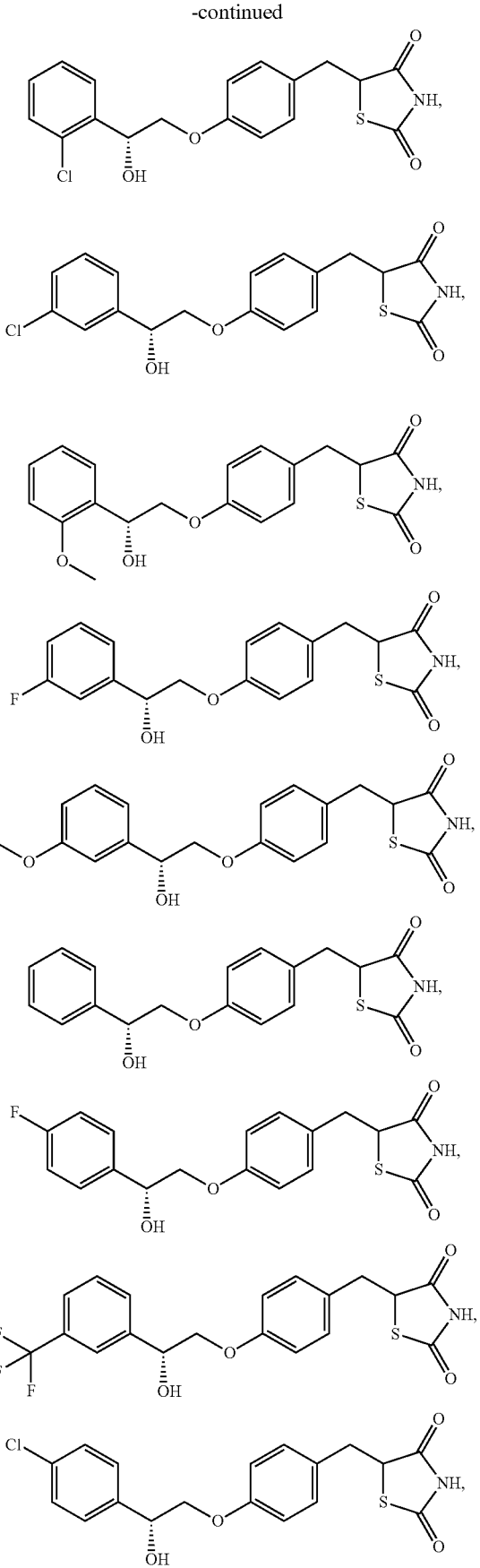

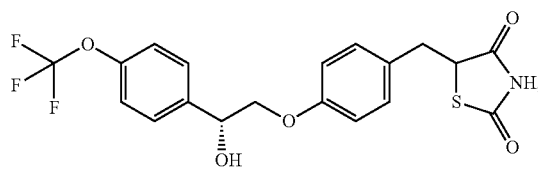
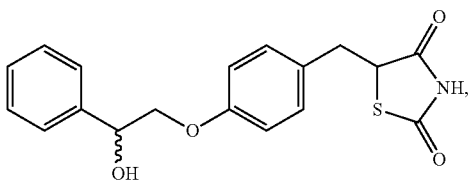 [SMILES: O=C1NC(=O)C(Cc2ccc(OCC(O)c3ccccc3)cc2)S1]
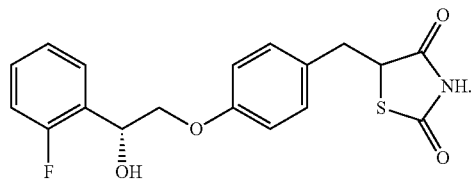
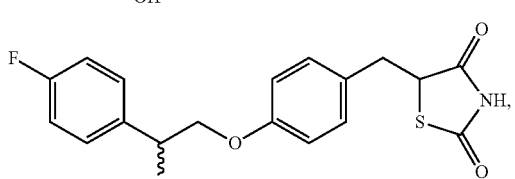
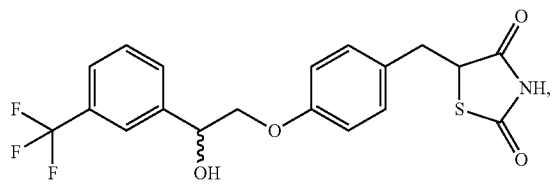 [SMILES: O=C1NC(=O)C(Cc2ccc(OCC(O)c3cccc(C(F)(F)F)c3)cc2)S1]
In some embodiments, the compound of Formula I is one selected from:
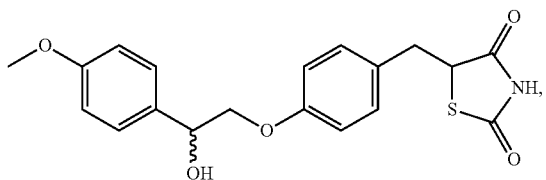
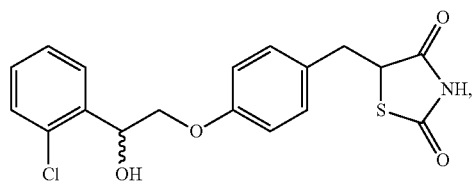
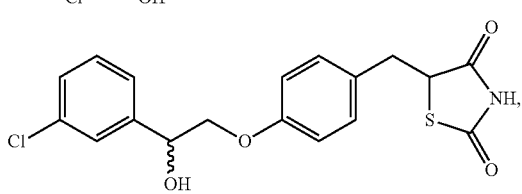
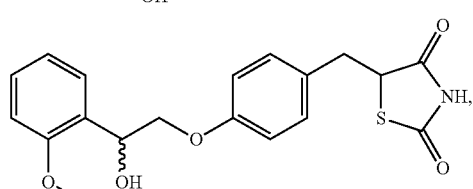
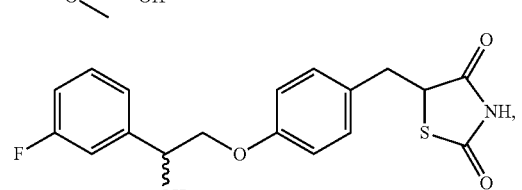
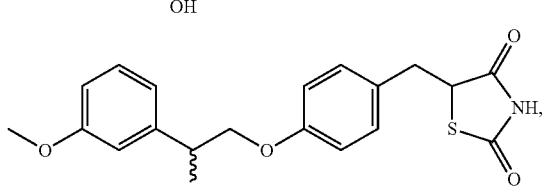
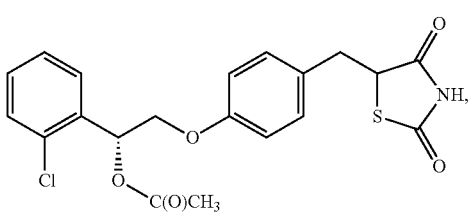
In some embodiments, the compound of Formula I is one selected from:
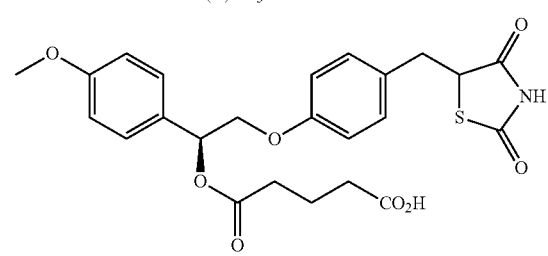

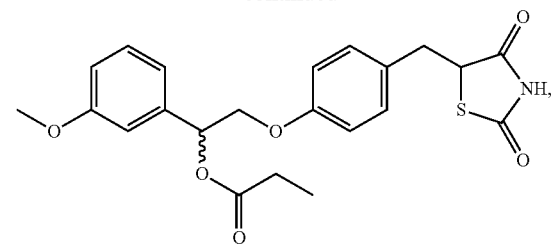 [SMILES: CCC(=O)OC(COc1ccc(CC2SC(=O)NC2=O)cc1)c1cccc(OC)c1]
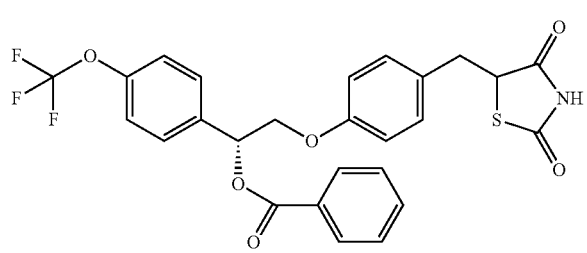 [SMILES: O=C1NC(=O)C(Cc2ccc(OC[C@H](OC(=O)c3ccccc3)c3ccc(OC(F)(F)F)cc3)cc2)S1]
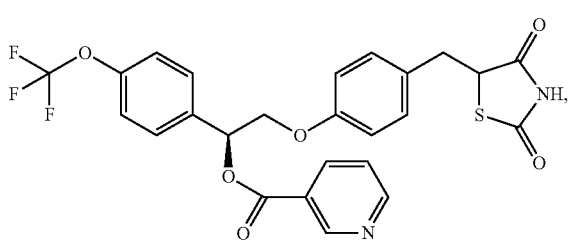 [SMILES: O=C1NC(=O)C(Cc2ccc(OC[C@@H](OC(=O)c3cccnc3)c3ccc(OC(F)(F)F)cc3)cc2)S1]
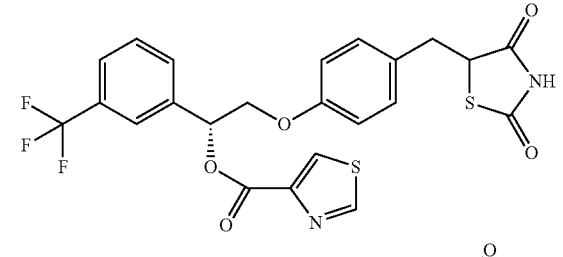
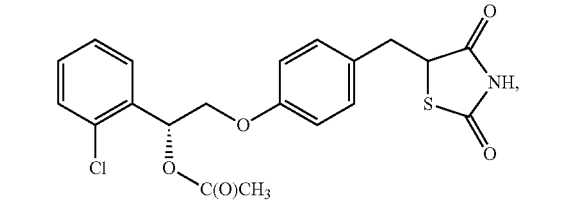
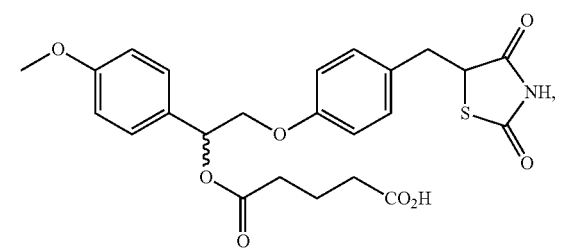 [SMILES: COc1ccc(C(COc2ccc(CC3SC(=O)NC3=O)cc2)OC(=O)CCCC(=O)O)cc1]
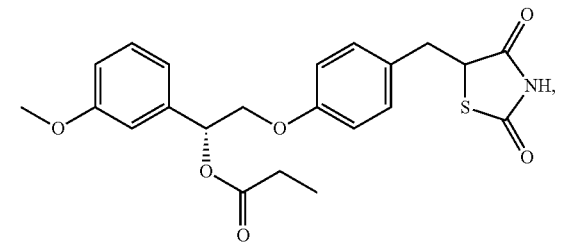 [SMILES: CCC(=O)OC(COc1ccc(CC2SC(=O)NC2=O)cc1)c1cccc(OC)c1]
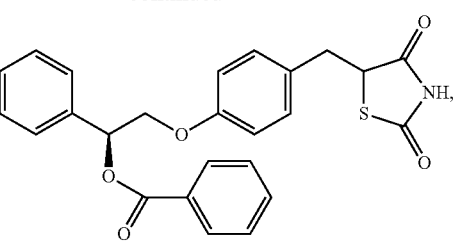
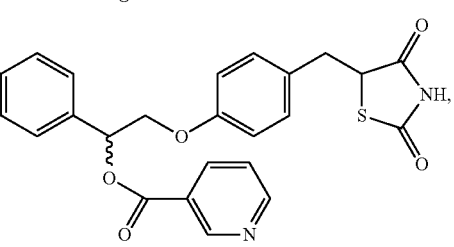
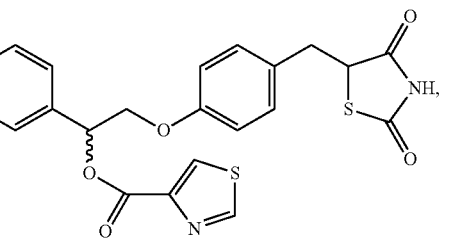
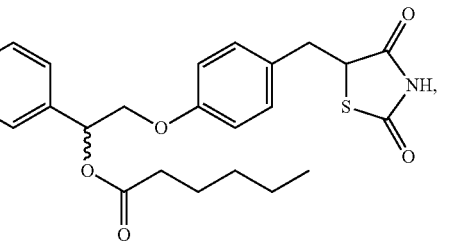
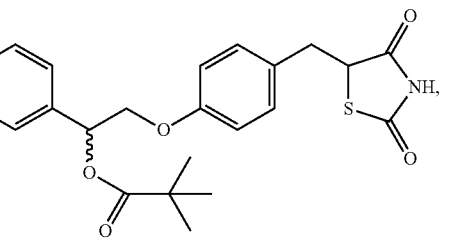
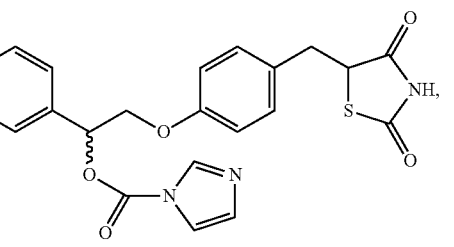
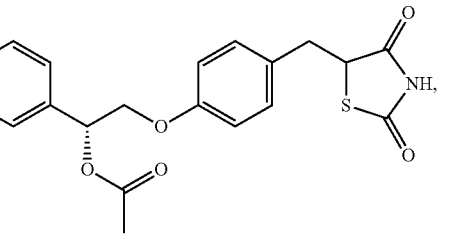

-continued
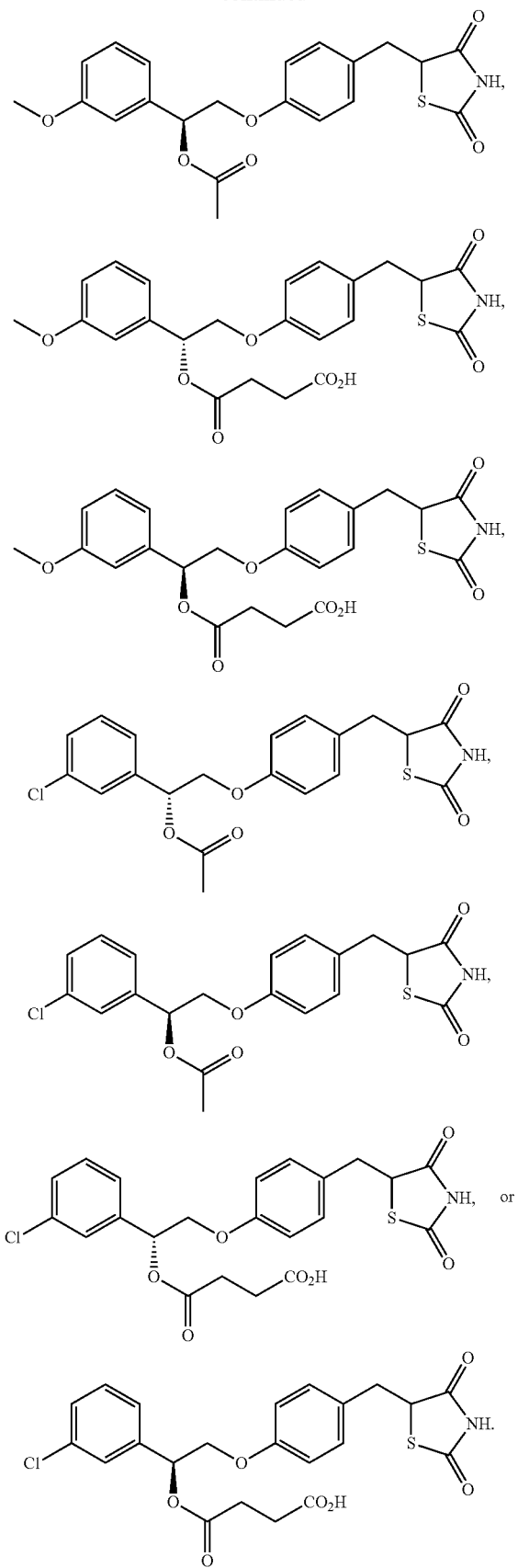
In some embodiments, the compound of Formula I is one selected from:
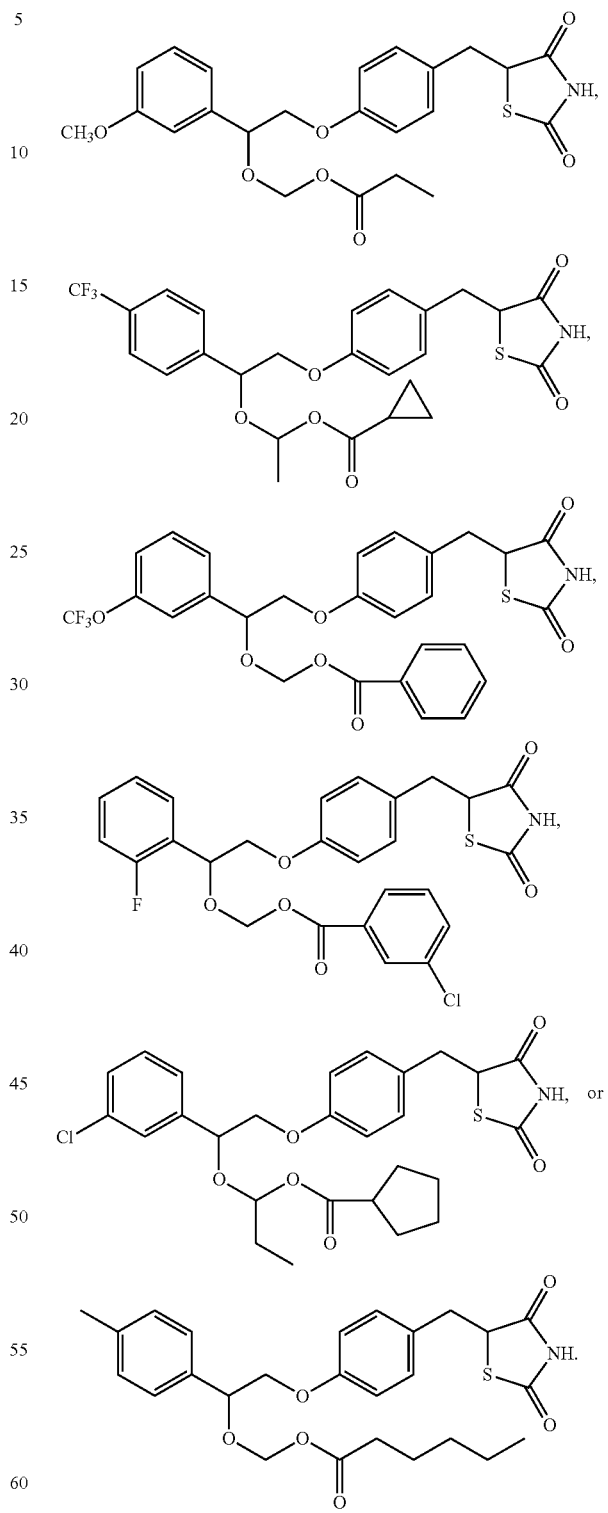
or
In some embodiments, the compound of Formula I is one selected from:

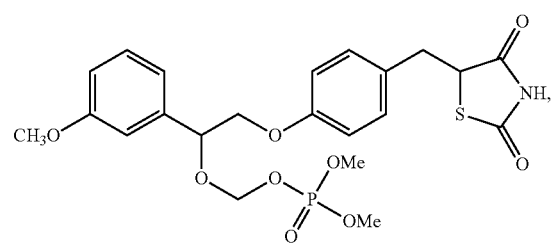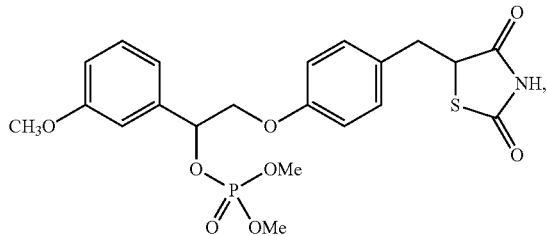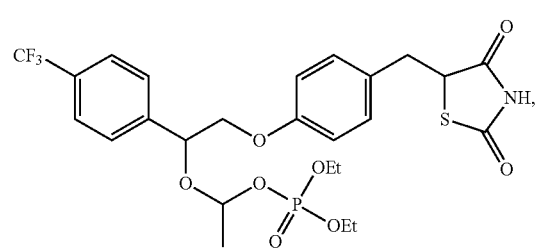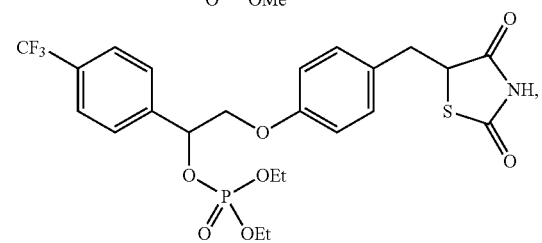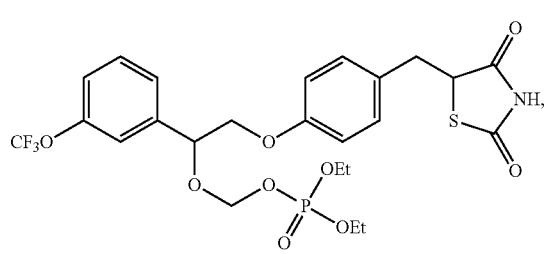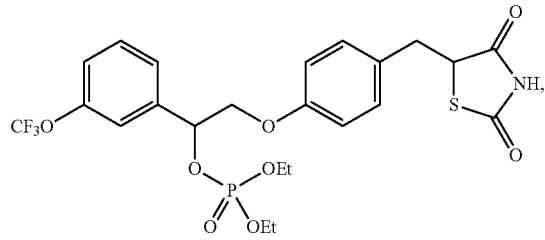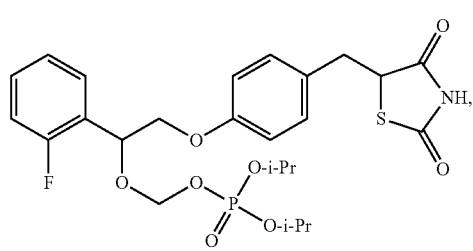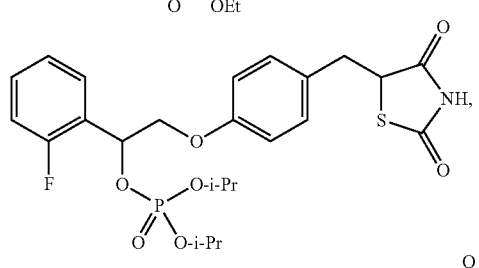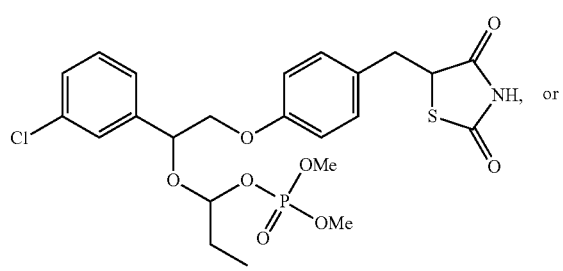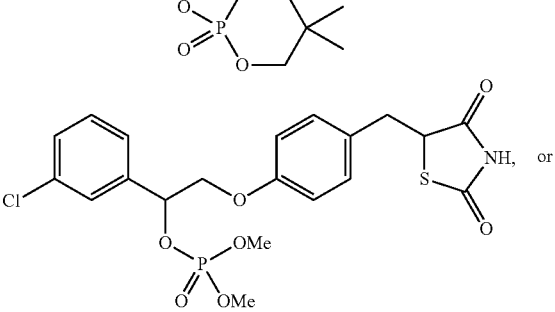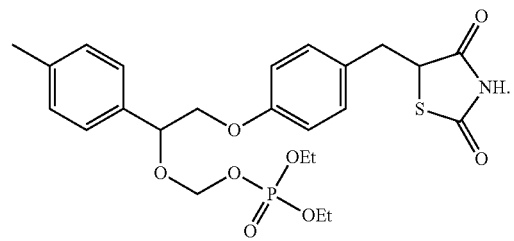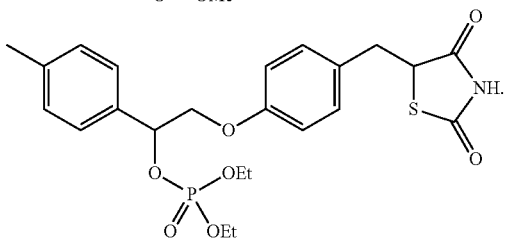
In some embodiments, the compound of Formula I is one selected from:
In some embodiments, the compound of Formula I is one selected from:

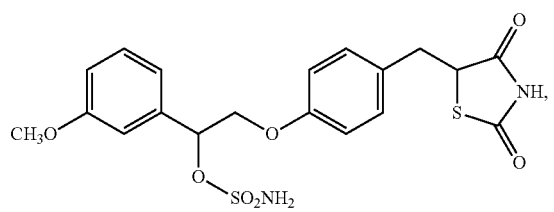
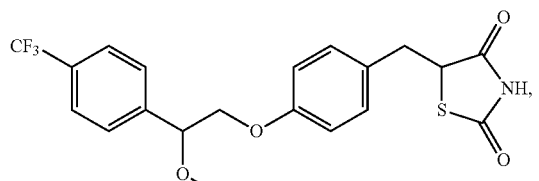
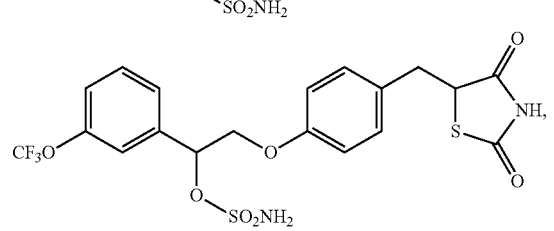
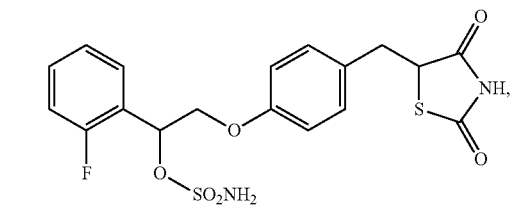
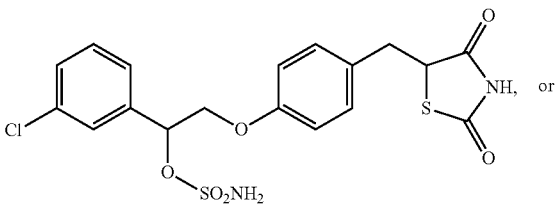
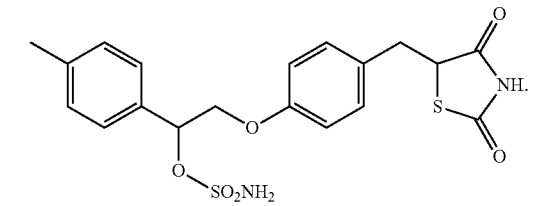
In some embodiments, the compound of Formula I is one selected from:
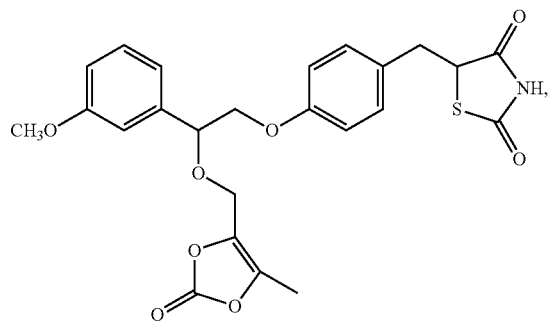
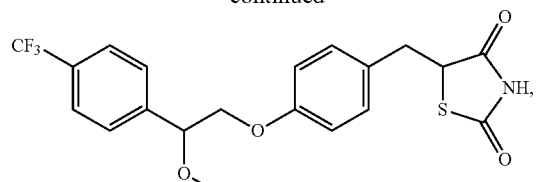
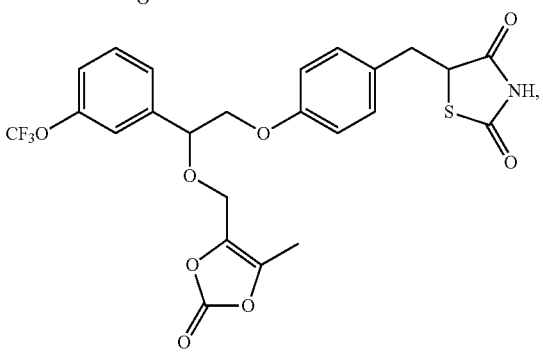
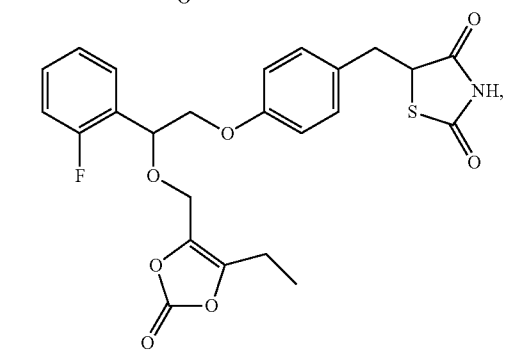
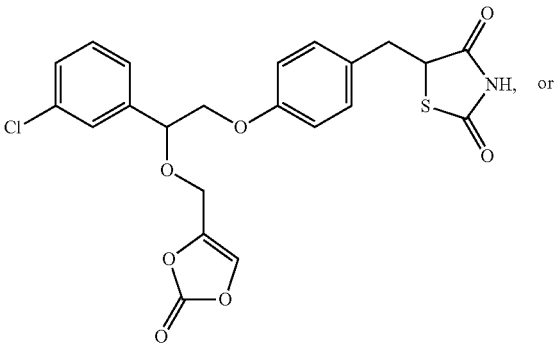
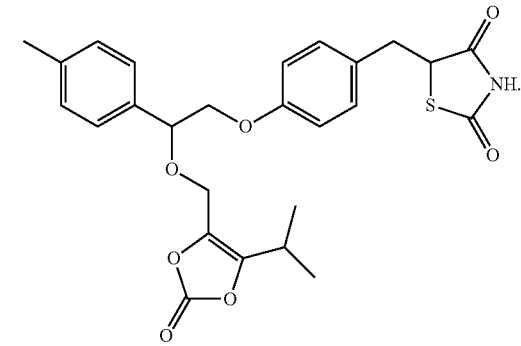

In some embodiments, the compound of Formula I is one selected from:
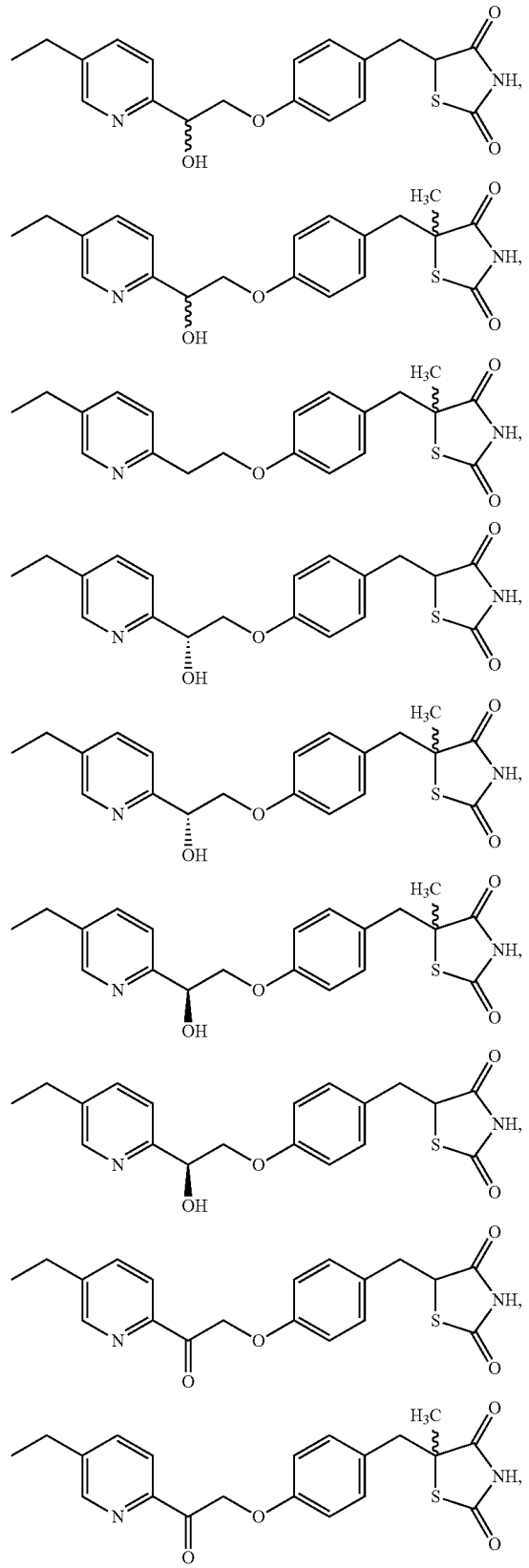
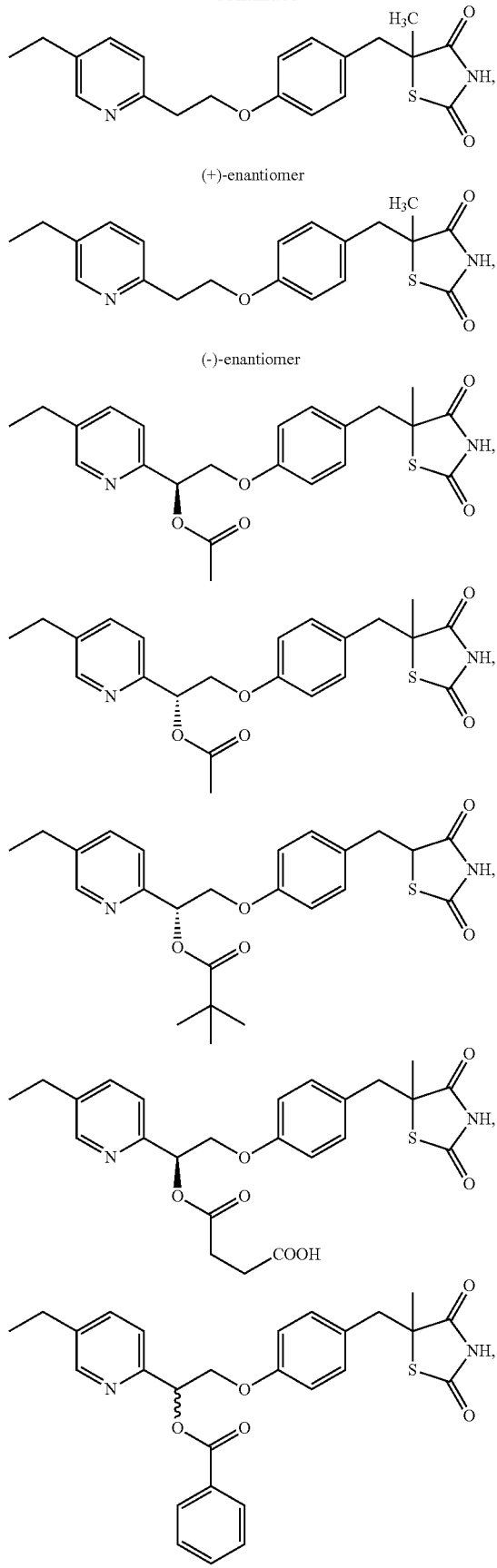

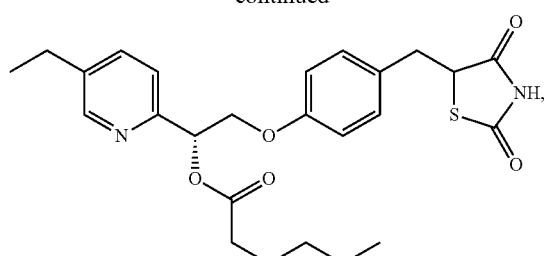
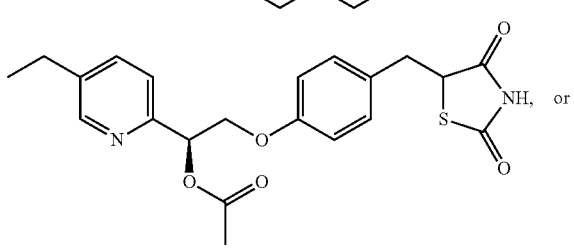
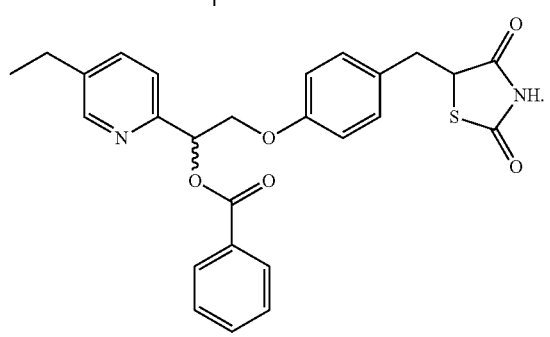
In some embodiments, the compound of Formula I is one selected from:
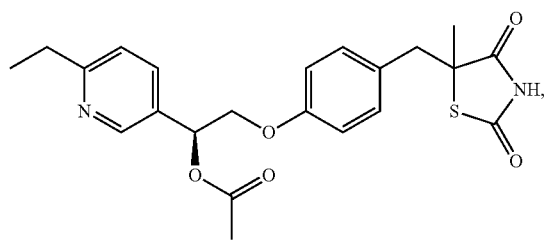
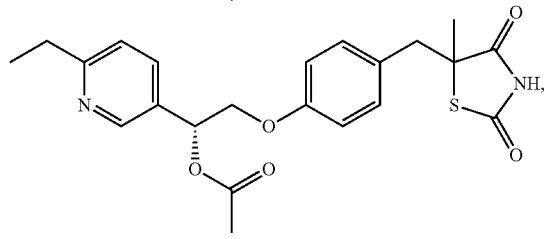
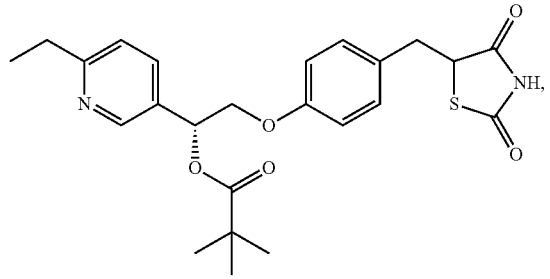
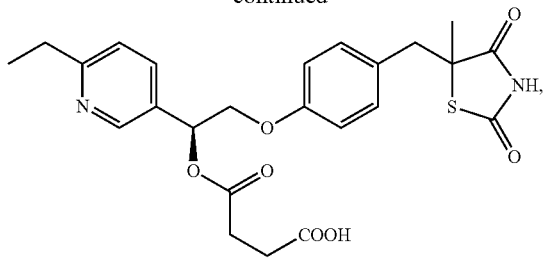
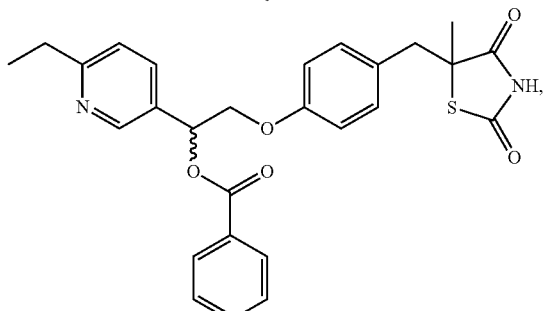
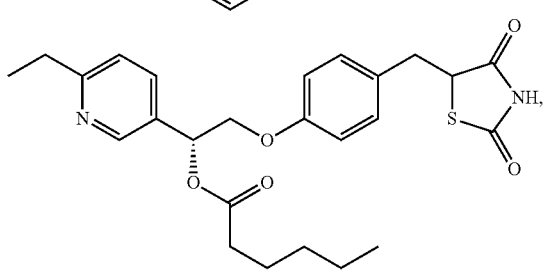
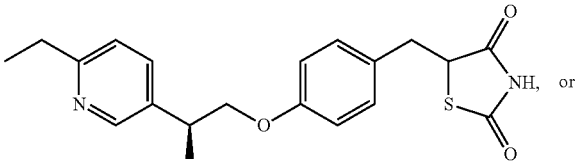
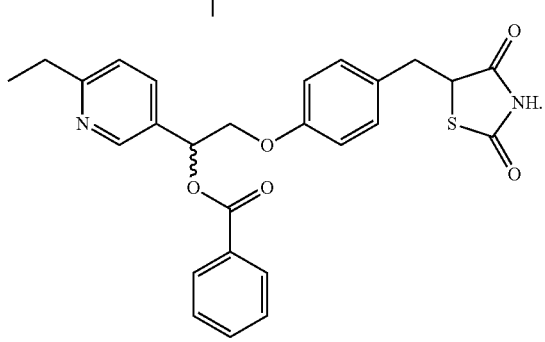
In some embodiments, the compound of Formula I is one selected from:
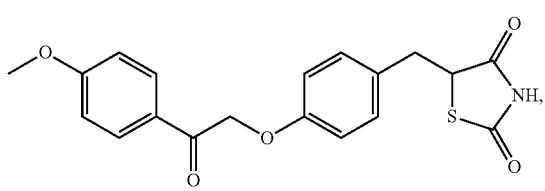

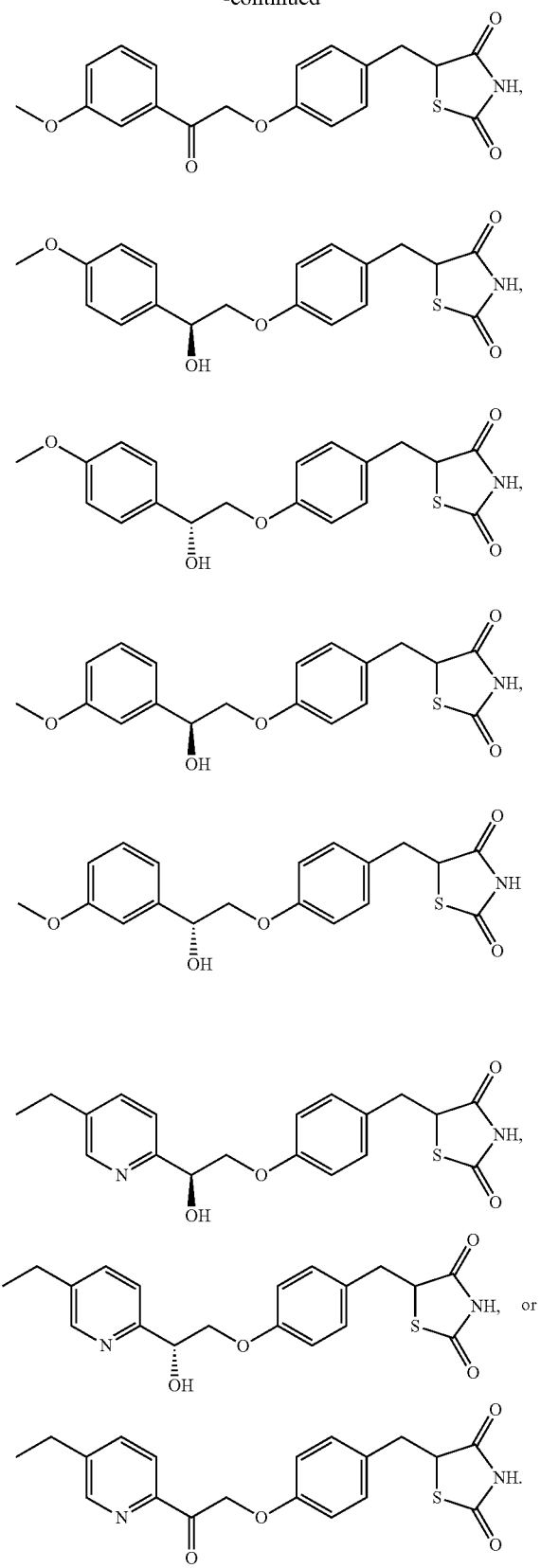
Another aspect of the present invention provides an alkali earth metal salt of a compound selected from:
Another aspect of the present invention provides an alkali earth metal salt of a compound of Formula IIIA or IIIB:

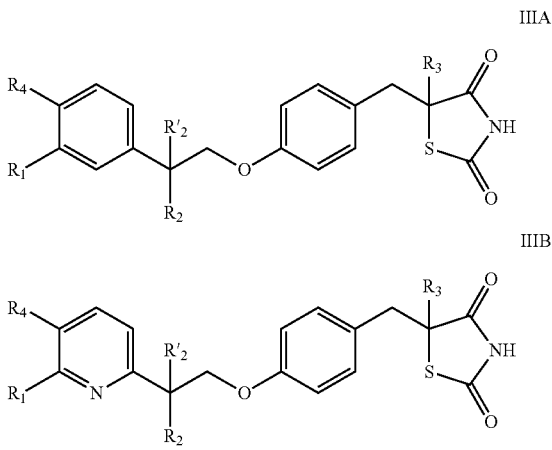

wherein each of $R_1$ and $R_4$ is independently selected from H, halo, aliphatic, and alkoxy, wherein the aliphatic or alkoxy is optionally substituted with 1-3 of halo; $R'_2$ is H and $R_2$ is H, halo, hydroxy, or optionally substituted aliphatic, —O-acyl, —O-aroyl, —O-heteroaroyl, —O(SO$_2$)NH$_2$, —O—CH(R$_m$)OC(O)R$_n$, —O—CH(R$_m$)OP(O)(OR$_n$)$_2$, —O—P(O)(OR$_n$)$_2$, or

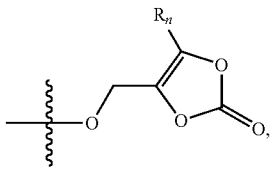

wherein each $R_m$ is independently $C_{1-6}$ alkyl, each $R_n$ is independently $C_{1-12}$ alkyl, $C_{3-8}$ cycloalkyl, or phenyl, each of which is optionally substituted; or $R_2$ and $R'_2$ together may form oxo; and $R_3$ is H or $C_{1-3}$ alkyl.

In some embodiments, the alkali earth metal is sodium.
In other embodiments, the alkali earth metal is potassium.

BRIEF DESCRIPTION OF THE DRAWINGS

The disclosure will now be described, by way of example, with reference to the accompanying drawings, in which.

DETAILED DESCRIPTION OF THE INVENTION

Figure 1:
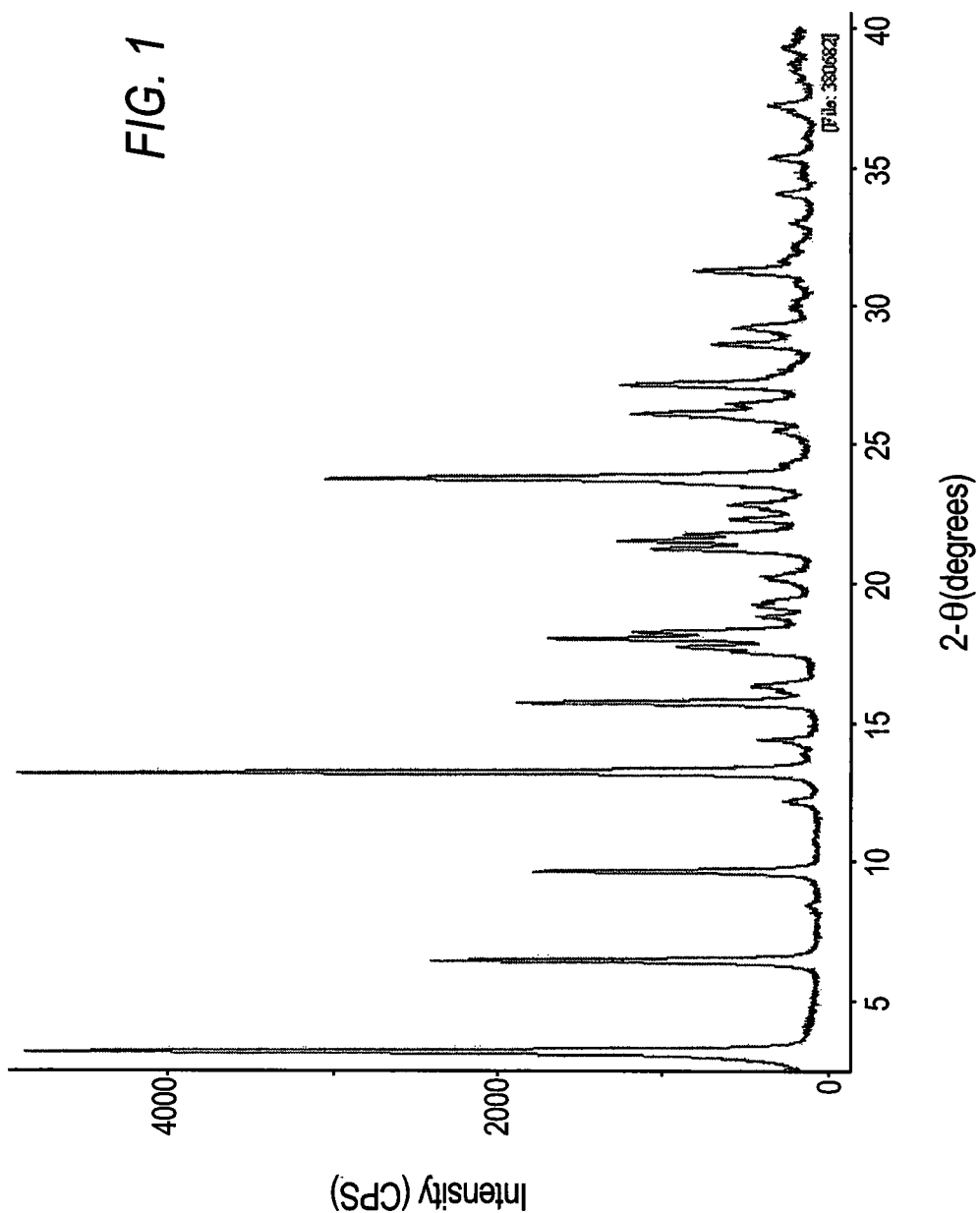
FIG. 1 is the XRPD pattern for a sodium salt of a compound of Formula I.

The present invention provides a salt of a PPARγ-sparing compound, such as a compound of Formula I. Such salts are useful for treating metabolic diseases such as obesity, diabetes, and neurodegenerative disorders.

I. Definitions

As used herein, the following definitions shall apply unless otherwise indicated.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-SO$_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to allyl, isoprenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-SO$_2$—, cycloaliphatic-SO$_2$—, or aryl-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-SO$_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-SO$_2$—, aliphaticamino-SO$_2$—, or cycloaliphatic-SO$_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refer to an amido group such as —N(R$^X$)—C(O)—R$^Y$ or —C(O)—N(R$^X$)$_2$, when used terminally, and —C(O)—N(R$^X$)— or —N(R$^X$)—C(O)— when used internally, wherein R$^X$ and R$^Y$ can be aliphatic, cycloaliphatic, aryl, araliphatic, heterocycloaliphatic, heteroaryl or heteroaraliphatic. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —NR$^X$R$^Y$ wherein each of R$^X$ and R$^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —NR$^X$—. R$^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more C$_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-SO$_2$— or amino-SO$_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

A cycloalkyl or cycloalkenyl group can be optionally substituted with one or more substituents such as phosphor, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-$SO_2$— and aryl-$SO_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phosphor, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic) carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy)heteroaryl; (sulfamoyl)heteroaryl [e.g., (aminosulfonyl)heteroaryl]; (sulfonyl)heteroaryl [e.g., (alkylsulfonyl)heteroaryl]; (hydroxyalkyl)heteroaryl; (alkoxyalkyl)heteroaryl; (hydroxy)heteroaryl; ((carboxy)alkyl)heteroaryl; (((dialkyl)amino)alkyl]heteroaryl; (heterocycloaliphatic)heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl)heteroaryl [e.g., (alkylcarbonyl)heteroaryl]; (alkyl)heteroaryl, and (haloalkyl)heteroaryl [e.g., trihaloalkylheteroaryl].

A "heteroaliphatic (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocycloalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.3.2]decyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—, respectively. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$, wherein R$^X$ and R$^Y$ have been defined above and R$^Z$ can be aliphatic, aryl, araliphatic, heterocycloaliphatic, heteroaryl, or heteroaraliphatic.

As used herein, a "carboxy" group refers to —COOH, —COOR$^X$, —OC(O)H, —OC(O)R$^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfamoyl" group refers to the structure —O—S(O)$_2$—NR$^Y$R$^Z$ wherein R$^Y$ and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidine" group refers to the structure —N=C(N(R$^X$R$^Y$))N(R$^X$R$^Y$) or —NR$^X$—C(=NR$^X$)NR$^X$R$^Y$ wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-12. A branched aliphatic chain is a straight aliphatic chain that is substituted with one or more aliphatic groups. A branched aliphatic chain has the structure —[CQQ]$_v$- where Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables R$_1$, R$_2$, R'$_2$, R$_3$, and R$_4$, and other variables contained in Formula I, described herein, encompass specific groups, such as alkyl and aryl. Unless otherwise noted, each of the specific groups for the variables R$_1$, R$_2$, R'$_2$, R$_3$, and R$_4$, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays, or as therapeutic agents.

As used herein, an "adrenergic agonist" refers to any compound having agonistic activity toward any adrenergic receptor (e.g., $\beta_1$, $\beta_2$, $\beta_3$). Note that the terms "beta-adrenergic" and "β-adrenergic" are used interchangeably. This usage also applies to sub-types of beta agonists, (e.g., 'beta-1-adrenergic agonist' is used interchangeable with 'β1-adrenergic agonist' and/or '$\beta_1$-adrenergic agonist').

As used herein, the term "co-crystal" refers to a substantially crystalline material having two or more distinct molecular components (e.g., a compound of formula I or a salt thereof and a phosphodiesterase inhibitor) within the crystal lattice.

Chemical structures and nomenclature are derived from ChemDraw, version 11.0.1, Cambridge, Mass.

II. Salts

Salts of the present invention comprising a thiazolidinedione compound (e.g., a compound of Formula I) are uniquely effective in treating or preventing metabolic diseases such as obesity (e.g., central obesity), diabetes, and/or neurodegenerative diseases (e.g., Alzheimer's Disease, dementia, or the like) in a patient, and these salts possess a reduced interaction with PPARγ. Accordingly, these compound salts demonstrate reduced side effects related to PPARγ interaction than PPARγ activating compounds.

A. Compounds of Formula I

The present invention provides a salt of a compound of Formula I:

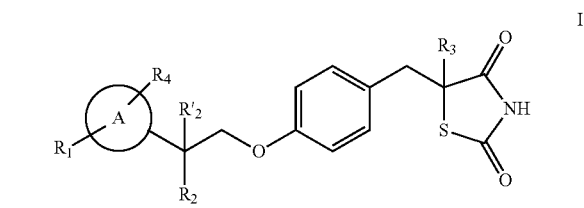

or a pharmaceutically acceptable salt thereof, wherein:

Each of $R_1$ and $R_4$ is independently selected from H, halo, aliphatic, and alkoxy, wherein the aliphatic or alkoxy is optionally substituted with 1-3 of halo;

$R'_2$ is H, and $R_2$ is H, halo, hydroxy, or optionally substituted aliphatic, —O-acyl, —O-aroyl, —O-heteroaroyl, —O(SO$_2$)NH$_2$, —O—CH($R_m$)OC(O)$R_n$, —O—CH($R_m$)OP(O)(OR$_n$)$_2$, —O—P(O)(OR$_n$)$_2$, or

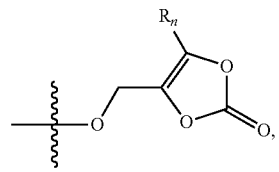

wherein each $R_m$ is independently $C_{1-6}$ alkyl, each $R_n$ is independently $C_{1-12}$ alkyl, $C_{3-8}$ cycloalkyl, or phenyl, each of which is optionally substituted; or $R_2$ and $R'_2$ together may form oxo;

$R_3$ is H or $C_{1-3}$ alkyl; and

Ring A is phenyl, pyridin-2-yl, pyridin-3-yl or pyridin-4-yl, each of which is substituted with an $R_1$ group and an $R_4$ group at any chemically feasible position on ring A.

In one aspect, the present invention provides a hydrogen chloride salt of a compound of Formula I:

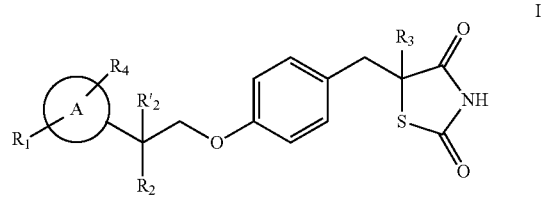

wherein:

Each of $R_1$ and $R_4$ is independently selected from H, halo, aliphatic, and alkoxy, wherein the aliphatic or alkoxy is optionally substituted with 1-3 of halo;

$R'_2$ is H and $R_2$ is H, halo, hydroxy, or optionally substituted aliphatic, —O-acyl, —O-aroyl, —O-heteroaroyl, —O(SO$_2$)NH$_2$, —O—CH($R_m$)OC(O)$R_n$, —O—CH($R_m$)OP(O)(OR$_n$)$_2$, —O—P(O)(OR$_n$)$_2$, or

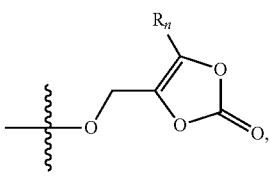

wherein each $R_m$ is independently $C_{1-6}$ alkyl, each $R_n$ is independently $C_{1-12}$ alkyl, $C_{3-8}$ cycloalkyl, or phenyl, each of which is optionally substituted; or $R_2$ and $R'_2$ together may form oxo;

$R_3$ is H or $C_{1-3}$ alkyl; and

Ring A is phenyl, pyridin-2-yl, pyridin-3-yl or pyridin-4-yl, each of which is substituted with an $R_1$ group and an $R_4$ group at any chemically feasible position on ring A.

Another aspect of the present invention provides a dihydrogen sulfate salt of a compound of Formula I:

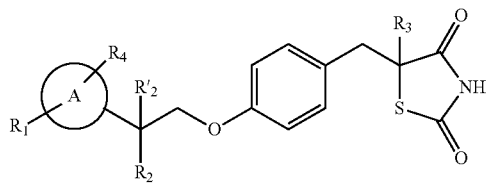

wherein:

Each of $R_1$ and $R_4$ is independently selected from H, halo, aliphatic, and alkoxy, wherein the aliphatic or alkoxy is optionally substituted with 1-3 of halo;

$R'_2$ is H and $R_2$ is H, halo, hydroxy, or optionally substituted aliphatic, —O-acyl, —O-aroyl, —O-heteroaroyl, —O(SO$_2$)NH$_2$, —O—CH(R$_m$)OC(O)R$_n$, —O—CH(R$_m$)OP(O)(OR$_n$)$_2$, —O—P(O)(OR$_a$)$_2$, or

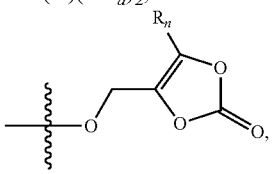

wherein each $R_m$ is independently $C_{1-6}$ alkyl, each is independently $C_{1-12}$ alkyl, $C_{3-8}$ cycloalkyl, or phenyl, each of which is optionally substituted; or $R_2$ and $R'_2$ together may form oxo;

$R_3$ is H or $C_{1-3}$ alkyl; and

Ring A is phenyl, pyridin-2-yl, pyridin-3-yl or pyridin-4-yl, each of which is substituted with an $R_1$ group and an $R_4$ group at any chemically feasible position on ring A.

Another aspect of the present invention provides an alkali earth metal salt of a compound of Formula I:

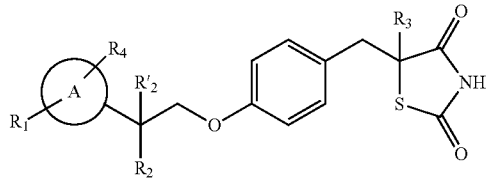

wherein:

Each of $R_1$ and $R_4$ is independently selected from H, halo, aliphatic, and alkoxy, wherein the aliphatic or alkoxy is optionally substituted with 1-3 of halo;

$R'_2$ is H and $R_2$ is H, halo, hydroxy, or optionally substituted aliphatic, —O-acyl, —O-aroyl, —O-heteroaroyl, —O(SO$_2$)NH$_2$, —O—CH(R$_m$)OC(O)R$_n$, —O—CH(R$_m$)OP(O)(OR$_n$)$_2$, —O—P(O)(OR$_n$)$_2$, or

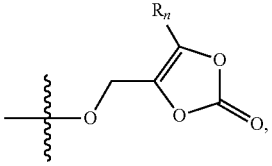

wherein each $R_m$ is independently $C_{1-6}$ alkyl, each $R_n$ is independently $C_{1-12}$ alkyl, $C_{3-8}$ cycloalkyl, or phenyl, each of which is optionally substituted; or $R_2$ and $R'_2$ together may form oxo;

$R_3$ is H or $C_{1-3}$ alkyl; and

Ring A is phenyl, pyridin-2-yl, pyridin-3-yl or pyridin-4-yl, each of which is substituted with an $R_1$ group and an $R_4$ group at any chemically feasible position on ring A.

In several embodiments, the alkali earth metal is potassium; and in other embodiments, the alkali earth metal is sodium.

In several embodiments, $R_1$ is H. In some embodiments, $R_1$ is halo, such as F or Cl. In some embodiments, $R_1$ is an aliphatic optionally substituted with 1-3 halo. For instance, $R_1$ is trifluoromethyl. In some embodiments, $R_1$ is alkoxy. For instance, $R_1$ is methoxy, ethoxy, or —O-isopropyl. In still other embodiments, $R_1$ is alkoxy substituted with 1-3 halo. For instance, $R_1$ is —OCHF$_2$ or —OCF$_3$. In each of the foregoing embodiments, $R_1$ can be substituted at the ortho, meta, or para position of ring A. In certain embodiments, $R_1$ is substituted at the para or meta position of ring A.

In several embodiments, $R_4$ is H. In some embodiments, $R_4$ is halo, such as F or Cl. In some embodiments, $R_4$ is an aliphatic optionally substituted with 1-3 halo. For instance, $R_4$ is trifluoromethyl. In some embodiments $R_4$ is alkoxy. For instance, $R_4$ is methoxy, ethoxy, or —O-isopropyl. In still other embodiments, $R_4$ is alkoxy substituted with 1-3 halo. For instance, $R_4$ is —OCHF$_2$ or —OCF$_3$. In each of the foregoing embodiments, $R_4$ can be substituted at the ortho, meta, or para position of ring A. In certain embodiments, $R_4$ is substituted at the para or meta position of ring A. In some embodiments, $R_1$ and $R_4$ are different substituents. In still other embodiments, $R_1$ and $R_4$ are the same substituent. In some embodiments when $R_1$ is aliphatic, $R_4$ is other than H.

In several embodiments, each of $R_1$ and $R_4$ is independently selected from H, halo, aliphatic, and alkoxy, wherein the aliphatic and alkoxy are optionally substituted with 1-3 of halo.

In several embodiments, each of $R_1$ and $R_4$ is independently selected from H, halo, aliphatic, and alkoxy, wherein the aliphatic and alkoxy are optionally substituted with 1-3 of halo.

In several embodiments, $R_2$ is halo, hydroxy, aliphatic, —O-acyl, —O-aroyl, —O-heteroaroyl, —O(SO$_2$)NH$_2$, —O—CH(R$_m$)OC(O)R$_n$, —O—CH(R$_m$)OP(O)(OR$_n$)$_2$, —O—P(O)(OR$_n$)$_2$, or

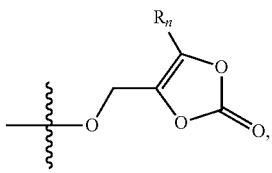

wherein each $R_m$ is $C_{1-6}$ alkyl, $R_n$ is $C_{1-12}$ alkyl, $C_{3-8}$ cycloalkyl, or phenyl and each substituent $R_m$ or $R_n$ is optionally substituted.

In some embodiments, $R_2$ is H.
In some embodiments, $R_2$ is hydroxy.
In some embodiments, $R_2$ is an optionally substituted straight or branched $C_{1-6}$ alkyl, an optionally substituted straight or branched $C_{2-6}$ alkenyl, or an optionally substituted straight or branched $C_{2-6}$ alkynyl. In other embodiments, $R_2$ is a $C_{1-6}$ aliphatic optionally substituted with 1-2 hydroxy, carboxy or halo. In other embodiments, $R_2$ is a $C_{1-6}$ alkyl optionally substituted with hydroxy. In further embodiments, $R_2$ is a $C_{1-6}$ alkyl optionally substituted with —O-acyl, —O-aroyl, —O-heteroaroyl. In several other embodiments, $R_2$ is a methyl, ethyl, propyl, isopropyl, butyl, tert-butyl, pentyl, or hexyl, each of which is optionally substituted with hydroxy. In several additional embodiments, $R_2$ is methyl or ethyl, each of which is substituted with hydroxy.

In certain embodiments, $R_2$ is —O-acyl, —O-aroyl, or —O-heteroaroyl.

In other embodiments, $R_2$ is —O-acetyl, —O-hexanoyl, —O-benzoyl, —O-pivaloyl, —O-imidazolyl, —O-succinoyl, —O-thiazoloyl or —O-pyridinoyl, each optionally substituted.

In some embodiments, $R_2$ is —O—C(O)-imidazol-1-yl.
In certain embodiments, $R_2$ is —O—CH($R_m$)—O—C(O)—$R_n$.
In some embodiments, $R_2$ is —O—CH($R_m$)OP(O)(O$R_n$)$_2$.
In some embodiments, $R_2$ is —O—P(O)(O$R_n$)$_2$.
In other embodiments, $R_2$ is —O—S(O$_2$)NH$_2$.
In some further embodiments, $R_2$ is a 1,3-dioxolan-2-one of the Formula

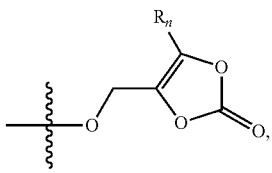

wherein $R_m$ and $R_n$ are as previously described.

In several embodiments, $R'_2$ is H.
In some embodiments, $R_2$ and $R'_2$ together form oxo.
In some embodiments, $R'_2$ is H and $R_2$ has an R configuration.
In some embodiments, $R'_2$ is H and $R_2$ has an S configuration.
In some embodiments, $R'_2$ is H and $R_2$ is racemic.
In further embodiments, ring A is phenyl or pyridinyl.
In some embodiments, ring A is pyridin-2-yl.
In some embodiments, ring A is pyridin-3-yl.
In some embodiments, ring A is pyridin-4-yl.
In other embodiments, $R_3$ is H or optionally substituted $C_{1-3}$ alkyl.
In some embodiments, $R_3$ is H.
In some embodiments, $R_3$ is CH$_3$.

Another aspect of the present invention provides a salt (e.g., a hydrogen chloride salt, a dihydrogen sulfate salt, or an alkali earth metal salt) of a compound of Formula II, IIA, or IIB:

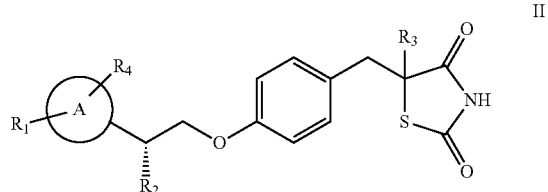

II

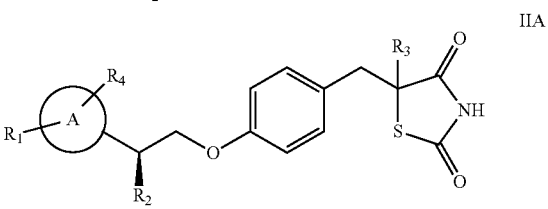

IIA

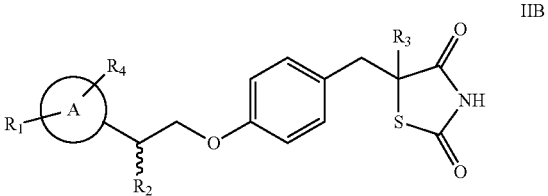

IIB

In another aspect, the invention provides a salt (e.g., a hydrogen chloride salt, a dihydrogen sulfate salt, or an alkali earth metal salt) of a compound of Formula III:

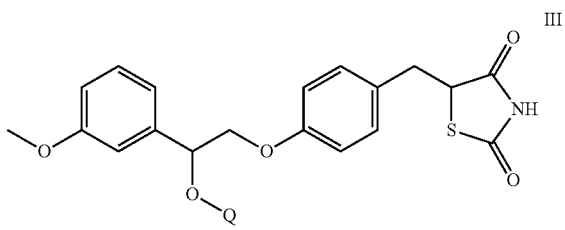

III wherein Q is acyl, aroyl, heteroaroyl, —SO$_2$NH$_2$, —CH($R_m$)OC(O)$R_n$, —CH($R_m$)OP(O)(O$R_n$)$_2$, —P(O)(O$R_n$)$_2$, or

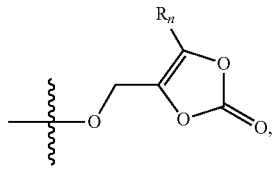

wherein each $R_m$ is $C_{1-6}$ alkyl, $R_n$ is $C_{1-12}$ alkyl, $C_{3-8}$ cycloalkyl, or phenyl, wherein each substituent is optionally substituted.

In some embodiments, Q in Formula III is acyl.
In some embodiments, Q in Formula III is -acetyl, -hexanoyl, -benzoyl, -pivaloyl, -succinoyl, each optionally substituted.
In certain embodiments, Q in Formula III is acetyl.
In certain embodiments, Q in Formula III is hexanoyl.
In certain embodiments, Q in Formula III is benzoyl.

In certain embodiments, Q in Formula III is pivaloyl.
In certain embodiments, Q in Formula III is succinoyl.
In another aspect, the invention provides a salt (e.g., a hydrogen chloride salt, a dihydrogen sulfate salt, or an alkali earth metal salt) of a compound of Formula IIIA or IIIB:

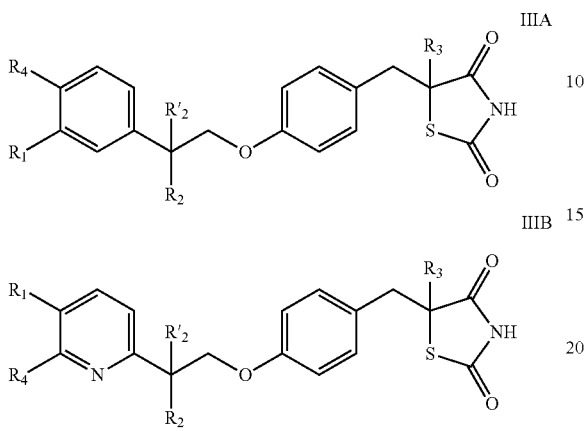

IIIA

IIIB wherein $R_1$, $R_2$, $R'_2$, and $R_4$ are defined above in Formula I, and $R_3$ is hydrogen.

In some embodiments of this aspect, $R_2$ and $R'_2$ together form oxo.

In some embodiments, the salt is a sodium salt of a compound of Formula IIIA or IIIB. In some embodiments, the salt is a potassium salt of a compound of Formula IIIA or IIIB.

In another aspect, the invention provides a salt (e.g., a hydrogen chloride salt, a dihydrogen sulfate salt, or an alkali earth metal salt) of a compound of Formula IVA or IVB:

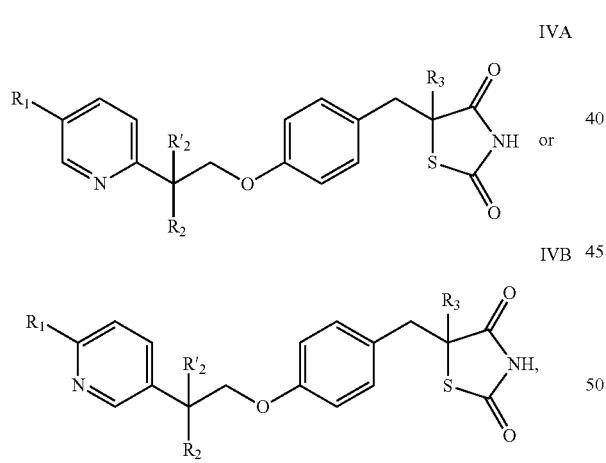

IVA

IVB wherein $R'_2$ is H, $R_2$ is H, —OH, —O-acyl, —O-aroyl or —O-heteroaryoyl; or $R_2$ and $R'_2$ together form oxo; $R_1$ is defined above for Formula I; and $R_3$ is hydrogen.

In further embodiments, Q in formula IVA or IVB is H, —O-acetyl, —O-hexanoyl, —O-benzoyl, —O-pivaloyl, —O-succinoyl, each optionally substituted.

In some embodiments, Q in Formula IVA or IVB is H.
In certain embodiments, Q in Formula IVA or IVB is —O-acetyl.
In certain embodiments, Q in Formula IVA or IVB is —O-hexanoyl.
In certain embodiments, Q in Formula IVA or IVB is —O-benzoyl.
In certain embodiments, Q in Formula IVA or IVB is —O-pivaloyl.
In certain embodiments, Q in formula IVA or IVB is —O-succinoyl.

Several exemplary compounds of Formula I are provided below in Tables A-L.

TABLE A

Exemplary compounds wherein $R_2$ and $R'_2$ form oxo.

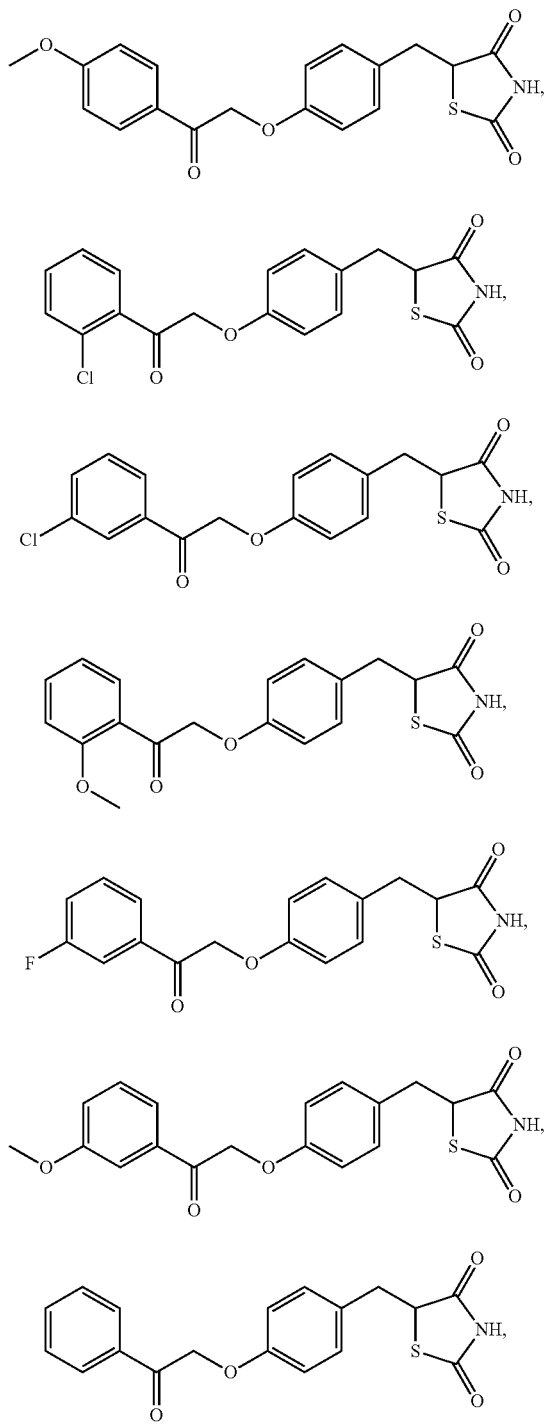

TABLE A-continued
Exemplary compounds wherein $R_2$ and $R'_2$ form oxo.
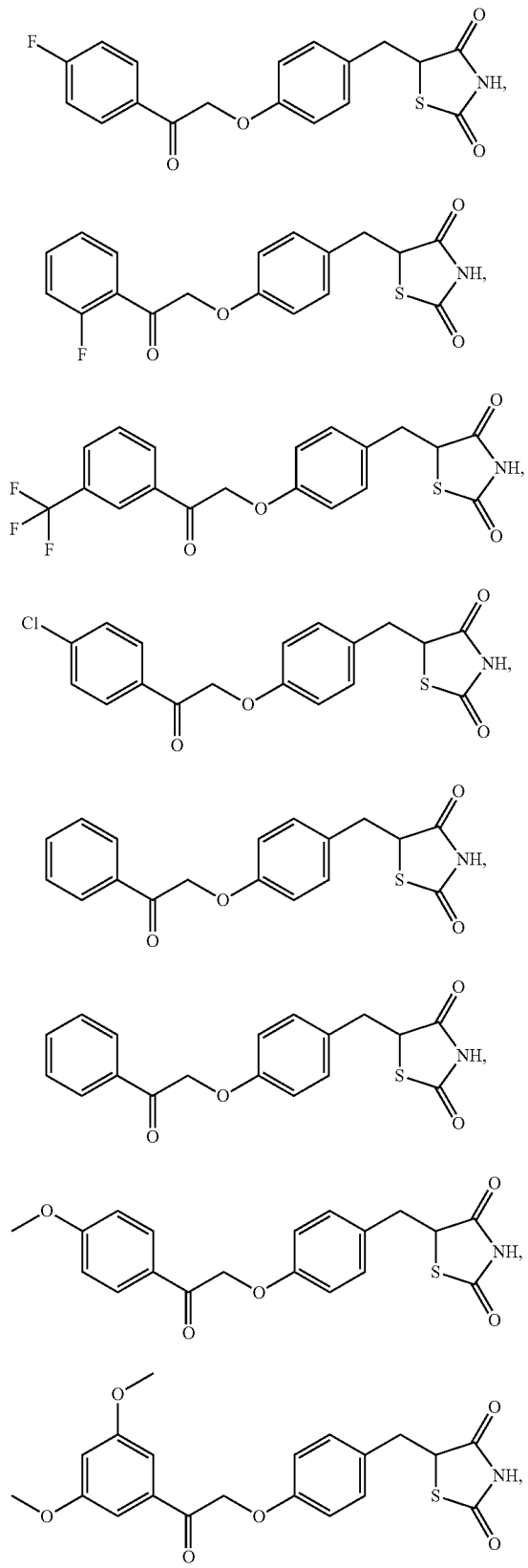
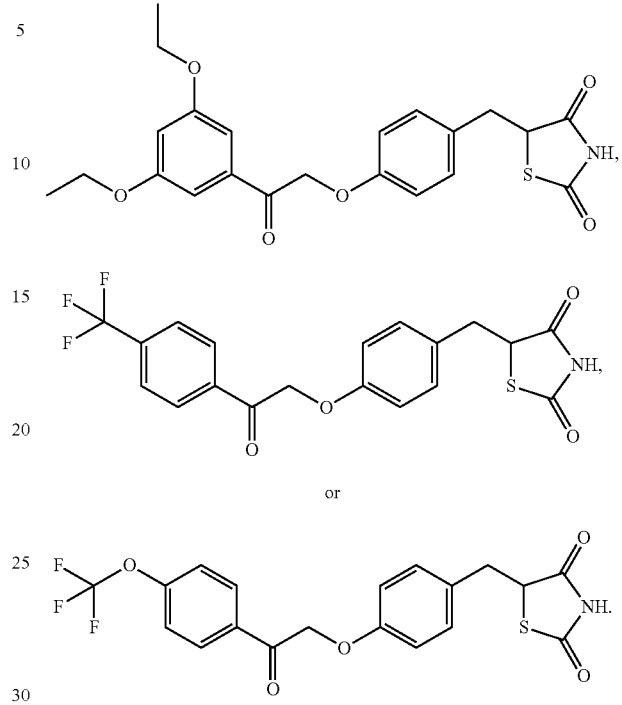
TABLE B
Exemplary compounds wherein and ring A is phenyl, $R_2$ is —OH having an (R) configuration and $R'_2$ is H.
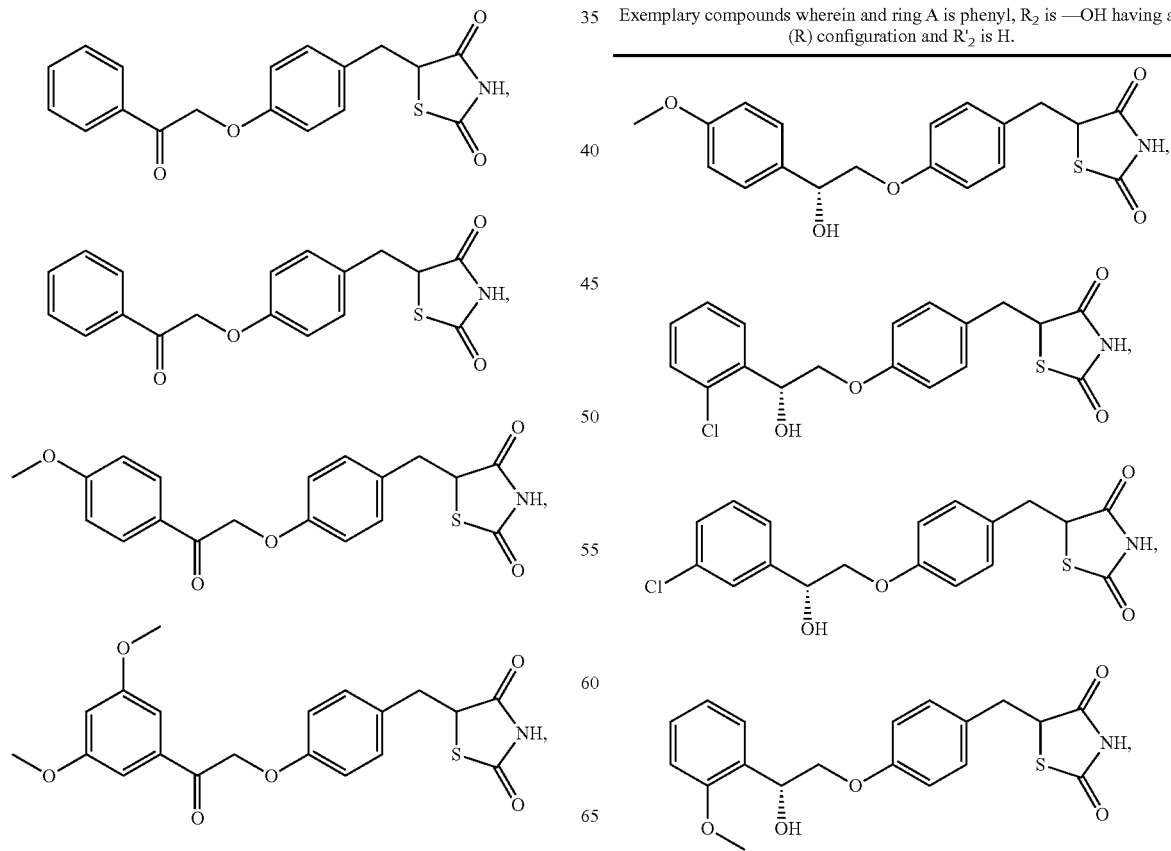

TABLE B-continued
Exemplary compounds wherein and ring A is phenyl, R$_2$ is —OH having an (R) configuration and R'$_2$ is H.
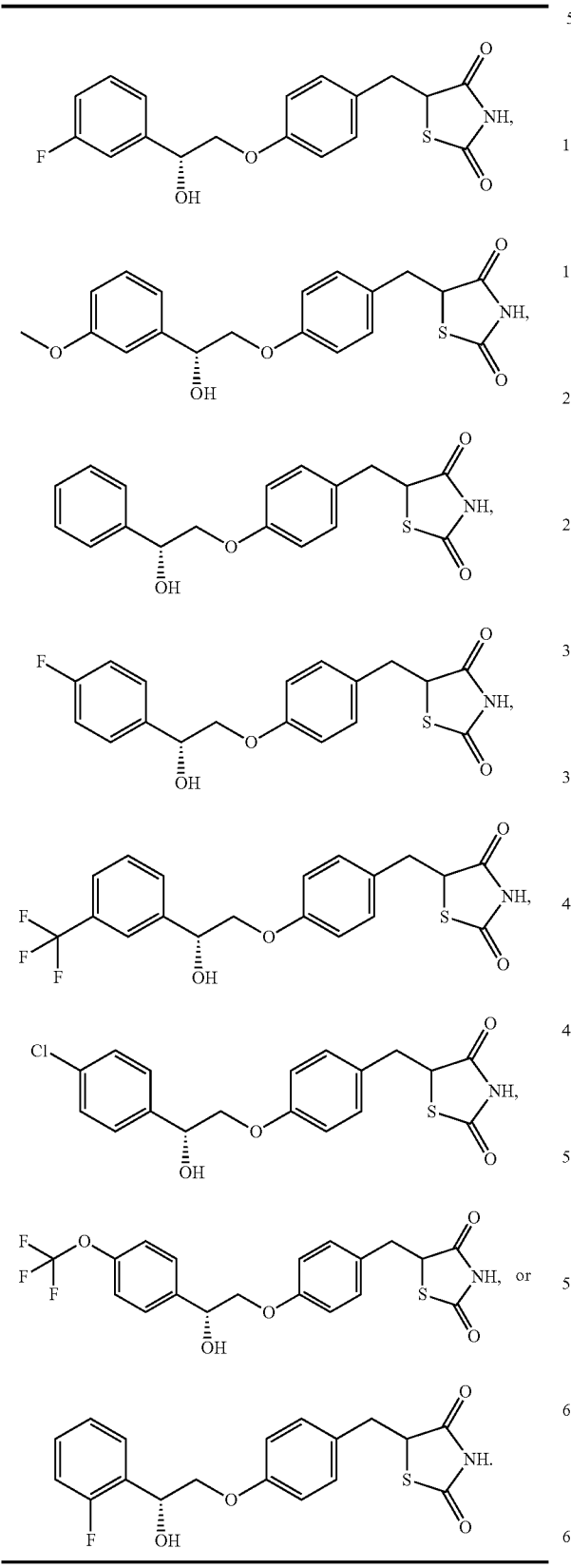
TABLE C
Exemplary compounds wherein R$_2$ is OH having an (S) configuration and R'$_2$ is H.
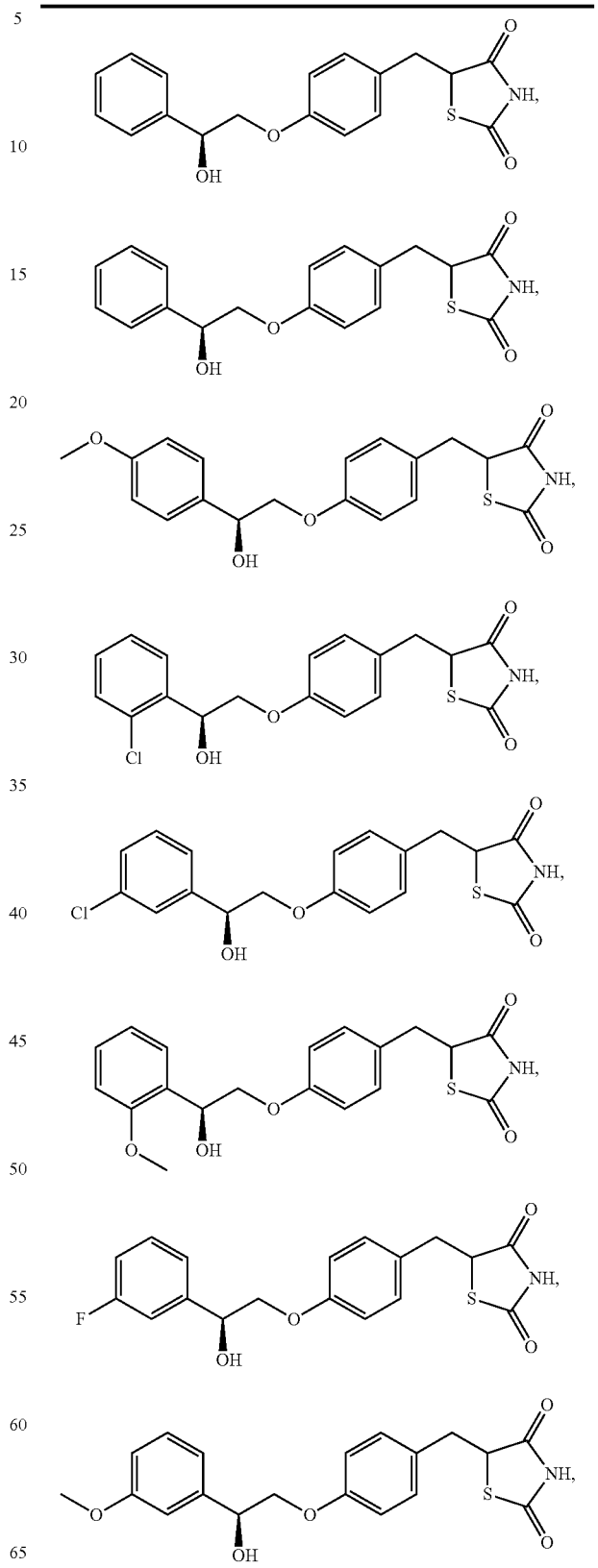

TABLE C-continued
Exemplary compounds wherein R₂ is OH having an (S) configuration and R'₂ is H.
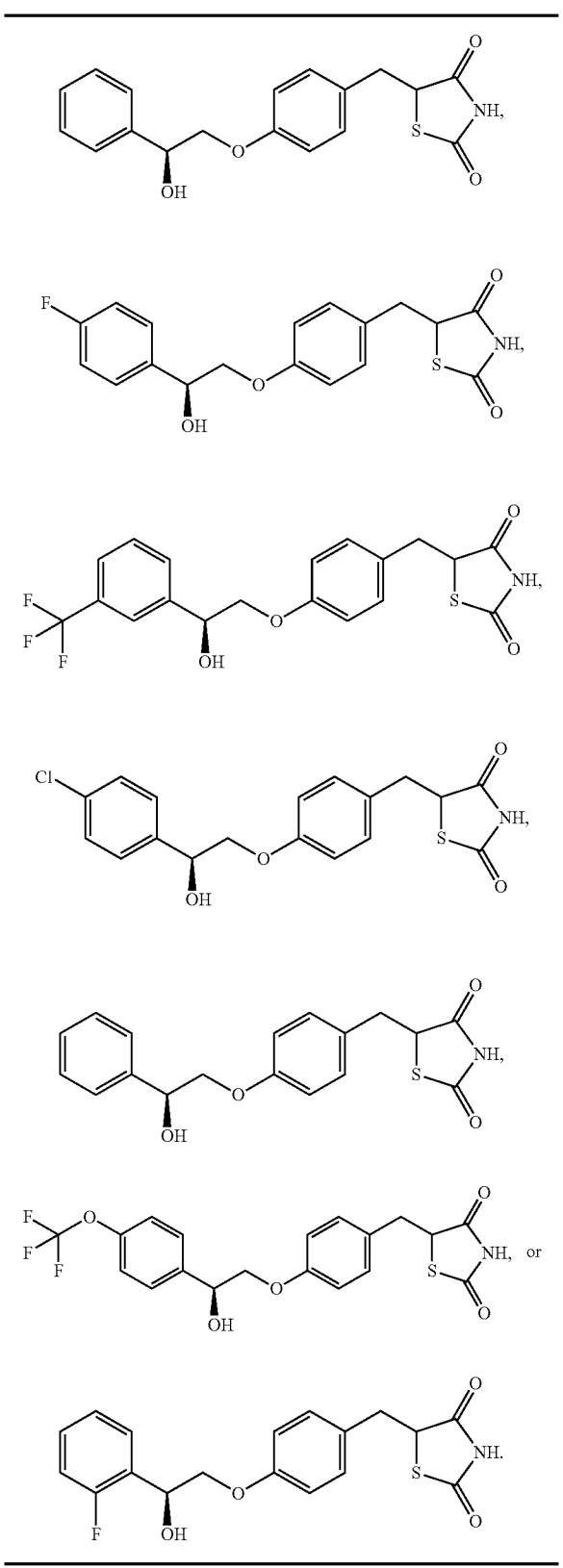
TABLE D
Exemplary compounds wherein R₂ is racemic —OH and R'₂ is H.
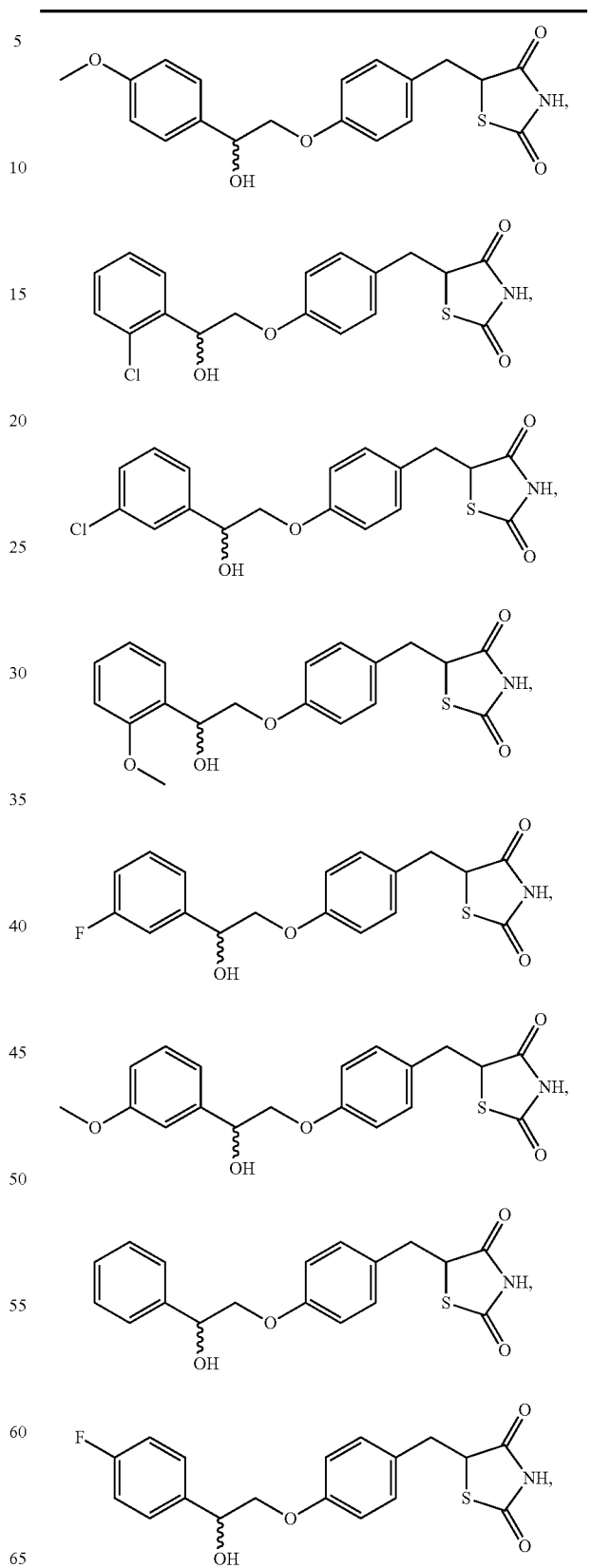

TABLE D-continued
Exemplary compounds wherein R₂ is racemic —OH and R'₂ is H.
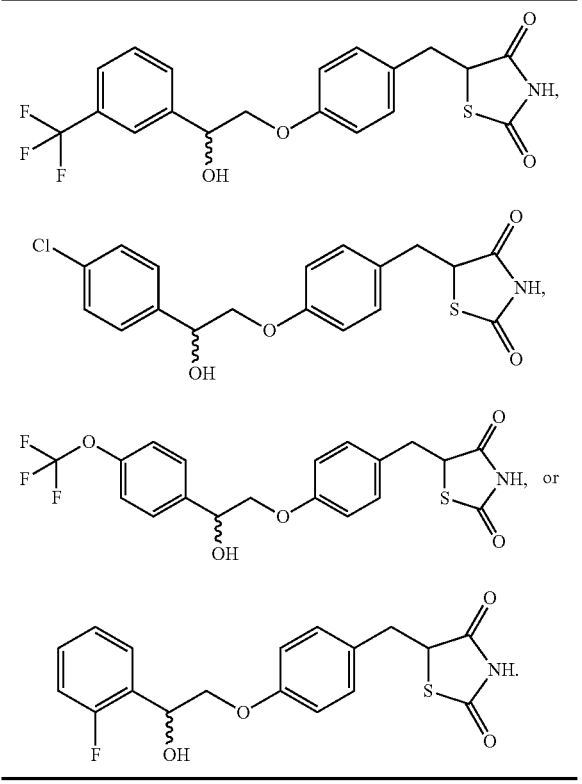
TABLE E
Exemplary compounds wherein R₂ is —O-Acyl, —O-Aroyl, or —O-heteroyl, and R'₂ is H.
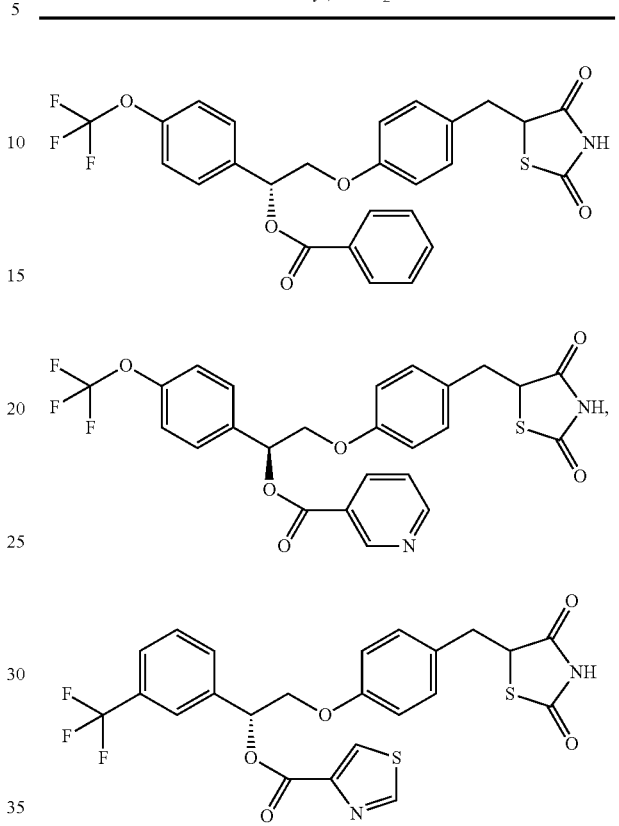
TABLE E-continued
Exemplary compounds wherein R₂ is —O-Acyl, —O-Aroyl, or —O-heteroyl, and R'₂ is H.
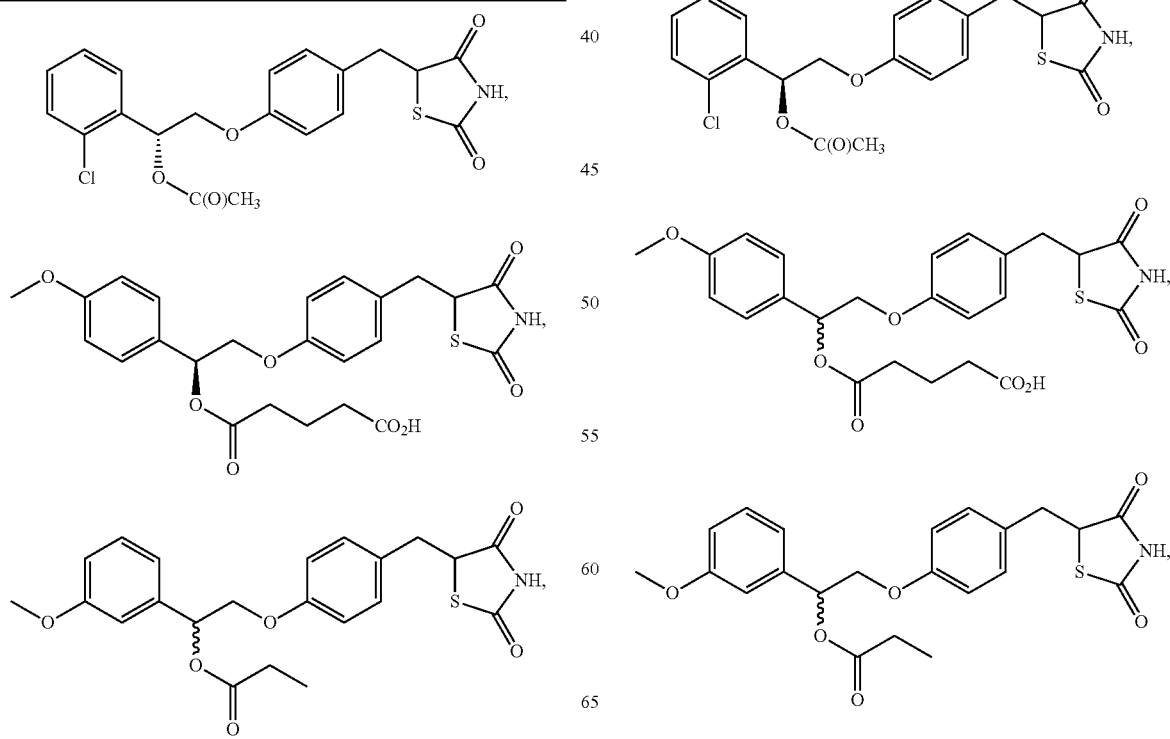

TABLE E-continued
Exemplary compounds wherein R₂ is —O-Acyl, —O-Aroyl, or —O-heteroyl, and R'₂ is H.
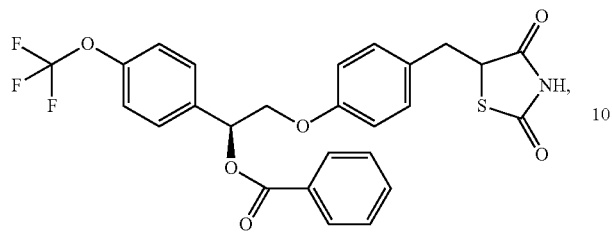
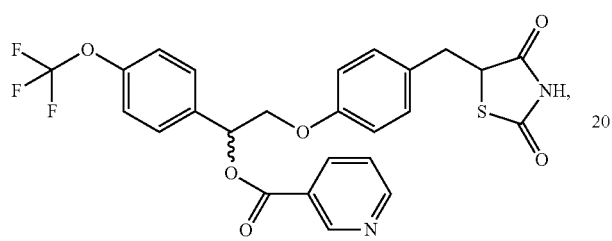
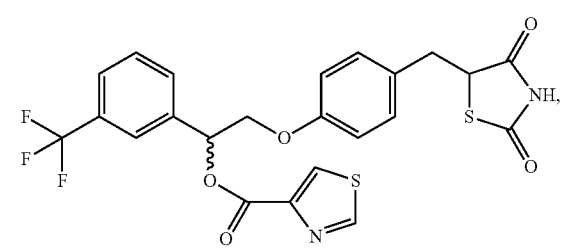 [SMILES: O=C1NC(=O)C(Cc2ccc(OCC(OC(=O)c3cscn3)c3cccc(C(F)(F)F)c3)cc2)S1]
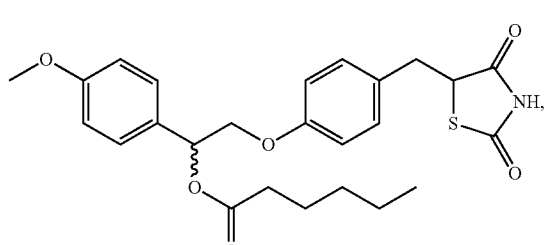
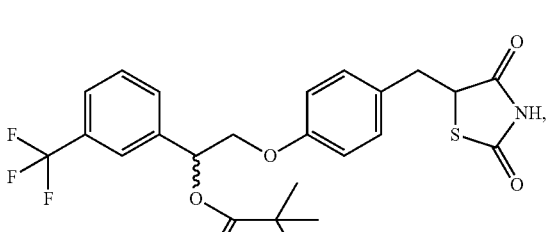
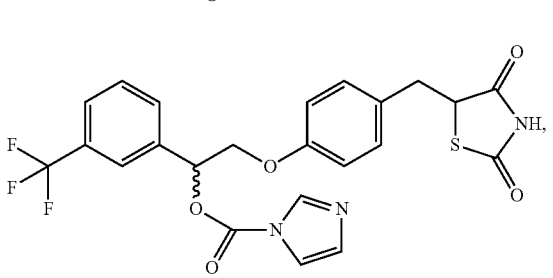
TABLE E-continued
Exemplary compounds wherein R₂ is —O-Acyl, —O-Aroyl, or —O-heteroyl, and R'₂ is H.
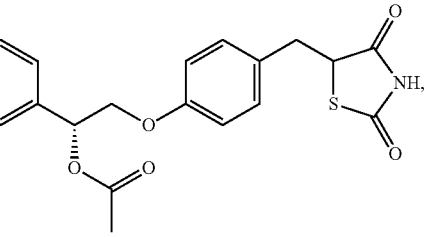
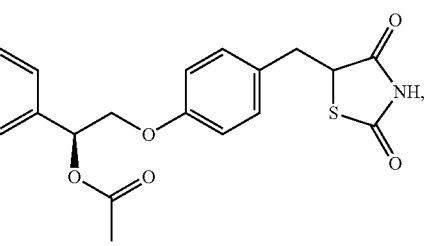
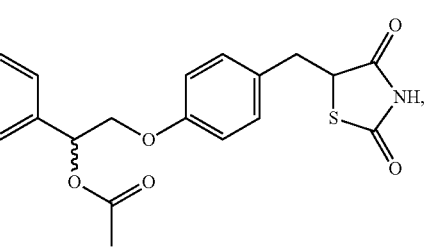
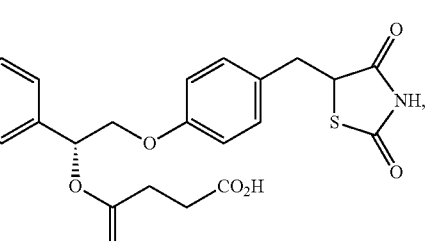
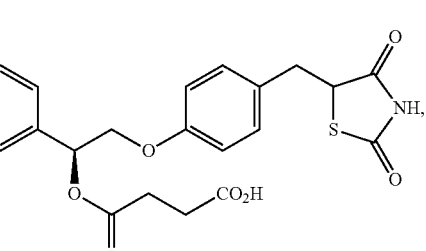
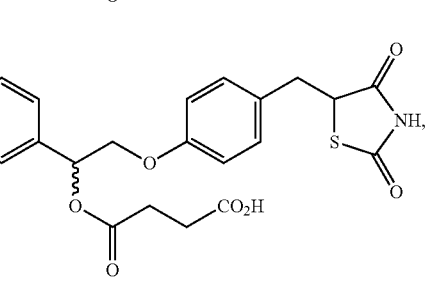

TABLE E-continued
Exemplary compounds wherein $R_2$ is —O-Acyl, —O-Aroyl, or —O-heteroyl, and $R'_2$ is H.
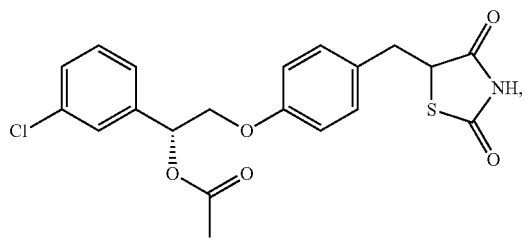 [SMILES: CC(=O)O[C@@H](COc1ccc(CC2SC(=O)NC2=O)cc1)c1cccc(Cl)c1]
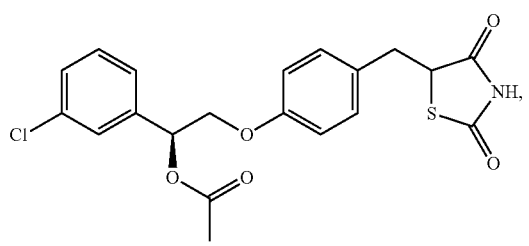 [SMILES: CC(=O)O[C@H](COc1ccc(CC2SC(=O)NC2=O)cc1)c1cccc(Cl)c1]
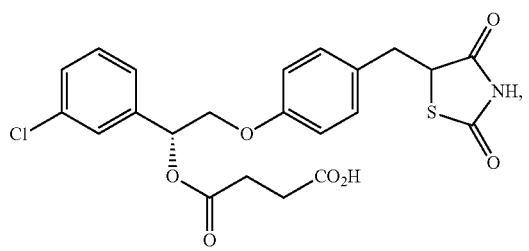 [SMILES: O=C(O)CCC(=O)O[C@@H](COc1ccc(CC2SC(=O)NC2=O)cc1)c1cccc(Cl)c1]
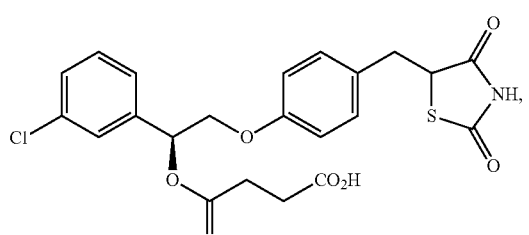
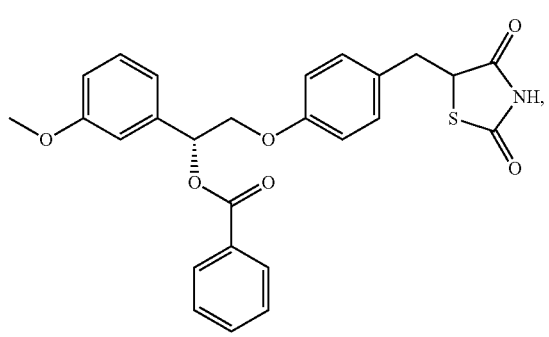 [SMILES: COc1cccc(C(COc2ccc(CC3SC(=O)NC3=O)cc2)OC(=O)c2ccccc2)c1]
TABLE E-continued
Exemplary compounds wherein $R_2$ is —O-Acyl, —O-Aroyl, or —O-heteroyl, and $R'_2$ is H.
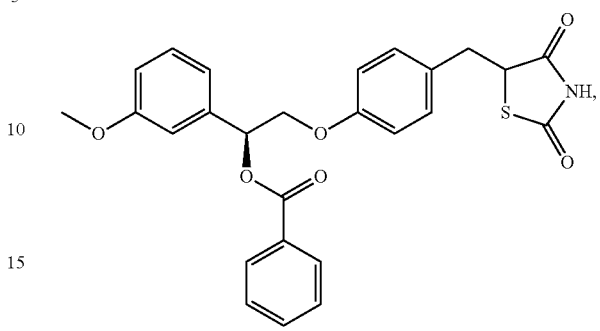
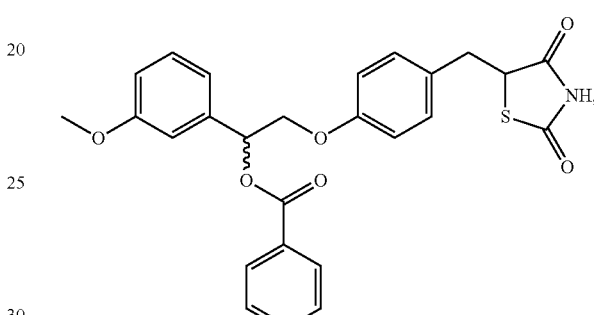
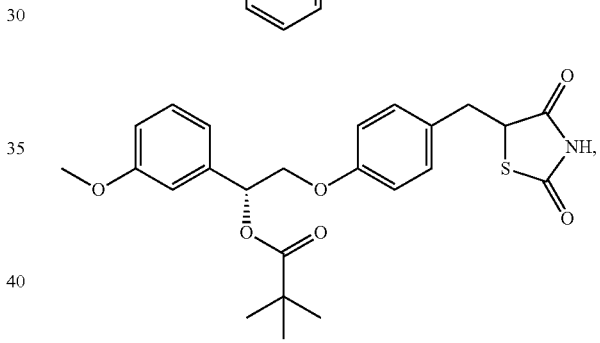
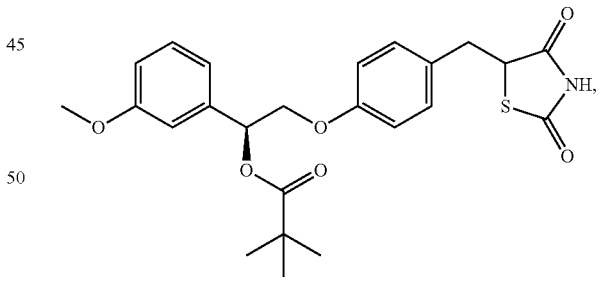
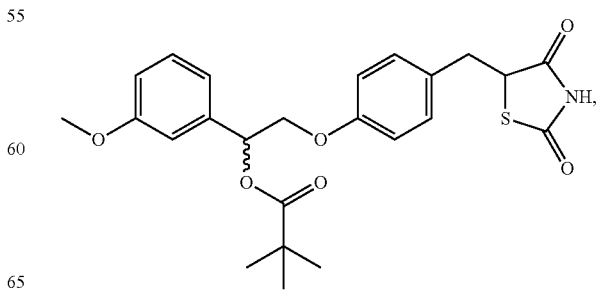

TABLE E-continued
Exemplary compounds wherein R$_2$ is —O-Acyl, —O-Aroyl, or —O-heteroyl, and R'$_2$ is H.
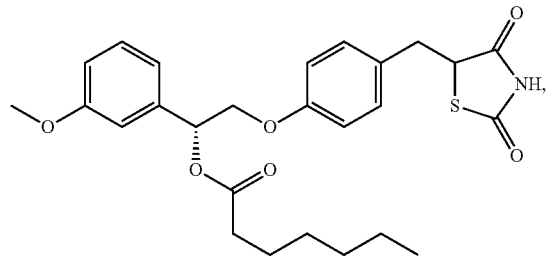 [SMILES: CCCCCCC(=O)O[C@@H](COc1ccc(CC2SC(=O)NC2=O)cc1)c1cccc(OC)c1]
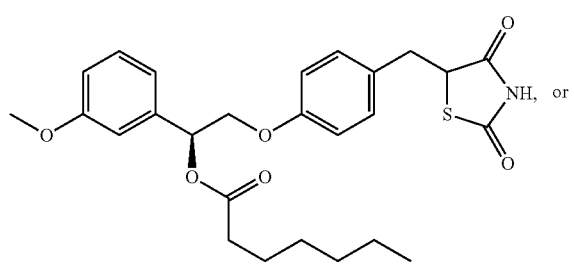 [SMILES: CCCCCCC(=O)O[C@H](COc1ccc(CC2SC(=O)NC2=O)cc1)c1cccc(OC)c1 ; "or"]  or
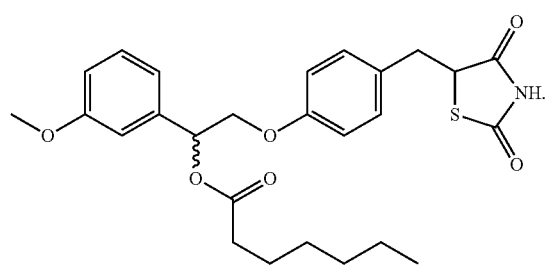 [SMILES: CCCCCCC(=O)OC(COc1ccc(CC2SC(=O)NC2=O)cc1)c1cccc(OC)c1]
TABLE F
Exemplary compounds wherein R$_2$ is —O—CH(R$_m$)—O—C(O)R$_n$ and R'$_2$ is H.
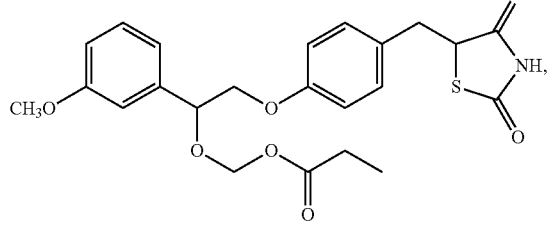
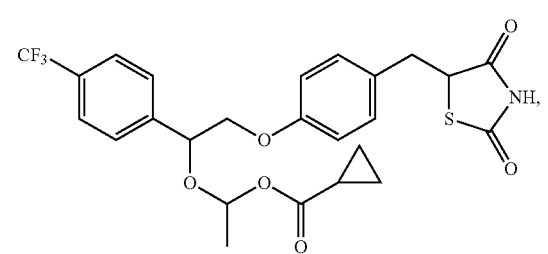 [SMILES: CC(OC(=O)C1CC1)OC(COc1ccc(CC2SC(=O)NC2=O)cc1)c1ccc(C(F)(F)F)cc1]
TABLE F-continued
Exemplary compounds wherein R$_2$ is —O—CH(R$_m$)—O—C(O)R$_n$ and R'$_2$ is H.
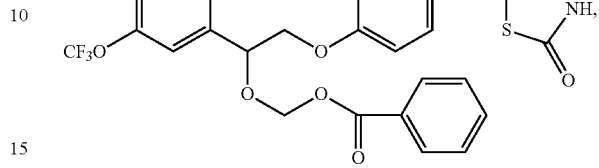
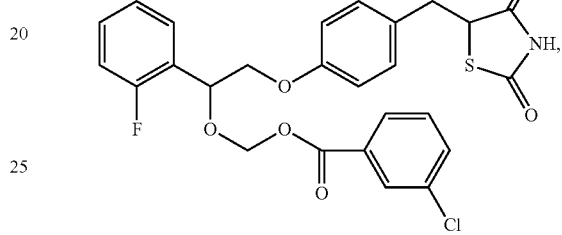
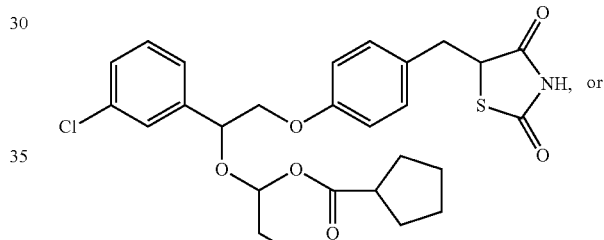  or
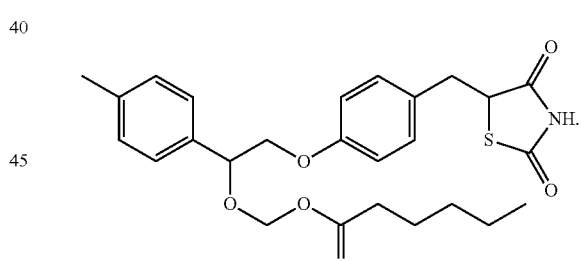
TABLE G
Exemplary compounds wherein R$_2$ is —O—CH(R$_m$)OP(O)(OR$_n$)$_2$ and R'$_2$ is H.
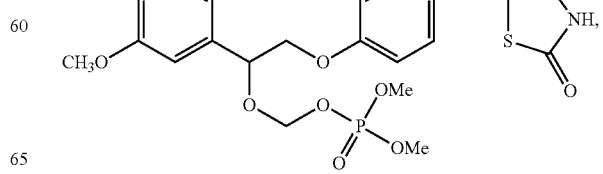

TABLE G-continued
Exemplary compounds wherein $R_2$ is —O—CH($R_m$)OP(O)(O$R_n$)$_2$ and $R'_2$ is H.
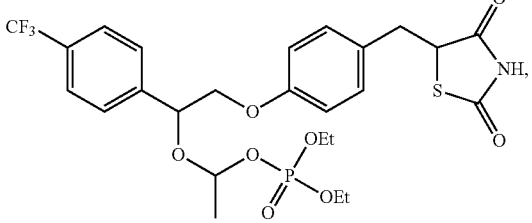
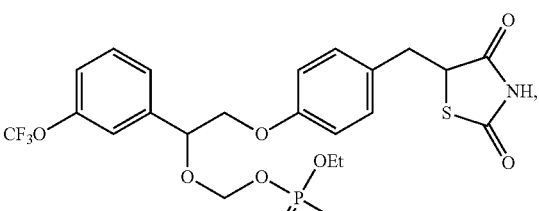
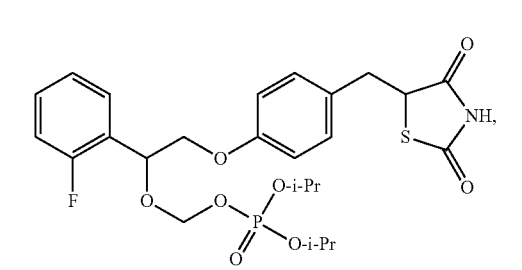
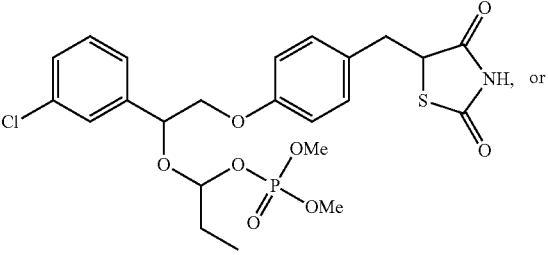 [SMILES: CCC(OC(COc1ccc(CC2SC(=O)NC2=O)cc1)c1cccc(Cl)c1)OP(=O)(OC)OC ; "or"]
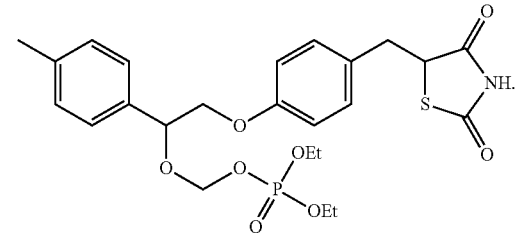 [SMILES: CCOP(=O)(OCC)OCOC(COc1ccc(CC2SC(=O)NC2=O)cc1)c1ccc(C)cc1]
TABLE H
Exemplary compounds wherein $R_2$ is —O—P(O)(O$R_n$)$_2$ and $R'_2$ is H.
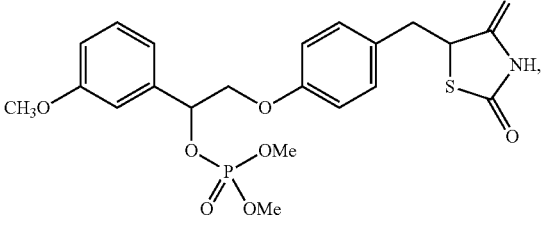
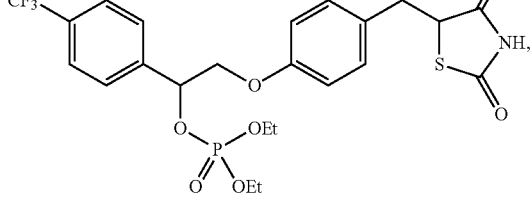
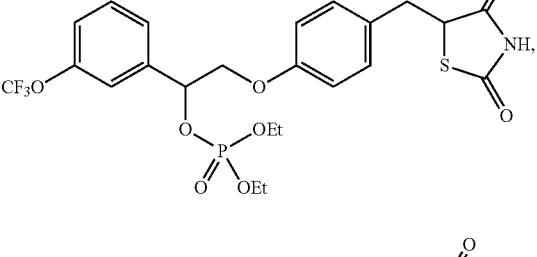
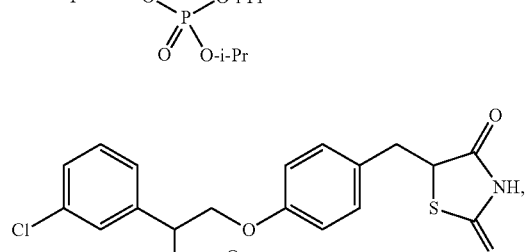
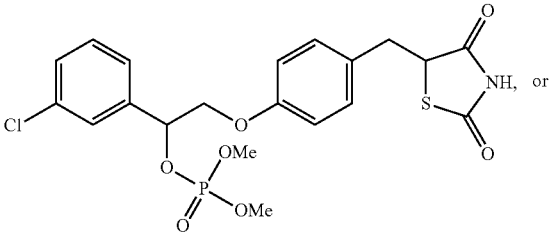 [SMILES: COP(=O)(OC)OC(COc1ccc(CC2SC(=O)NC2=O)cc1)c1cccc(Cl)c1 ; "or"]

TABLE H-continued

Exemplary compounds wherein R₂ is —O—P(O)(OR$_n$)₂ and R'₂ is H.

TABLE I

Exemplary compounds wherein R₂ is —O—SO₂NH₂ and R'₂ is H.

TABLE I-continued

Exemplary compounds wherein R₂ is —O—SO₂NH₂ and R'₂ is H.

TABLE J

Exemplary compounds wherein R₂ is and R'₂ is H.

TABLE J-continued
Exemplary compounds wherein R$_2$ is
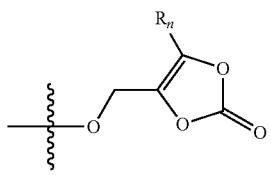
and R'$_2$ is H.
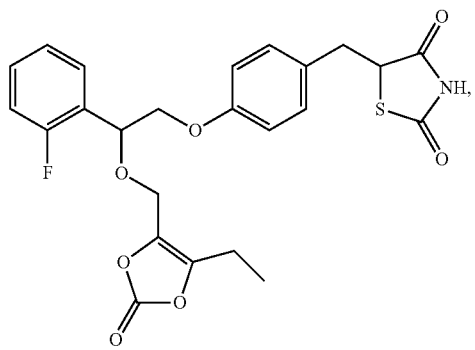 [SMILES: CCc1oc(=O)oc1COC(COc1ccc(CC2SC(=O)NC2=O)cc1)c1ccccc1F]
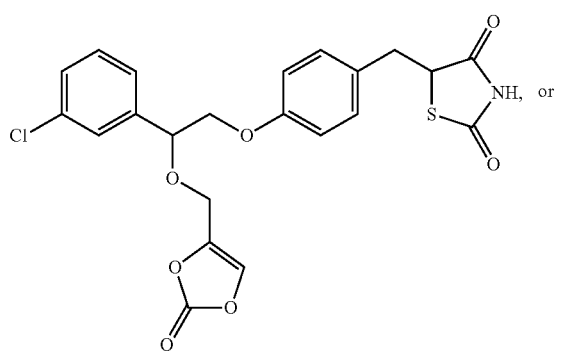 [SMILES: O=C1NC(=O)C(Cc2ccc(OCC(OCc3coc(=O)o3)c3cccc(Cl)c3)cc2)S1 ; "or"]
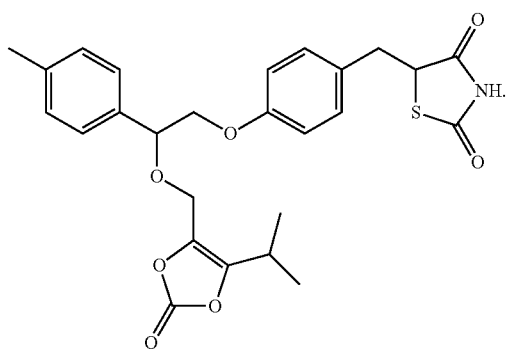 [SMILES: Cc1ccc(C(COc2ccc(CC3SC(=O)NC3=O)cc2)OCc2oc(=O)oc2C(C)C)cc1]
TABLE K
Pyridin-2-yl Compounds.
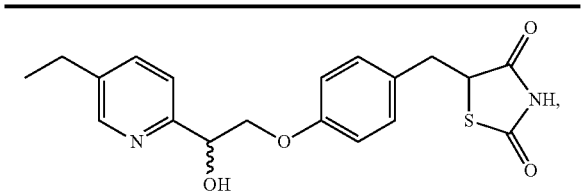
TABLE K-continued
Pyridin-2-yl Compounds.
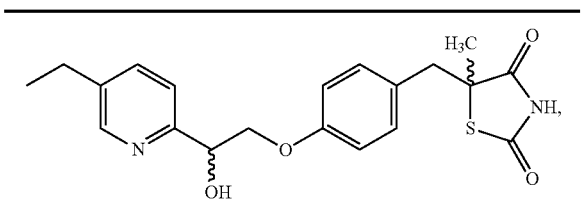
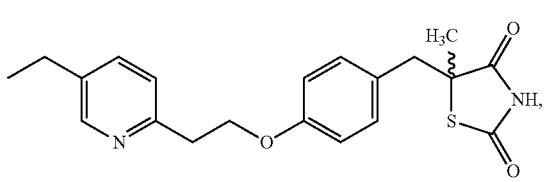 [SMILES: CCc1ccc(CCOc2ccc(CC3(C)SC(=O)NC3=O)cc2)nc1]
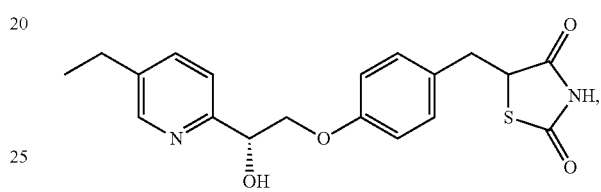
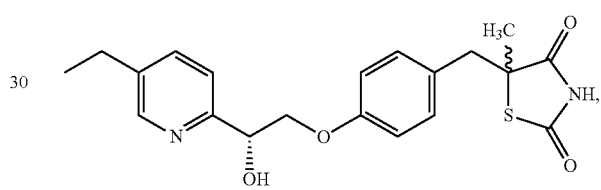
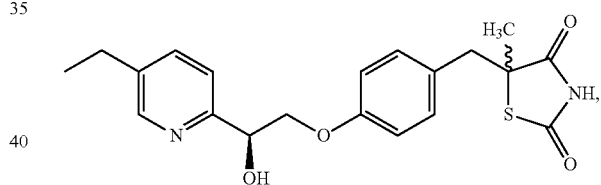
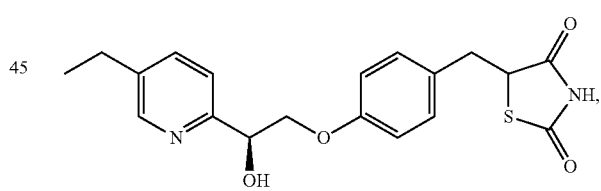
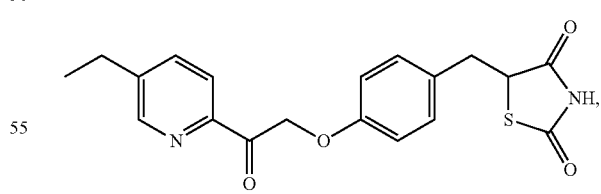
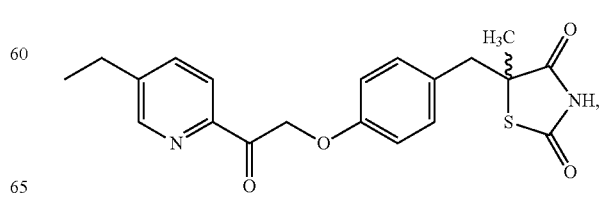

TABLE K-continued
Pyridin-2-yl Compounds.
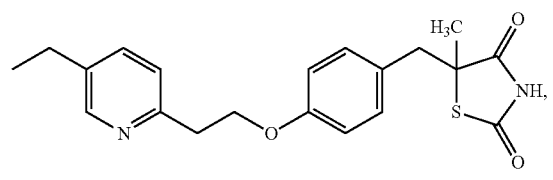
(+)-enantiomer
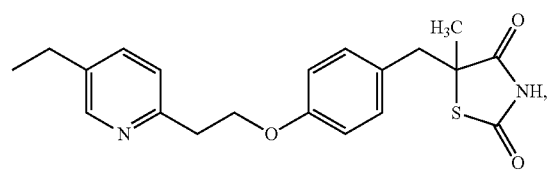
(−)-enantiomer
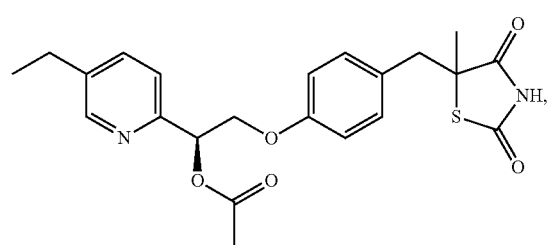 [SMILES: CCc1ccc([C@@H](COc2ccc(CC3(C)SC(=O)NC3=O)cc2)OC(C)=O)nc1]
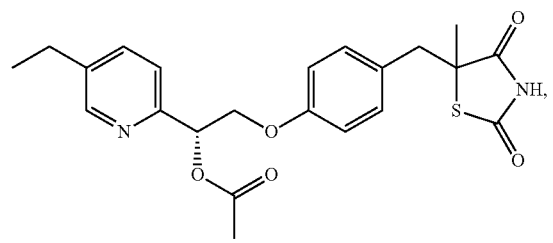 [SMILES: CCc1ccc([C@H](COc2ccc(CC3(C)SC(=O)NC3=O)cc2)OC(C)=O)nc1]
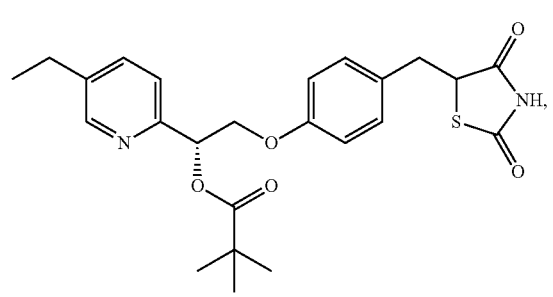 [SMILES: CCc1ccc([C@H](COc2ccc(CC3SC(=O)NC3=O)cc2)OC(=O)C(C)(C)C)nc1]
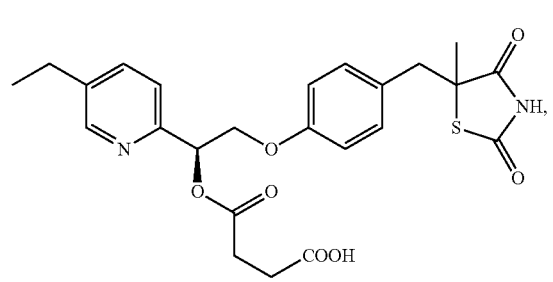 [SMILES: CCc1ccc([C@@H](COc2ccc(CC3(C)SC(=O)NC3=O)cc2)OC(=O)CCC(=O)O)nc1]
TABLE K-continued
Pyridin-2-yl Compounds.
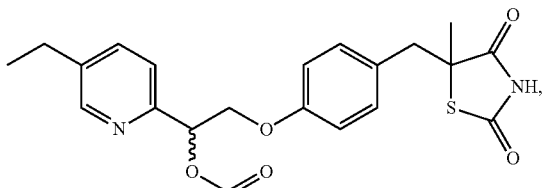
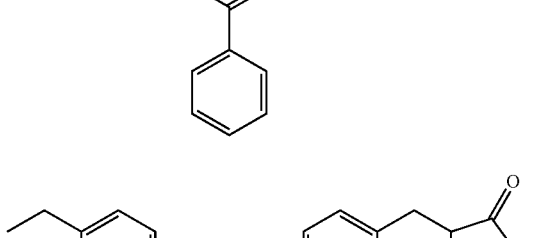
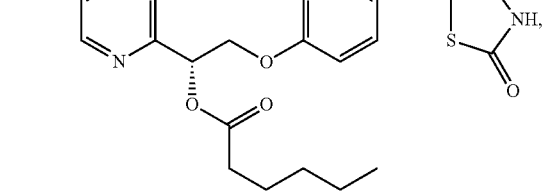, or
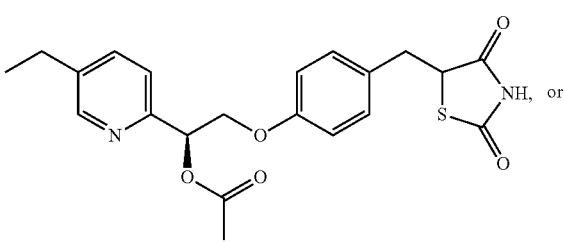 [SMILES: CCc1ccc([C@@H](COc2ccc(CC3SC(=O)NC3=O)cc2)OC(C)=O)nc1 ; "or"]
TABLE L
Pyridin-3-yl Compounds.
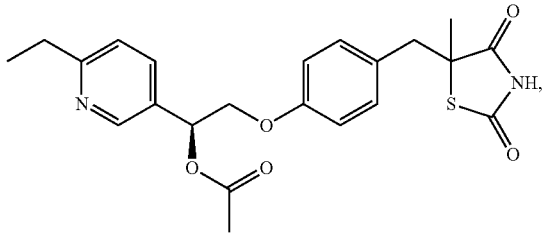 [SMILES: CCc1ccc([C@@H](COc2ccc(CC3(C)SC(=O)NC3=O)cc2)OC(C)=O)cn1]

TABLE L-continued

Pyridin-3-yl Compounds.

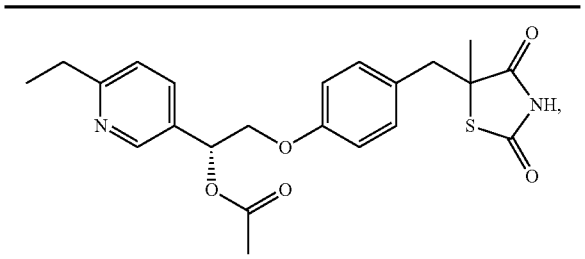

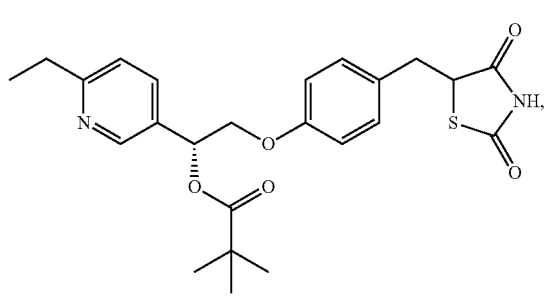 [SMILES: CCc1ccc([C@H](COc2ccc(CC3SC(=O)NC3=O)cc2)OC(=O)C(C)(C)C)cn1]

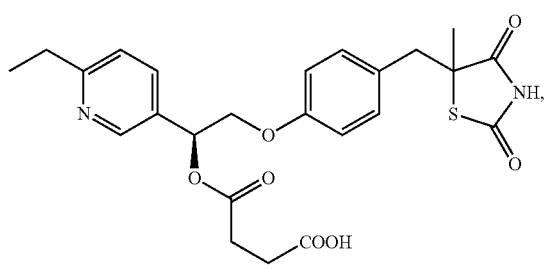 [SMILES: CCc1ccc([C@@H](COc2ccc(CC3(C)SC(=O)NC3=O)cc2)OC(=O)CCC(=O)O)cn1]

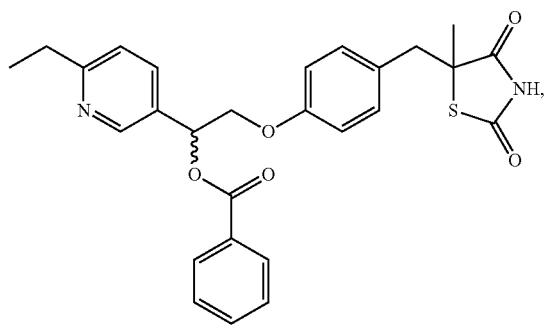 [SMILES: CCc1ccc(C(COc2ccc(CC3(C)SC(=O)NC3=O)cc2)OC(=O)c2ccccc2)cn1]

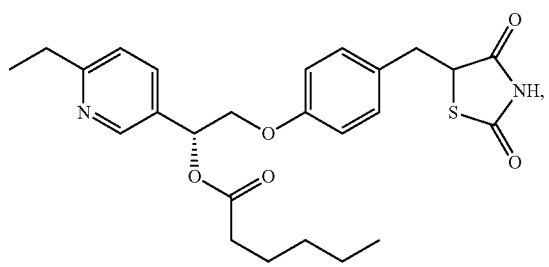 [SMILES: CCCCCC(=O)O[C@@H](COc1ccc(CC2SC(=O)NC2=O)cc1)c1ccc(CC)nc1]

TABLE L-continued

Pyridin-3-yl Compounds.

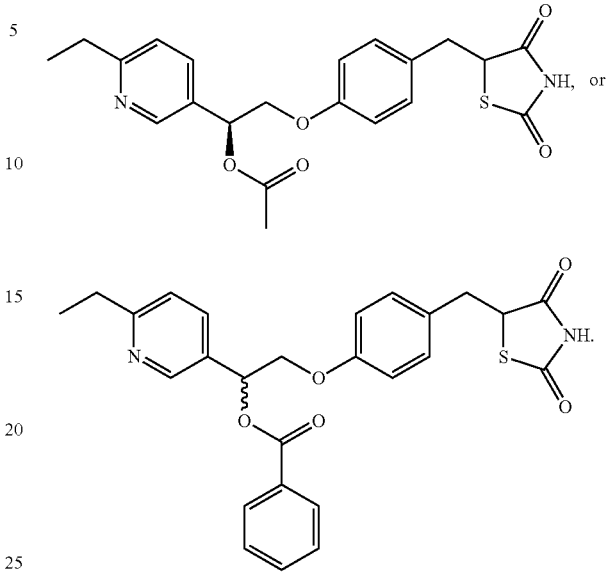

Another aspect of the present invention provides a pharmaceutical composition comprising an acid salt of a compound of Formula I, II, IIA, IIB, IIIA, IIIB, IVA or IVB, and a phosphodiesterase inhibitor (e.g., caffeine). For example, a co-crystal comprises an HCl salt of a compound of Formula I, II, IIA, IIB, IIIA, IIIB, IVA or NB, and a phosphodiesterase inhibitor. In another example, a co-crystal comprises an $H_2SO_4$ salt of a compound of Formula I, II, IIA, IIB, IIIA, IIIB, IVA or IVB, and a phosphodiesterase inhibitor (e.g., caffeine).

Another aspect of the present invention provides a salt comprising a compound of Formula I, II, IIA, IIB, IIIA, IIIB, IVA or IVB, and a phosphodiesterase inhibitor, wherein the compound has a PPARγ activity of 50% or less relative to the activity of rosiglitazone when dosed to produce circulating levels greater than 3 µM or having a PPARγ activity of 10 times less than pioglitazone at the same dosage.

Another aspect of the present invention provides a pharmaceutical composition comprising a salt of a compound of Formula I, a phosphodiesterase inhibitor, and a pharmaceutically acceptable carrier.

B. Phosphodiesterase Inhibitors

In several embodiments, the phosphodiesterase inhibitor is a selective inhibitor or a non-selective inhibitor.

For example, the phosphodiesterase inhibitor is a non-selective inhibitor. In several instances, the non-selective phosphodiesterase inhibitor includes caffeine (1,3,7-trimethylxanthine), theobromine (3,7-dimethyl-2,3,6,7-tetrahydro-1H-purine-2,6-dione), theophylline (1,3-dimethyl-7H-purine-2,6-dione), combinations thereof, or the like.

In another example, the phosphodiesterase inhibitor is a selective inhibitor. For instance, the selective phosphodiesterase inhibitor includes Milrinone (2-methyl-6-oxo-1,6-dihydro-3,4'-bipyridine-5-carbonitrile), Cilostazol (6-[4-(1-cyclohexyl-1H-tetrazol-5-yl)butoxy]-3,4-dihydro-2(1H)-quinolinone), Cilomilast (4-cyano-4-(3-cyclopentyloxy-4-methoxyphenyl)cyclohexane-1-carboxylic acid), Rolipram (4-(3-cyclopentyloxy-4-methoxy-phenyl)pyrrolidin-2-one), Roflumilast (3-(cyclopropylmethoxy)-N-(3,5-dichloropyridin-4-yl)-4-(difluoromethoxy)benzamide), combinations thereof, or the like.

In several embodiments, the phosphodiesterase inhibitor is present in the co-crystal according to the ratio from about 1:1 to about 1:5 (e.g., 1:1, 1:2, 1:3, or 1:4) wherein the ratio represents the amount of phosphodiesterase inhibitor relative to the amount of compound of Formula I, i.e., amount of phosphodiesterase inhibitor (in grams): amount of compound of Formula I (in grams). Note that in some embodiments, the co-crystal also comprises method artifacts such as week acids that are used to facilitate crystal formation.

In one embodiment, the co-crystal comprises caffeine and a compound of Formula I, wherein the caffeine is present according to a ratio of from about 1:1 to about 1:2.5 (e.g., from about 1:1.25 to about 1:2), wherein the ratio represents the amount (in grams) of phosphodiesterase inhibitor relative to the amount of compound of Formula I. In one example, the co-crystal comprises caffeine and a compound of Formula I, wherein caffeine is present in according to the ratio 1:1.5, i.e., about 40 wt %, relative to the compound of Formula I. In another example, the co-crystal comprises 5-(4-(2-(5-ethylpyridin-2-yl)-2-oxoethoxy)benzyl)-1,3-thiazolidine-2,4-dione and caffeine, wherein the caffeine is present according to the ratio from about 1:1.25 to about 1:1.75 (e.g., about 1:1.5) relative to 5-(4-(2-(5-ethylpyridin-2-yl)-2-oxoethoxy)benzyl)-1,3-thiazolidine-2,4-dione.

In other embodiments, the present invention provides a co-crystal comprising a compound of Formula I, II, IIA, IIB, IIIA, IIIB, IVA or IVB, or a pharmaceutically acceptable salt thereof, and a phosphodiesterase inhibitor.

C. Other Pharmaceutical Compositions

Another aspect of the present invention provides a pharmaceutical composition comprising a salt of a compound of Formula I and an agent that affects (e.g., increases) cellular cyclic nucleotide levels (e.g., increases cAMP) in a patient. Agents that increase cAMP in a patient include, without limitation, β-adrenergic agonists, hormones (e.g., GLP1), any combination thereof, or the like.

In one particular example, the pharmaceutical composition comprises a salt of a compound of Formula I and a β-adrenergic agonist, wherein the salt comprises the hydrogen chloride salt, the sulfuric acid salt, or the alkali earth metal salt of the compound

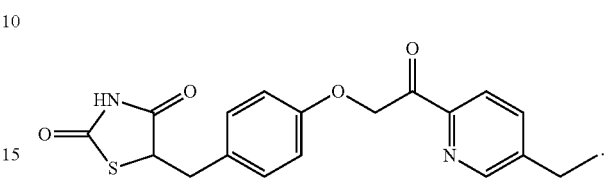

Another aspect of the present invention provides a pharmaceutical composition comprising a co-crystal, a beta-adrenergic agonist, and at least one additional weight loss drug, wherein the co-crystal comprises a salt of a compound of Formula I, II, IIA, IIB, IIIA, IIIB, IVA or IVB and a phosphodiesterase inhibitor. Non-limiting examples of other weight loss drugs include appetite suppressants (e.g., Meridia, or the like), fat absorption inhibitors (e.g., Xenical, or the like), or compounds that augment sympathomimetic activity such as ephedrine or its various salts.

III. General Synthetic Schemes

The compounds of Formula I and II may be readily synthesized from commercially available or known starting materials by known methods. Exemplary synthetic routes to produce compounds of Formula I, II, IIA, IIB, IIIA, IIIB, IVA or IVB are provided in Scheme 1 below.

Scheme 1:

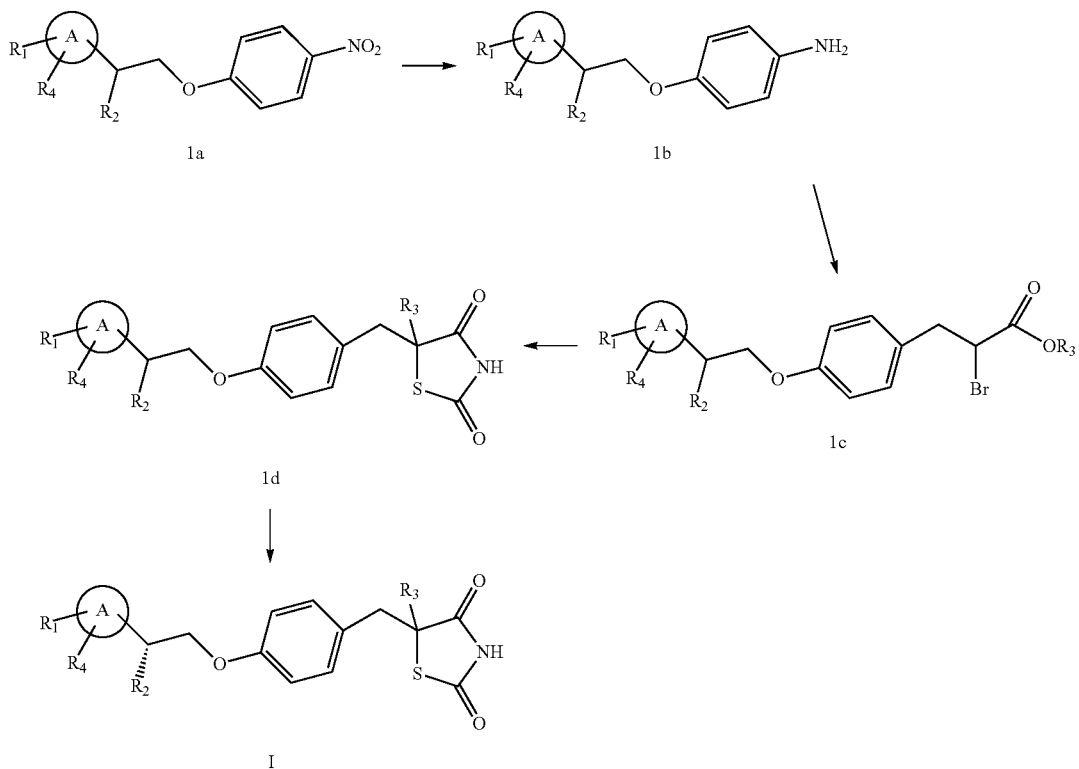

Referring to Scheme 1, the starting material 1a is reduced to form the aniline 1b. The aniline 1b is diazotized in the presence of hydrobromic acid, acrylic acid ester, and a catalyst such as cuprous oxide to produce the alpha-bromo acid ester 1c. The alpha-bromo acid ester 1c is cyclized with thiourea to produce racemic thiazolidinedione 1d. Compounds of Formula II can be separated from the racemic mixture using any suitable process such as HPLC.

In Scheme 2 below, $R_2$ and $R'_2$ form an oxo group or —O-Q and $R_3$ is hydrogen.

Scheme 2:

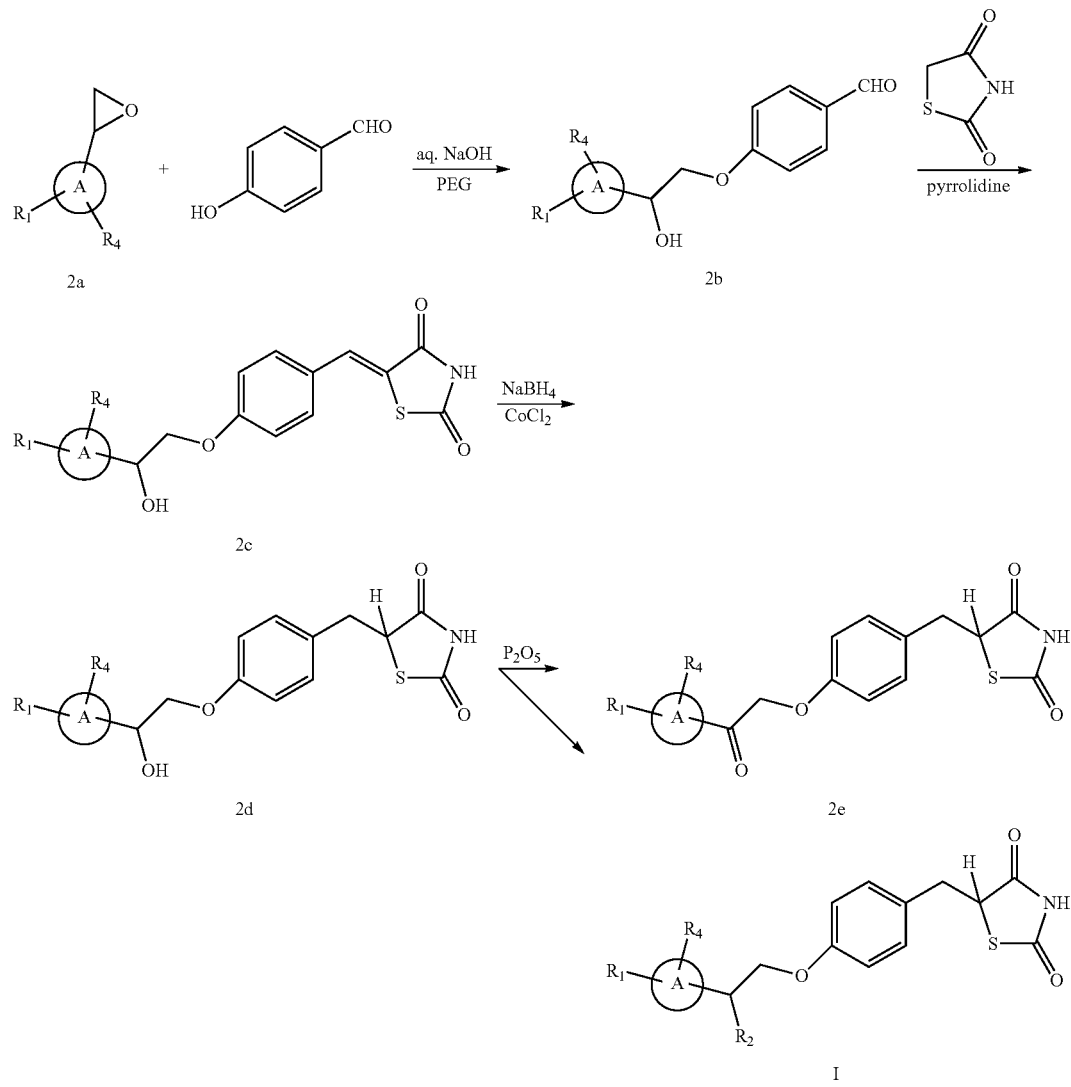

be prepared from the hydroxy compound 2d using known methods of alkylation, acylation, sulfonation or phosphorylation.

IV. Uses, Formulations, and Administration

As discussed above, the present invention provides co-crystals that are useful as treatments or preventative measures for metabolic diseases such as obesity, diabetes, and/or neurodegenerative diseases.

Accordingly, in another aspect of the present invention, pharmaceutically acceptable compositions are provided, Referring to Scheme 2, the starting material 2a is reacted with 4-hydroxybenzalde under basic conditions (e.g., aq. NaOH) to give a mixture of regioisomeric alcohols 2b that were separated by chromatography. The regioisomeric alcohols 2b is reacted with 2,4-thiazolidinedione using pyrrolidine as base to give compound 2c. Cobalt catalyzed reduction with sodium borohydride affords compound 2d, which is oxidized, for example, with phosphorus pentoxide in the presence of dimethyl sulfoxide, to give the ketone 2e. Alternatively, compounds of Formula I wherein $R_2$ is —O-Q, may wherein these compositions comprise any of the co-crystals described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describes pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

According to the invention an "effective amount" of the compound or pharmaceutically acceptable composition is that amount effective for treating or lessening the severity of cancer diseases.

The pharmaceutical compositions, according to the method of the present invention, may be administered using any amount and any route of administration effective for treating or lessening the severity of obesity and/or obesity related diseases.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors known in the medical arts. The term "patient", as used herein, means an animal, for example, a mammal, and more specifically a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect. Alternatively, the compounds of the invention may be administered orally or parenterally at dosage levels of between 10 mg/kg and about 120 mg/kg.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as treatments for cancer diseases.

The activity, or more importantly, reduced PPARγ activity of a compound utilized in this invention as a treatment of obesity and/or reducing bodyweight may be assayed according to methods described generally in the art and in the examples provided herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121, each of which is incorporated by reference.

The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

In order that the invention described herein may be more fully understood, the following examples are set forth. It should be understood that these examples are for illustrative purposes only and are not to be construed as limiting this invention in any manner.

V. EXAMPLES

Some of the following abbreviations used below are defined in Table M.

TABLE M

Definitions for Abbreviations.

| Category | Abbreviations/Acronyms | Full Name/Description |
|---|---|---|
| Analytical Techniques | DSC | Differential scanning calorimetry |
| | HSM | Hot stage microscopy |
| | OM | Optical microscopy |
| | TGA | Thermogravimetric analysis |
| | XRPD | X-ray powder diffraction |
| Methods | FC | Fast cooling |
| | S/AS | Solvent antisolvent precipitation |
| | SC | Slow cooling |
| | RE | Rotary evaporation |
| | agglom. | Agglomerates/agglomerated |
| Miscellaneous | API | Active pharmaceutical ingredient |
| | BE | Birefringence and extinction |
| | BR | Birefringence |
| | E | Extinction |
| | Endo | Endotherm/Endothermic |
| | Exo | Exotherm/Exothermic |
| | LIMS | Laboratory information management system |
| | max | Maximum |
| | RH | Relative humidity |
| | RT | Room temperature |
| | UM | Unknown morphology |
| | w/ | with |
| Solvent | DMF | Dimethylformamide |
| | EtOH | Ethanol |
| | HFIPA | Hexafluoroisopropanol |
| | MTBE | Methyl-tert-butyl ether |
| | TFE | 2,2,2-Trifluoroethanol |
| | THF | Tetrahydrofuran |

Example 1

5-[4-(2-oxo-2-phenylethoxy)benzyl]-1,3-thiazolidine-2,4-dione

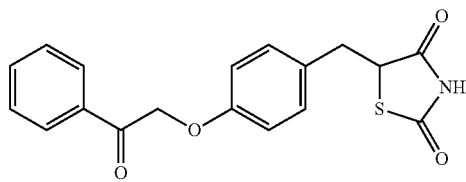 [SMILES: O=C1NC(=O)C(Cc2ccc(OCC(=O)c3ccccc3)cc2)S1]

Step 1. Preparation of 4-(2-hydroxy-2-phenylethoxy)benzaldehyde

To 2-(4-fluorophenyl)oxirane (6.50 g, 54.0 mmol) was added toluene (85 mL), 4-hydroxybenzaldehyde (9.89 g, 81.0 mmol), PEG4000 (polyethylene glycol, 1.15 g) and 1M NaOH (85 mL) and the stirring mixture was heated at 78° C. overnight. After cooling to RT the reaction mixture was extracted with EtOAc, and the organic phase was washed with brine, dried ($Na_2SO_4$), filtered and evaporated in vacuo. The resulting yellow oil was chromatographed on a medium silica gel column eluting with 0-10% EtOAc/DCM. Fractions containing predominantly the higher $R_f$ spot were combined and evaporated in vacuo to give 10.85 g (14%) of the title compound as a yellow oil. Fractions containing predominantly the lower $R_f$ spot were combined and evaporated in vacuo to give 0.64 g of the regioisomer as a colorless, viscous oil. Mixed fractions were combined and rechromatographed eluting with 30% EtOAc/hexanes. Fractions containing the higher $R_f$ material were combined and evaporated in vacuo to give an additional 2.64 g (20%) of the title compound as a colorless oil. Fractions containing the lower $R_f$ material were combined and evaporated in vacuo to give an additional 1.82 g of the regioisomer as a colorless viscous oil.

Step 2: Preparation of 5-[4-(2-hydroxy-2-phenylethoxy)benzylidene]-1,3-thiazolidine-2,4-dione To a stirring solution of 4-[(2S)-2-hydroxy-2-phenylethoxy]benzaldehyde (2.63 g, 10.8 mmol) in absolute EtOH (75 mL) was added 2,4-thiazolidinedione (1.27 g, 10.8 mmol) and piperidine (0.54 mL, 5.4 mmol), and the resulting solution was heated to reflux. The reaction was refluxed overnight. The reaction mixture was allowed to cool to RT. No precipitate formed. The pH of reaction mixture was ca. 5. Acetic acid (20 drops) was added, and the reaction was evaporated in vacuo. The material was adsorbed onto silica gel and chromatographed eluting with 30-40% EtOAc/hexanes. Fractions containing product were combined and evaporated in vacuo to give 3.18 g (86%) of the title compound as a light yellow solid. MS (ESI-) for $C_{18}H_{15}NO_4S$ m/z 340.1 (M-H)$^-$.

Step 3: Preparation of 5-[4-(2-hydroxy-2-phenylethoxy)benzyl]-1,3-thiazolidine-2,4-dione To a mixture of 5-[4-(2-hydroxy-2-phenylethoxy)benzylidene]-1,3-thiazolidine-2,4-dione (1.50 g, 4.39 mmol) in THF (20 mL) was added $H_2O$ (20 mL), 1M NaOH (3 mL), cobalt (II) chloride hexahydrate (0.60 mg, 0.003 mmol) and dimethylglyoxime (15 mg, 0.13 mmol). A solution of sodium tetrahydroborate (240 mg, 6.33 mmol) in 0.2M NaOH (3.6 mL) was added. The reaction mixture immediately turned dark but very soon assumed a clear yellow appearance. Acetic acid was added dropwise until the solution turned dark (3 drops). After ca. one hour, the reaction lightened. Additional $NaBH_4$, $CoCl_2$ and HOAc were added to produce a deep blue-purple color. When that color faded, more $NaBH_4$ was added. When HPLC analysis indicated that the reaction was complete, it was partitioned between $H_2O$ and EtOAc, and the organic phase was washed with brine, dried ($Na_2SO_4$), filtered and evaporated in vacuo. The resulting foamy solid was chromatographed, eluting with 50% EtOAc/hexanes. Fractions containing product were combined and evaporated in vacuo to give 1.15 g (76%) of the title compound as a white solid. MS (ESI-) for $C_{18}H_{17}NO_4S$ m/z 342.1 (M-H)$^-$.

Step 4: Preparation of 5-[4-(2-oxo-2-phenylethoxy)benzyl]-1,3-thiazolidine-2,4-dione To a stirring solution of 5-[4-(2-hydroxy-2-phenylethoxy)benzyl]-1,3-thiazolidine-2,4-dione (1.00 g, 2.91 mmol) in DCM (35 mL) was added DMSO (2 mL) and the solution was cooled to 0° C. Phosphorus pentoxide (0.83 g, 2.91 mmol) was added followed by triethylamine (1.8 mL, 13.1 mmol). The reaction was allowed to slowly warm to RT. After 2 hours, the reaction mixture was partitioned between DCM and water and the organic phase was washed with brine, dried ($Na_2SO_4$), filtered and evaporated in vacuo. The resulting yellow oil was chromatographed on silica gel eluting with 25-35% EtOAc/hexanes. Fractions containing product were combined and evaporated in vacuo to give 0.40 g (40%) of the title compound as a white solid. Trituration with ether afforded 245 mg of clean product. MS (ESI-) for $C_{18}H_{15}NO_4S$ m/z 340.1 (M-H)$^-$.

Example 2

Preparation of 5-{4-[2-(4-fluorophenyl)-2-oxoethoxy]benzyl}-1,3-thiazolidine-2,4-dione

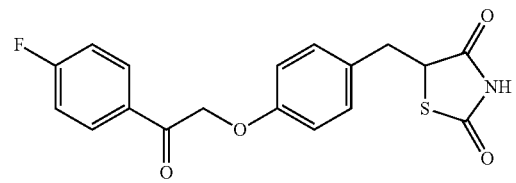 [SMILES: O=C1NC(=O)C(Cc2ccc(OCC(=O)c3ccc(F)cc3)cc2)S1]

Step 1: Preparation of 4-[2-(fluorophenyl)-2-hydroxyethoxy]benzaldehyde

To a stirring solution of 2-(4-fluorophenyl)oxirane (5.60 g, 40.0 mmol) in toluene (65 mL) was added 4-hydroxybenzaldehyde (7.40 g, 61.0 mmol), 1M NaOH (65 mL) and PEG4000 (polyethylene glycol, 0.85 g) and the reaction was heated at 78° C. overnight. After cooling to RT, the reaction was extracted with EtOAc (2×150 mL) and the combined extracts were washed with brine, dried ($Na_2SO_4$), filtered and evaporated in vacuo. The resulting light brown oil was chromatographed on silica gel eluting with 30-40% EtOAc/hexanes. Fractions containing the higher $R_f$ spot were combined and evaporated in vacuo to give 2.38 g of the regioisomer of the product as a white solid. Fractions containing the lower $R_f$ spot were combined and evaporated in vacuo to give 1.54 g (22%) of the title compound as a colorless viscous oil.

Step 2: Preparation of 5-{4-[2-(4-fluorophenyl)-2-hydroxyethoxy]benzylidene}-1,3-thiazolidine-2,4-dione To a stirring solution of the aldehyde (2.36 g, 10.8 mmol) in absolute EtOH (75 mL) was added 2,4-thiazolidinedione (1.06 g, 9.07 mmol) and piperidine (0.45 mL, 4.50 mmol), and the resulting solution was heated to reflux. After refluxing overnight, the reaction was allowed to cool to RT, and then evaporated in vacuo. The residue was adsorbed onto silica gel and chromatographed, eluting with 30-40% EtOAc/hexanes. Fractions containing product were combined and evaporated in vacuo to give 0.88 g (27%) of the title compound as a yellow solid. MS (ESI−) for $C_{18}H_{14}FNO_4S$ m/z 358.1 (M−H)⁻.

Step 3: Preparation of 5-{4-[2-(4-fluorophenyl)-2-hydroxyethoxy]benzyl}-1,3-thiazolidine-2,4-dione To a stirring mixture of 5-{4-[2-(4-fluorophenyl)-2-hydroxyethoxy]benzylidene}-1,3-thiazolidine-2,4-dione (0.87 g, 2.40 mmol) in THF/H₂O (1:1, 20 mL) was added 1M NaOH (2 mL), cobalt (II) chloride hexahydrate (0.30 g, 0.001 mmol), dimethylglyoxime (8.4 mg, 0.073 mmol), and finally sodium tetrahydroborate (0.13 g, 3.53 mmol). The reaction turned a deep blue/purple color. After a short time, the dark color began to fade and HOAc was added dropwise to regenerate the darker color. When the color faded and addition of HOAc failed to regenerate it, NaBH₄ was added to regenerate the darker color. The reaction was left to stir at RT overnight. The reaction was partitioned between water and EtOAc. The organic phase was washed with brine, dried (Na₂SO₄), filtered and evaporated in vacuo. The resulting light brown oil was chromatographed, eluting with 35% EtOAc/hexanes. Fractions containing compound were combined and evaporated in vacuo to give 0.77 g (88%) of a light yellow solid. The yellow solid was dissolved in THF (8 mL) and H₂O (8 mL), and the resulting solution was treated with $CoCl_2$ (a small crystal), and 2,2'-dipyridyl (5 mg). Finally, NaBH₄ was added in small portions until the deep blue color persisted. The reaction mixture was partitioned between EtOAc and H₂O, and the aqueous phase was extracted with EtOAc. The combined organic phases were washed with brine, dried (Na₂SO₄), filtered and evaporated in vacuo. The resulting slightly tinted oil was chromatographed on a small silica gel column eluting with 25-35% EtOAc/hexanes. Fractions containing product were combined and evaporated in vacuo to afford 527 mg (60%) of the title compound as a white solid. MS (ESI−) for $C_{18}H_{16}FNO_4S$ m/z 360.1 (M−H)⁻.

Step 4: Preparation of 5-{4-[2-(4-fluorophenyl)-2-oxoethoxy]benzyl}-1,3-thiazolidine-2,4-dione To a stirring solution of 5-{4-[2-(4-fluorophenyl)-2-hydroxyethoxy]benzyl}-1,3-thiazolidine-2,4-dione (0.52 g, 1.40 mmol) in DCM (15 mL) was added DMSO (0.5 mL) and the solution was cooled to 0° C. Phosphorus pentoxide (0.41 g, 1.44 mmol) was added followed by triethylamine (0.90 mL, 6.48 mmol). The reaction was allowed to slowly warm to RT and then stirred for 5 hours. The reaction mixture was partitioned between DCM and H₂O, and the aqueous phase was extracted with DCM. The combined organic phases were washed with brine, dried (Na₂SO₄), filtered and evaporated in vacuo. The resulting white solid was chromatographed on a small silica gel column eluting with 10% EtOAc/DCM. Fractions containing product were combined and evaporated in vacuo to give 0.25 g (48%) of the title compound as a white solid. MS (ESI+) for $C_{18}H_{14}FNO_4S$ m/z 359.9 (M+H)⁺. MS (ESI−) for $C_{18}H_{14}FNO_4S$ m/z 358.0 (M−H)⁻.

Example 3

Preparation of 5-{4-[2-(2-fluorophenyl)-2-oxoethoxy]benzyl}-1,3-thiazolidine-2,4-dione

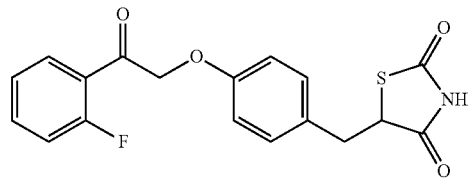 [SMILES: O=C1NC(=O)C(Cc2ccc(OCC(=O)c3ccccc3F)cc2)S1]

Step 1: Preparation of 2-(2-fluorophenyl)oxirane

To a solution of o-fluorostyrene (5.0 g, 41.0 mmol) and acetic acid (2.33 mL, 40.9 mmol) in dioxane (33 mL) and H₂O (78 mL) at 0° C. was added N-bromosuccinimide (8.02 g, 45.0 mol) in three portions. The reaction was allowed to warm to RT and stirred overnight. Sodium carbonate (8.68 g, 81.9 mmol) was added in portions and then 1M NaOH (ca. 10 mL) was added and the reaction was stirred at RT overnight. The reaction mixture was partitioned between water and EtOAc, and the aqueous phase was extracted with EtOAc. The combined organic phases washed with brine, dried (Na₂SO₄), filtered and evaporated in vacuo to give 5.31 g (94%) of the title compound as a slightly tinted oil which was used without further purification. MS (ESI+) for $C_8H_7FO$ m/z 138.1 (M+H)⁺.

Step 2: Preparation of 4-[2-(2-fluorophenyl)-2-hydroxyethoxy]benzaldehyde

To a stirring solution of 2-(2-fluorophenyl)oxirane (5.30 g, 38.4 mmol) in toluene (65 mL) was added 4-hydroxybenzaldehyde (7.0 g, 58.0 mmol), 1M NaOH (65 mL) and PEG4000 (polyethylene glycol, 0.85 g) and the stirring mixture was heated at 78° C. overnight. The reaction was allowed to cool to RT and then extracted with EtOAc (2×150 mL). The combined extracts were washed with brine, dried (Na₂SO₄), filtered and evaporated in vacuo. The resulting light brown oil was adsorbed onto silica gel and chromatographed, eluting with 30-40% EtOAc/hexanes to give 2 major spots. Fractions containing the higher $R_f$ spot were combined and evaporated in vacuo to give 1.10 g (11%) of the title compound as a colorless oil. Fractions containing the lower $R_f$ spot were combined and evaporated in vacuo to give 0.67 g (7%) of the regioisomer as a colorless oil.

Step 3: Preparation of 5-{4-[2-(2-fluorophenyl)-2-hydroxyethoxy]benzylidene}-1,3-thiazolidine-2,4-dione To a stirring solution of the aldehyde (236 g, 10.8 mmol) in absolute EtOH (40 mL) was added 2,4-thiazolidinedione (0.495 g, 4.23 mmol) and piperidine (0.21 mL, 2.10 mmol), and the resulting solution was heated to reflux. After refluxing overnight, the reaction mixture was cooled to RT and then evaporated in vacuo. The residue was dissolved in EtOAc and this solution was washed with dilute aqueous HOAc, brine, dried ($Na_2SO_4$), filtered and evaporated in vacuo. The resulting yellow solid was washed with DCM and acetone and the filtrate was evaporated in vacuo. This material was adsorbed onto silica gel and chromatographed using 10-25% EtOAc/DCM. Fractions containing compound were combined and evaporated in vacuo to give 0.51 g of the title compound as a yellow solid. MS (ESI-) for $C_{18}H_{14}FNO_4S$ m/z 358.0 $(M-H)^-$.

Step 4: Preparation of 5-{4-[2-(2-fluorophenyl)-2-hydroxyethoxy]benzyl}-1,3-thiazolidine-2,4-dione To a stirring mixture of 5-{4-[2-(2-fluorophenyl)-2-hydroxyethoxy]benzylidene}-1,3-thiazolidine-2,4-dione (0.52 g, 1.40 mmol) in $THF/H_2O$ (1:1, 16 mL) was added 1M NaOH (2 mL), cobalt (II) chloride hexahydrate (0.2 mg, 0.0009 mmol), 2,2'-bipyridine (50.8 mg, 0.33 mmol), and finally sodium tetrahydroborate (0.11 g, 2.90 mmol). The reaction turned a deep blue/purple color. After a short time, the dark color began to fade and HOAc was added dropwise to regenerate the darker color. When the color faded and addition of HOAc failed to regenerate it, $NaBH_4$ was added to regenerate the darker color. Added small portions of $NaBH_4$ and HOAc dropwise until deep blue color persisted. After repeating this several times, HPLC indicated that the reaction was complete despite the fact that the deep blue color has given way to a light brown solution. The reaction was partitioned between water and EtOAc. The organic phase was washed with brine, dried ($Na_2SO_4$), filtered and evaporated in vacuo. The resulting light brown oil was chromatographed, eluting with 35% EtOAc/hexanes. Fractions containing compound were combined and evaporated in vacuo to give 0.32 g of the title compound as a white solid. MS (ESI-) for $C_{18}H_{16}FNO_4S$ m/z 360.1 $(M-H)^-$.

Step 5: Preparation of 5-{4-[2-(2-fluorophenyl)-2-oxoethoxy]benzyl}-1,3-thiazolidine-2,4-dione To a stirring solution of 5-{4-[2-(2-fluorophenyl)-2-hydroxyethoxy]benzyl}-1,3-thiazolidine-2,4-dione (0.29 g, 0.80 mmol) in DCM (15 mL) was added DMSO (0.5 mL) and the solution was cooled to 0° C. Phosphorus pentoxide (0.23 g, 0.80 mmol) was added, followed by triethylamine (0.50 mL, 3.6 mmol). The reaction was allowed to slowly warm to RT. After 3 hours, water was added and the phases were separated. The pH of the aqueous phase was adjusted to ca. 7 and the aqueous phase was extracted with DCM. The combined organic phases were washed with brine, dried ($Na_2SO_4$), filtered and evaporated in vacuo. The resulting white solid was chromatographed on a small silica gel column eluting with 10% EtOAc/DCM. Fractions containing product were combined and evaporated in vacuo to give 0.19 g (66%) of the title compound as a white solid. MS (ESI-) for $C_{18}H_{14}FNO_4S$ m/z 358.0 $(M-H)^-$.

Example 4

Preparation of 5-{4-[2-(3-fluorophenyl)-2-oxoethoxy]benzyl}-1,3-thiazolidine-2,4-dione

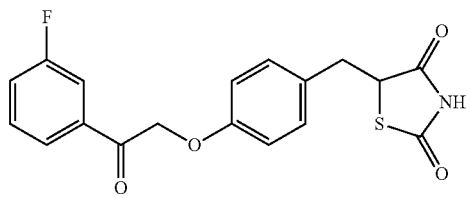 [SMILES: O=C1NC(=O)C(Cc2ccc(OCC(=O)c3cccc(F)c3)cc2)S1]

Step 1: Preparation of 2-(3-fluorophenyl)oxirane

To a solution of m-fluorostyrene (5.00 g, 41.0 mmol) and acetic acid (2.33 mL, 40.9 mmol) in dioxane (33 mL) and $H_2O$ (78 mL) at 0° C. was added N-bromosuccinimide (8.02 g, 45.0 mmol) in three portions. The reaction was allowed to warm to RT. After 4 hours, 2N NaOH (60 mL) was added and the reaction was left to stir at RT overnight. The reaction mixture was partitioned between water and EtOAc, and the aqueous phase was extracted with EtOAc. The combined organic phases were washed with brine, dried ($Na_2SO_4$), filtered and evaporated in vacuo to give 6.30 g of the title compound as a slightly tinted oil which was used without further purification.

Step 2: Preparation of 4-[2-(3-fluorophenyl)-2-hydroxyethoxy]benzaldehyde

To a stirring solution of 2-(3-fluorophenyl)oxirane (5.60 g, 40.5 mmol) in toluene (65 mL) was added 4-hydroxybenzaldehyde (7.40 g, 61.0 mmol), 1M NaOH (65 mL) and PEG4000 (polyethylene glycol, 0.85 g) and the stirring mixture was heated at 78° C. overnight. The reaction mixture was allowed to cool to RT and then extracted with EtOAc (2×150 mL). The combined extracts were washed with brine, dried ($Na_2SO_4$), filtered and evaporated in vacuo. The resulting light brown oil was chromatographed eluting with 30-40% EtOAc/hexanes to give 2 major spots. Fractions containing the higher $R_f$ spot were combined and evaporated in vacuo to give 1.78 g (17%) of the title compound as a white solid. Fractions containing the lower $R_f$ spot were combined and evaporated in vacuo to give 0.90 g (9%) of the regioisomer as a nearly colorless oil.

Step 3: Preparation of 5-{4-[2-(3-fluorophenyl)-2-hydroxyethoxy]benzylidene}-1,3-thiazolidine-2,4-dione To a stirring solution of the aldehyde (2.36 g, 10.8 mmol) in absolute EtOH (40 mL) was added 2,4-thiazolidinedione (0.90 g, 7.69 mmol) and piperidine (0.76 mL, 7.7 mmol), and the resulting solution was heated to reflux. After 6 hours, the reaction mixture was allowed to cool to RT. The mixture was evaporated in vacuo and the residue was dissolved in EtOAc. This solution was washed with a dilute aqueous HOAc, brine, dried ($Na_2SO_4$), filtered and evaporated in vacuo. The resulting yellow solid was dissolved in MeOH/DCM adsorbed onto silica gel and chromatographed eluting with 30% EtOAc/DCM. Fractions containing compound were combined and evaporated in vacuo to afford 2.17 g (86%) of the title compound as a yellow solid. MS (ESI−) for $C_{18}H_{14}FNO_4S$ m/z 358.1 (M−H)−.

Step 4: Preparation of 5-{4-[2-(3-fluorophenyl)-2-hydroxyethoxy]benzyl}-1,3-thiazolidine-2,4-dione 5-{4-[2-(3-fluorophenyl)-2-hydroxyethoxy]benzylidene}-1,3-thiazolidine-2,4-dione (1.00 g, 2.78 mmol) was suspended in THF (15 mL) and H₂O (10 mL). To this solution was added a small crystal of cobalt chloride followed by 2,2'-bipyridine (98 mg, 0.63 mmol). NaBH₄ was added in portions until blue color persisted. The color gradually faded and was regenerated repeatedly by small additions of borohydride and HOAc. When HPLC analysis indicated that the reaction was complete, the reaction mixture was partitioned between EtOAc and H₂O. HOAc was added until the pH of the aqueous phase was ca. 6. The aqueous phase was extracted with EtOAc. The combined organic phases were washed with brine, dried (Na₂SO₄), filtered and evaporated in vacuo. The residue was chromatographed on a small silica gel column eluting with 20% EtOAc/DCM. Fractions containing product were combined and evaporated in vacuo to give 0.72 g (72%) of the title compound as a white solid. This material was rechromatographed on a small silica column eluting with 10-20% EtOAc/DCM. MS (ESI−) for $C_{18}H_{16}FNO_4S$ m/z 360.1 (M−H)−.

Step 5: Preparation of 5-{4-[2-(3-fluorophenyl)-2-oxoethoxy]benzyl}-1,3-thiazolidine-2,4-dione To a stirring solution of 5-{4-[2-(3-fluorophenyl)-2-hydroxyethoxy]benzyl}-1,3-thiazolidine-2,4-dione (0.62 g, 1.70 mmol) in DCM (15 mL) was added DMSO (0.5 mL) and the solution was cooled to 0° C. Added phosphorus pentoxide (0.49 g, 1.72 mmol) followed by triethylamine (1.1 mL, 7.72 mmol). The reaction mixture was allowed to slowly warm to RT. After 2 hours, HPLC shows that the reaction was complete. Added water and separated phases. The pH of the aqueous phase was adjusted to ca. 7 with 2M NaOH and the aqueous phase was then extracted with EtOAc. The combined extracts were washed with brine, dried (Na₂SO₄), filtered and evaporated in vacuo. The resulting white solid was chromatographed on a small silica gel column eluting with 10% EtOAc/DCM. Fractions containing product were combined and evaporated in vacuo to give 0.25 g (40%) of the title compound as a white solid. MS (ESI−) for $C_{18}H_{14}FNO_4S$ m/z 358.0 (M−H)−.

Example 5

Preparation of 5-{4-[2-(3-methoxyphenyl)-2-oxoethoxy]benzyl}-1,3-thiazolidine-2,4-dione (Compound B)

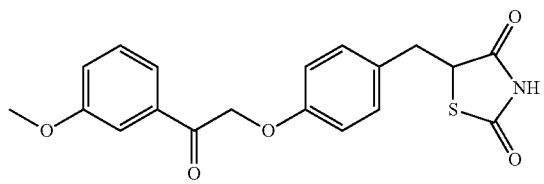 [SMILES: COc1cccc(C(=O)COc2ccc(CC3SC(=O)NC3=O)cc2)c1]

Step 1: 2-(3-methoxyphenyl)oxirane

To a solution of 3-vinylanisole (5.0 g, 37.0 mmol) and acetic acid (2.1 mL, 37.0 mmol) in dioxane (33 mL) and H₂O (78 mL) at 0° C. was added N-bromosuccinimide (7.30 g, 41.0 mmol) in three portions. The reaction was allowed to warm to RT and then 2M NaOH (50 mL) was added. The reaction was left to stir at RT overnight. The reaction mixture was then partitioned between water and EtOAc, and the aqueous phase was extracted with EtOAc. The combined organic phases washed with brine, dried (Na₂SO₄), filtered and evaporated in vacuo to give 5.60 g (100%) of the title compound as a slightly tinted oil.

Step 2: 4-[2-hydroxy-2-(3-methoxyphenyl)ethoxy]benzaldehyde

To a stirring solution of 2-(3-methoxyphenyl)oxirane (5.60 g, 37.0 mmol) in toluene (65 mL) was added 4-hydroxybenzaldehyde (6.80 g, 5.60 mmol), 1M NaOH (65 mL) and PEG4000 (polyethylene glycol, 0.85 g) and the stirring mixture was heated at 78° C. overnight. The reaction mixture was allowed to cool to RT and extracted with EtOAc (2×150 mL). The combined extracts were washed with brine, dried (Na₂SO₄), filtered and evaporated in vacuo. The resulting light brown oil was chromatographed, eluting with 30-40% EtOAc/hexanes. Fractions containing the higher $R_f$ spot were combined and evaporated in vacuo to give 1.86 g (18%) of the title compound as a clear colorless oil. Fractions containing the lower $R_f$ spot were combined and evaporated in vacuo to give 0.90 g (9%) the regioisomer as a nearly colorless oil.

Step 3: 5-{4-[2-hydroxy-2-(3-methoxyphenyl)ethoxy]benzylidene}-1,3-thiazolidine-2,4-dione To a stirring solution of 4-[2-hydroxy-2-(3-methoxyphenyl)ethoxy]benzaldehyde (1.76 g, 6.46 mmol) in absolute EtOH (50 mL) was added 2,4-thiazolidinedione (0.83 g, 7.11 mmol) and piperidine (0.70 mL, 7.11 mmol), and the resulting solution was heated to reflux. The reaction was refluxed overnight and then evaporated in vacuo. The residue was dissolved in EtOAc and this solution was washed with water (pH adjusted to ca. 5-6 with HOAc), brine, dried (Na₂SO₄), filtered and adsorbed onto silica gel. After chromatography with 20-30% EtOAc/DCM, the fractions containing compound were combined and evaporated in vacuo to give 1.38 g (58%) of the title compound as a yellow solid. MS (ESI−) for $C_{19}H_{17}NO_5S$ m/z 370.1 (M−H)−.

Step 4: 5-{4-[2-hydroxy-2-(3-methoxyphenyl)ethoxy]benzyl}-1,3-thiazolidine-2,4-dione 5-{-4-[2-hydroxy-2-(3-methoxyphenyl)ethoxy]benzylidene}-1,3-thiazolidine-2,4-dione (1.15 g, 3.10 mmol) was dissolved in THF (15 mL). Added H₂O (15 mL) and sufficient THF to give a clear solution. A small crystal of cobalt chloride was added, followed by 2,2'-bipyridine (109 mg, 0.70 mmol). NaBH₄ was added in portions until the blue color persisted. The color gradually faded, but was regenerated repeatedly by small additions of borohydride and HOAc. When HPLC indicated that the reaction was complete the reaction mixture was partitioned between EtOAc and H₂O. HOAc was added until the pH of the aqueous phase was ca. 6, and then the aqueous phase was extracted with EtOAc. The combined organic phases were washed with brine, dried (Na₂SO₄), filtered and evaporated in vacuo. The residue was chromatographed on a small silica gel column eluting with 20% EtOAc/DCM. Fractions containing product were combined and evaporated in vacuo to give 0.82 g (74%) of the title compound as a white solid. MS (ESI−) for $C_{19}H_{19}NO_5S$ m/z 372.0 (M−H)⁻.

Step 5: Preparation of 5-{4-[2-(3-methoxyphenyl)-2-oxoethoxy]benzyl}-1,3-thiazolidine-2,4-dione To a stirring solution of 5-{4-[2-hydroxy-2-(3-methoxyphenyl)ethoxy]benzyl}-1,3-thiazolidine-2,4-dione (0.62 g, 1.7 mmol) in DCM (15 mL) was added DMSO (0.5 mL) and the solution was cooled to 0° C. Added phosphorus pentoxide (0.52 g, 1.8 mmol) followed by triethylamine (1.2 mL, 8.3 mmol). The reaction was allowed to slowly warm to RT. After 2 hours water was added and the phases were separated. The pH of the aqueous phase was adjusted to ca. 7 with 2M NaOH. The aqueous phase was extracted with EtOAc. The combined extracts were washed with brine, dried ($Na_2SO_4$), filtered and evaporated in vacuo. The resulting white solid was chromatographed on a small silica gel column eluting with 10% EtOAc/DCM. Fractions containing product were combined and evaporated in vacuo to give 0.33 g (54%) of the title compound as a white solid. MS (ESI+) for $C_{19}H_{17}NO_5S$ m/z 372.0 (M+H)⁺. MS (ESI−) for $C_{19}H_{17}NO_5S$ m/z 370.1 (M−H)⁻.

Example 6

Preparation of 5-{4-[2-(2-methoxyphenyl)-2-oxoethoxy]benzyl}-1,3-thiazolidine-2,4-dione

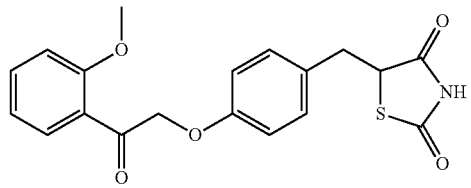 [SMILES: COc1ccccc1C(=O)COc1ccc(CC2SC(=O)NC2=O)cc1]

Step 1: Preparation of 2-(2-methoxyphenyl)oxirane

To a solution of 2-vinyl anisole (5.0 g, 0.037 mol) and acetic acid (2.1 mL, 37 mmol) in dioxane (33 mL) and $H_2O$ (78 mL) at 0° C. was added N-bromosuccinimide (7.30 g, 40.1 mmol) in three portions. The reaction was allowed to warm to RT and after 1 hour, 2M NaOH (50 mL) was added. The reaction was left to stir at RT overnight. The reaction mixture was partitioned between water and EtOAc, and the aqueous phase was extracted with EtOAc. The combined organic phases were washed with brine, dried ($Na_2SO_4$), filtered and evaporated in vacuo to give 7.56 g slightly tinted oil. This was dissolved in dioxane, 2N NaOH was added and the reaction was stirred at RT overnight. Repeated aqueous work-up gave 5.60 g of the title compound as a nearly colorless oil.

Step 2: Preparation of 4-[2-hydroxy-2-(2-methoxyphenyl)ethoxy]benzaldehyde

To a stirring solution of 2-(2-methoxyphenyl)oxirane (5.60 g, 37.3 mmol) in toluene (65 mL) was added 4-hydroxybenzaldehyde (6.80 g, 56.0 mmol), 1M NaOH (65 mL) and PEG4000 (polyethylene glycol, 0.85 g) and the stirring mixture was heated at 78° C. overnight. The reaction was allowed to cool to RT and it was then extracted with EtOAc (2×150 mL). The combined extracts were washed with brine, dried ($Na_2SO_4$), filtered and evaporated in vacuo. The resulting light oil was adsorbed onto silica gel and chromatographed eluting with 30-40% EtOAc/hexanes to give 2 major spots. Fractions containing the higher $R_f$ spot were combined and evaporated in vacuo to give 1.71 g (17%) the regioisomer as a brown oil. Fractions containing the lower $R_f$ spot were combined and evaporated in vacuo to give 2.05 g (20%) of the title compound as a yellow solid.

Step 3: Preparation of (5Z)-5-{4-[2-hydroxy-2-(2-methoxyphenyl)ethoxy]benzylidene}-1,3-thiazolidine-2,4-dione To a stirring solution of 4-[2-hydroxy-2-(2-methoxyphenyl)ethoxy]benzaldehyde (1.71 g, 6.28 mmol) in absolute EtOH (50 mL) was added 2,4-thiazolidinedione (0.81 g, 6.91 mmol) and piperidine (0.68 mL, 6.9 mmol), and the resulting solution was heated to reflux. The reaction was refluxed overnight and then evaporated in vacuo. The residue was dissolved in EtOAc and this solution was washed with aqueous HOAc (pH 5-6), brine, dried ($Na_2SO_4$), filtered and evaporated in vacuo. The residue was adsorbed onto silica gel and chromatographed on silica gel eluting with 20-40% EtOAc/DCM. Fractions containing product were combined and evaporated in vacuo to give 1.87 g (80%) of the title compound as a light yellow solid. MS (ESI−) for $C_{19}H_{17}NO_5S$ m/z 370.1 (M−H)⁻.

Step 4: 5-{4-[2-hydroxy-2-(2-methoxyphenyl)ethoxy]benzyl}-1,3-thiazolidine-2,4-dione (5Z)-5-{4-[2-hydroxy-2-(2-methoxyphenyl)ethoxy]benzylidene}-1,3-thiazolidine-2,4-dione (1.00 g, 2.69 mmol) was dissolved in THF (20 mL). Water (20 mL) was added and then sufficient additional THF was added to give a clear solution. A small crystal of cobalt chloride was added followed by 2,2'-bipyridine (95 mg, 0.61 mmol). The reaction mixture was cooled to 0° C. $NaBH_4$ was added in portions until the blue color persisted. The color gradually faded and was regenerated repeatedly by small additions of borohydride and HOAc. When HPLC indicated that the reaction was complete the reaction mixture was partitioned between EtOAc and $H_2O$. HOAc was added until the pH of the aqueous phase was ca. 6, and the aqueous phase was extracted with EtOAc. The combined organic phases were washed with brine, dried ($Na_2SO_4$), filtered and evaporated in vacuo. The residue was chromatographed on a small silica gel column eluting with 20% EtOAc/DCM. Fractions containing product were combined and evaporated in vacuo to give 0.63 g (63%) of the title compound as a white solid. MS (ESI−) for $C_{19}H_{19}NO_5S$ m/z 372.1 (M−H)⁻.

Step 5: Preparation of 5-{4-[2-(2-methoxyphenyl)-2-oxoethoxy]benzyl}-1,3-thiazolidine-2,4-dione To a stirring solution of phosphorus pentoxide (0.30 g, 1.10 mmol) in DCM (8 mL) at 0° C. was added a solution of 5-{4-[2-hydroxy-2-(2-methoxyphenyl)ethoxy]benzyl}-1,3-thiazolidine-2,4-dione (0.20 g, 0.54 mmol) in DCM (8 mL) followed by dimethyl sulfoxide (0.20 mL, 2.80 mmol). After stirring for 15 minutes, N,N-diisopropylethylamine (0.28 mL, 1.60 mmol) was added. After 45 minutes, the reaction mixture was cast into cold saturated $NaHCO_3$ and extracted with EtOAc (×2). The combined extracts were washed with brine, dried ($Na_2SO_4$), filtered and evaporated in vacuo. The residue was chromatographed on a small silica gel column eluting with 0-10% EtOAc/DCM. Fractions containing product were combined and evaporated in vacuo to give 175 mg (88%) of the title compound as a light yellow solid. MS (ESI−) for $C_{19}H_{17}NO_5S$ m/z 370.1 (M−H)⁻.

Example 7

Preparation of 5-{4-[2-(3-chlorophenyl)-2-oxoethoxy]benzyl}-1,3-thiazolidine-2,4-dione

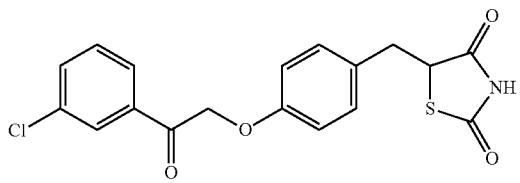 [SMILES: O=C1NC(=O)C(Cc2ccc(OCC(=O)c3cccc(Cl)c3)cc2)S1]

Step 1: 2-(3-chlorophenyl)oxirane

To a solution of m-chlorostyrene (5.70 g, 41.0 mmol) and acetic acid (2.33 mL, 40.9 mmol) in dioxane (33 mL) and $H_2O$ (78 mL) at 0° C. was added N-bromosuccinimide (8.02 g, 45.0 mmol) in three portions. The reaction was allowed to warm to RT After 4 hours, 2N NaOH (60 mL) was added and the reaction was allowed to stir at RT overnight. The reaction mixture was partitioned between water and EtOAc, and the aqueous phase was extracted with EtOAc. The combined organic phases were washed with brine, dried ($Na_2SO_4$), filtered and evaporated in vacuo to give 6.20 g of a slightly tinted oil which was used without further purification.

Step 2:
4-[2-(3-chlorophenyl)-2-hydroxyethoxy]benzaldehyde

To a stirring solution of 2-(3-chlorophenyl)oxirane (6.20 g, 40.0 mmol) in toluene (65 mL) was added 4-hydroxybenzaldehyde (7.30 g, 60.0 mmol), 1M NaOH (65 mL) and PEG4000 (polyethylene glycol, 0.85 g) and the stirring mixture was heated at 78° C. for three hours. The reaction was allowed to cool to RT and then extracted with EtOAc (2×150 mL). The combined extracts were washed with brine, dried ($Na_2SO_4$), filtered and evaporated in vacuo. The resulting light brown oil was adsorbed onto silica gel and chromatographed eluting with 25-40% EtOAc/hexanes. There are 2 major spots. Fractions containing the higher $R_f$ spot were combined and evaporated in vacuo to give 1.08 g (10%) of the desired product as a colorless oil. Fractions containing the lower $R_f$ spot were combined and evaporated in vacuo to give 0.95 g (8%) of the regioisomer as a colorless oil, 44B. Some starting epoxide (2.85 g) was also recovered.

Step 3: 5-{4-[2-(3-chlorophenyl)-2-hydroxyethoxy]benzylidene}-1,3-thiazolidine-2,4-dione To a stirring solution of 4-[2-(3-chlorophenyl)-2-hydroxyethoxy]benzaldehyde (1.08 g, 3.90 mmol) in absolute EtOH (50 mL) was added 2,4-thiazolidinedione (0.50 g, 4.29 mmol) and piperidine (0.42 mL, 4.3 mmol), and the resulting solution was heated to reflux and then stirred overnight at room temperature. The reaction mixture was evaporated in vacuo and the residue was dissolved in EtOAc. This solution was washed with aqueous HOAc (pH 5-6), brine, dried ($Na_2SO_4$), filtered and evaporated in vacuo. The residue was adsorbed onto silica gel and chromatographed eluting with 10-20% EtOAc/DCM. Fractions containing product were combined and evaporated in vacuo to give 131 g (89%) of the product as a light yellow solid. MS (ESI+) for $C_{18}H_{14}ClNO_4S$ m/z 375.0 (M+H)⁺. MS (ESI−) for $C_{18}H_{14}ClNO_4S$ m/z 374.1 (M−H)⁻.

Step 4: 5-{4-[2-(3-chlorophenyl)-2-hydroxyethoxy]benzyl}-1,3-thiazolidine-2,4-dione 5-{4-[2-(3-chlorophenyl)-2-hydroxyethoxy]benzylidene}-1,3-thiazolidine-2,4-dione (0.74 g, 2.00 mmol) was dissolved in THF (20 mL). Water (20 mL) was added and then more THF was added until all solids dissolved. A small crystal of cobalt chloride was added, followed by 2,2′-bipyridine (69 mg, 0.44 mmol). The reaction mixture was cooled to 0° C. $NaBH_4$ was added in portions until the blue color persisted. The color gradually faded and was regenerated repeatedly by small additions of borohydride and HOAc. When HPLC indicated that the reaction was complete, the reaction mixture was partitioned between EtOAc and $H_2O$. HOAc was added until the pH of the aqueous phase was ca. 6, and then the aqueous phase was extracted with EtOAc. The combined organic phases were washed with brine, dried ($Na_2SO_4$), filtered and evaporated in vacuo. The residue was chromatographed on a small silica gel column eluting with 0-10% EtOAc/DCM. Fractions containing product were combined and evaporated in vacuo to give 0.44 g (59%) of a sticky yellow solid. MS (ESI−) for $C_{18}H_{16}ClNO_4S$ m/z 376.1 (M−H)⁻.

Step 5: Preparation of 5-{4-[2-(3-chlorophenyl)-2-oxoethoxy]benzyl}-1,3-thiazolidine-2,4-dione To a stirring solution of phosphorus pentoxide (0.38 g, 130 mmol) in DCM (8 mL) at 0° C. was added a solution of 5-{4-[2-(3-chlorophenyl)-2-hydroxyethoxy]benzyl}-1,3-thiazolidine-2,4-dione (0.25 g, 0.66 mmol) in DCM (8 mL) followed by dimethyl sulfoxide (0.23 mL, 3.30 mL). After stirring for 15 minutes N,N-diisopropylethylamine (0.34 mL, 2.00 mmol) was added. After 45 minutes the reaction was poured into cold saturated $NaHCO_3$ and the mixture was extracted with EtOAc (×2). The combined extracts were washed with brine, dried ($Na_2SO_4$), filtered and evaporated in vacuo. The residue was chromatographed on a small silica gel column eluting with 0-15% EtOAc/DCM. Fractions containing product were combined and evaporated in vacuo to give 117 mg (47%) of a white solid. MS (ESI−) for $C_{18}H_{14}ClNO_4S$ m/z 374.1 (M−H)⁻.

Example 8

Preparation of 5-{4-[2-(2-chlorophenyl)-2-oxoethoxy]benzyl}-1,3-thiazolidine-2,4-dione The title compound can be prepared as described in Example 7 using appropriate starting materials, such as 2-(2-chlorophenyl)oxirane.

Example 9

Preparation of 5-{4-[2-(4-methoxyphenyl)-2-oxoethoxy]benzyl}-1,3-thiazolidine-2,4-dione The title compound was prepared as described in Examples 5 and 6 using appropriate starting materials, such as 2-(4-methoxyphenyl)oxirane. MS (ESI−) for $C_{19}H_{17}NO_5S$ 370.2 m/z (M−1).

Example 10

Physical Data for Representative Compounds

¹H-NMR Data (400 mHz)

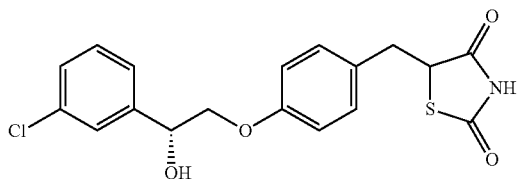 [SMILES: O=C1NC(=O)C(Cc2ccc(OC[C@H](O)c3cccc(Cl)c3)cc2)S1]

¹H-NMR (DMSO-d₆) δ: 12.00 (s, 1H), 7.50 (s, 1H), 7.42-7.32 (m, 3H), 7.13 (d, J=8.5 Hz, 2H), 6.87 (d, J=8.5 Hz, 2H), 5.77 (d, J=5.0 Hz, 1H), 4.92 (d, J=6.2 Hz, 1H), 4.86 (dd, J=8.9, 4.3 Hz, 1H), 4.00 (m, 2H), 3.29 (dd, J=14.3, 4.3 Hz, 1H), 3.05 (dd, J=14.2, 9.0 Hz, 1H).

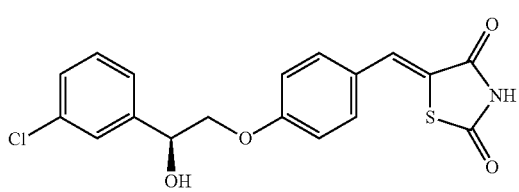 [SMILES: O=C1NC(=O)/C(=C/c2ccc(OC[C@@H](O)c3cccc(Cl)c3)cc2)S1]

¹H-NMR (DMSO-d₆) δ: 12.52 (s, 1H), 7.75 (s, 1H), 7.54 (m, 3H), 7.44-7.33 (m, 3H), 7.11 (d, J=8.91 Hz, 2H), 5.84 (d, J=4.77 Hz, 1H), 4.97 (m, 1H), 4.12 (m, 2H).

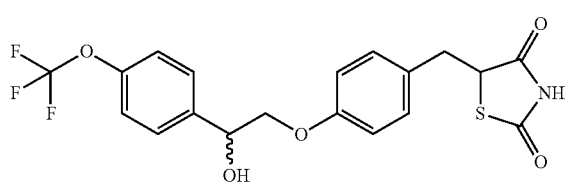 [SMILES: O=C1NC(=O)C(Cc2ccc(OCC(O)c3ccc(OC(F)(F)F)cc3)cc2)S1]

¹H-NMR (CDCl₃) δ: 8.32 (brs, 1H), 7.50 (d, J=8.50 Hz, 2H), 7.26 (m, 2H), 7.17 (m, 2H), 6.88 (m, 2H), 5.15 (dd, J=8.71, 3.11 Hz, 1H), 4.51 (dd, J=9.23, 4.04 Hz, 1H), 4.09 (dd, J=9.64, 3.21 Hz, 1H), 3.45 (dd, J=14.1, 3.94 Hz, 1H), 3.13 (dd, J=14.2, 9.23 Hz, 1H), 2.87 (brs, 1H).

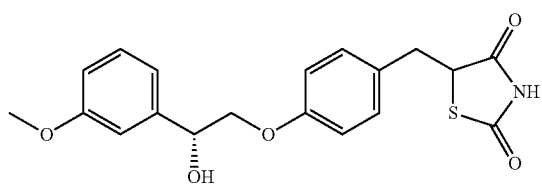 [SMILES: COc1cccc([C@@H](O)COc2ccc(CC3SC(=O)NC3=O)cc2)c1]

¹H-NMR (CDCl₃) δ: 8.35 (brs, 1H), 7.23 (t, J=8.09, 1H), 7.07 (d, J=8.71 Hz, 2H), 6.94 (m, 2H), 6.81 (m, 3H), 5.03 (dd, J=8.60, 2.80 Hz, 1H), 4.42 (dd, J=9.33, 3.94 Hz, 1H), 4.02 (m, 1H), 3.93 (t, J=9.23 Hz, 1H), 3.76 (s, 3H), 3.36 (dd, J=14.20, 3.84 Hz, 1H), 3.04 (dd, J=14.10, 9.33 Hz, 1H), 2.75 (brs, 1H).

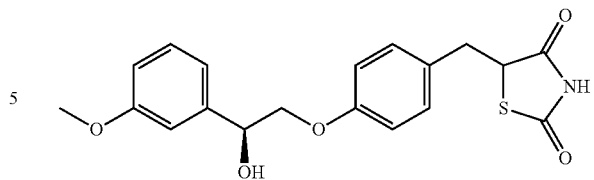

¹H-NMR (CDCl₃) δ: 8.42 (brs, 1H), 7.23 (t, J=7.98 Hz, 1H), 7.07 (d, J=8.71 Hz, 2H), 6.94 (m, 2H), 6.82-6.78 (m, 3H), 5.03 (dd, J=8.71, 2.90 Hz, 1H), 4.41 (dd, J=9.33, 3.94 Hz, 1H), 4.02 (m, 1H), 3.93 (t, J=9.12 Hz, 1H), 3.76 (s, 3H), 3.36 (dd, J=14.10, 3.94 Hz, 1H), 3.03 (dd, J=14.31, 9.33 Hz, 1H), 2.77 (brs, 1H).

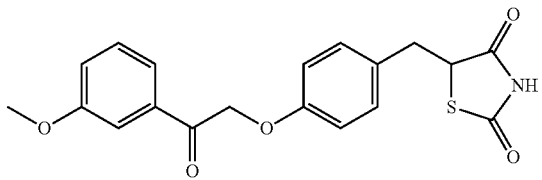 [SMILES: COc1cccc(C(=O)COc2ccc(CC3SC(=O)NC3=O)cc2)c1]

¹H-NMR (DMSO-d₆) δ: 12.03 (brs, 1H), 7.62 (d, J=7.67 Hz, 1H), 7.49 (m, 2H), 7.27 (dd, J=8.19, 2.38 Hz, 1H), 7.16 (d, J=8.50 Hz, 2H), 6.91 (d, J=8.50 Hz, 2H), 5.55 (s, 2H), 4.88 (dd, J=9.12, 4.35 Hz, 1H), 3.84 (s, 3H), 3.33-3.29 (m, 1H), 3.05 (dd, J=14.31, 9.12 Hz, 1H).

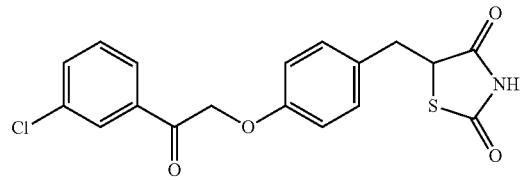 [SMILES: O=C1NC(=O)C(Cc2ccc(OCC(=O)c3cccc(Cl)c3)cc2)S1]

¹H-NMR (DMSO-d₆) δ: 12.02 (brs, 1H), 8.05 (t, J=1.66 Hz, 1H), 7.96 (d, J=7.88 Hz, 1H), 7.77 (m, 1H), 7.61 (t, J=7.88 Hz, 1H), 7.16 (d, J=8.71 Hz, 2H), 6.93 (d, J=8.71 Hz, 2H), 5.57 (s, 2H), 4.88 (dd, J=9.12, 4.35 Hz, 1H), 331 (m, 1H), 3.06 (dd, J=14.20, 9.23 Hz, 1H).

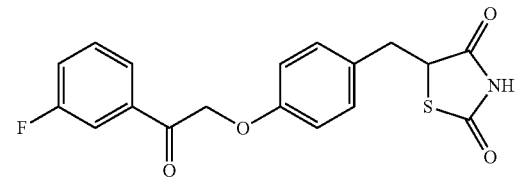 [SMILES: O=C1NC(=O)C(Cc2ccc(OCC(=O)c3cccc(F)c3)cc2)S1]

¹H-NMR (DMSO-d₆) δ: 12.02 (brs, 1H), 7.83 (m, 2H), 7.59 (m, 2H), 7.16 (d, J=8.71 Hz, 2H), 6.93 (d, J=8.71 Hz, 2H), 5.56 (s, 2H), 4.88 (dd, J=9.12, 4.35 Hz, 1H), 3.33-3.29 (m, 1H), 3.06 (dd, J=14.10, 9.12 Hz, 1H).

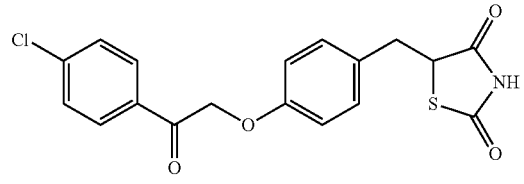 [SMILES: O=C1NC(=O)C(Cc2ccc(OCC(=O)c3ccc(Cl)cc3)cc2)S1]

¹H-NMR (DMSO-d₆) δ: 12.02 (s, 1H), 8.03 (d, J=8.71 Hz, 2H), 7.65 (d, J=8.50 Hz, 2H), 7.15 (d, J=8.50 Hz, 2H), 6.92 (d, J=8.71 Hz, 2H), 5.54 (s, 2H), 4.88 (dd, J=9.12, 4.35 Hz, 1H), 3.33-3.29 (m, 1H), 3.05 (dd, J=14.10, 9.12 Hz, 1H).

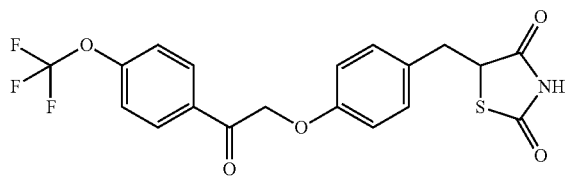 [SMILES: O=C1NC(=O)C(Cc2ccc(OCC(=O)c3ccc(OC(F)(F)F)cc3)cc2)S1]

¹H-NMR (CDCl₃) δ: 8.08 (m, 3H), 7.34 (d, J=8.09 Hz, 2H), 7.17 (d, J=8.71 Hz, 2H), 6.90 (d, J=8.71 Hz, 2H), 5.23 (s, 2H), 4.51 (dd, J=9.43, 3.84 Hz, 1H), 3.46 (dd, J=14.10, 3.94 Hz, 1H), 3.13 (dd, 14.20, 9.43 Hz, 1H), 1.60 (brs, 1H).

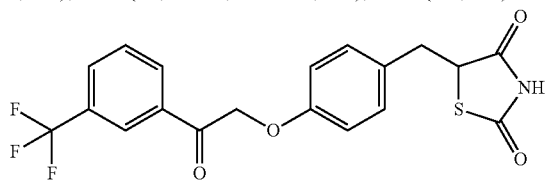

¹H-NMR (DMSO-d₆) δ: 12.20 (s, 1H), 8.30 (m, 2H), 8.07 (d, J=7.88 Hz, 1H), 7.82 (t, J=7.88 Hz, 1H), 7.16 (d, J=8.71 Hz, 2H), 6.95 (d, J=8.71 Hz, 2H), 5.64 (s, 2H), 4.88 (dd, J=9.33, 4.35 Hz, 1H), 3.34-3.29 (m, 1H), 3.06 (dd, J=14.10, 9.12 Hz, 1H).

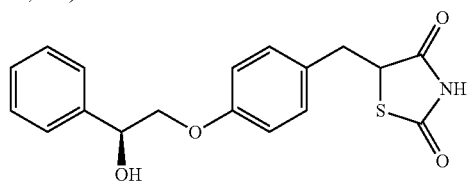

¹H-NMR (CDCl₃) δ: 8.42 (brs, 1H), 7.38 (m, 5H), 7.15 (d, J=8.50 Hz, 2H), 6.88 (d, J=8.50 Hz, 2H), 5.14 (dd, J=8.81, 3.01 Hz, 1H), 4.50 (dd, J=9.33, 3.94 Hz, 1H), 4.11 (m, 1H), 4.01 (t, J=9.23 Hz, 1H), 3.45 (dd, J=14.20, 3.84 Hz, 1H), 3.12 (dd, J=14.20, 9.43 Hz, 1H), 2.84 (brs, 1H).

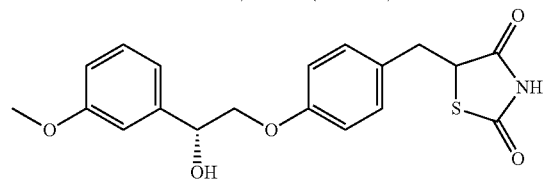

¹H-NMR (CDCl₃) δ: 8.35 (brs, 1H), 7.23 (t, J=8.09 Hz, 1H), 7.07 (d, J=8.71 Hz, 2H), 6.94 (m, 2H), 6.81 (m, 3H), 5.03 (dd, J=8.60, 2.80 Hz, 1H), 4.42 (dd, J=9.33, 3.94 Hz, 1H), 4.02 (m, 1H), 3.93 (t, J=9.23 Hz, 1H), 3.76 (s, 3H), 3.36 (dd, J=14.20, 3.84 Hz, 1H), 3.04 (dd, J=14.10, 9.33 Hz, 1H), 2.75 (brs, 1H).

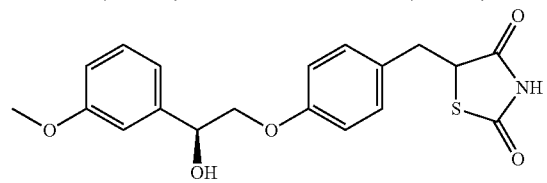

¹H-NMR (CDCl₃) δ: 8.42 (brs, 1H), 7.23 (t, J=7.98 Hz, 1H), 7.07 (d, J=8.71 Hz, 2H), 6.94 (m, 2H), 6.82-6.78 (m, 3H), 5.03 (dd, J=8.71, 2.90 Hz, 1H), 4.41 (dd, J=9.33, 3.94 Hz, 1H), 4.02 (m, 1H), 3.93 (t, J=9.12 Hz, 1H), 3.76 (s, 3H), 336 (dd, J=14.10, 3.94 Hz, 1H), 3.03 (dd, J=14.31, 9.33 Hz, 1H), 2.77 (brs, 1H).

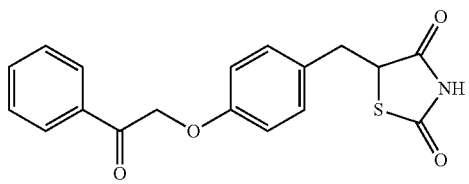

¹H-NMR (DMSO-d₆) δ: 12.03 (brs, 1H), 8.02 (m, 2H), 7.69 (t, J=7.36 Hz, 1H), 7.57 (t, J=7.67 Hz, 2H), 7.15 (d, J=8.50 Hz, 2H), 6.91 (d, J=8.50 Hz, 2H), 5.56 (s, 2H), 4.88 (dd, J=9.23, 4.25 Hz, 1H), 3.31 (m, 2H), 3.05 (dd, J=14.02, 9.23 Hz, 1H).

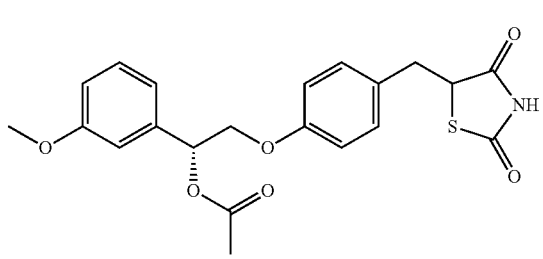 [SMILES: COc1cccc([C@H](COc2ccc(CC3SC(=O)NC3=O)cc2)OC(C)=O)c1]

¹H-NMR (CDCl₃): δ=8.57 (brs, 1H), 7.28 (m, 1H), 7.16 (m, 1H), 6.99 (m, 2H), 6.87 (m, 3H), 6.12 (dd, J=7.8, 3.6 Hz, 1H), 4.49 (dd, J=9.3, 3.9 Hz, 1H), 4.25 (m, 1H), 4.13 (dd, J=10.5, 3.6 Hz, 1H), 3.83 (s, 3H), 3.45 (dd, J=14.2, 3.8 Hz, 1H), 3.10 (dd, J=14.0, 9.6 Hz, 1H), 2.14 (s, 3H).

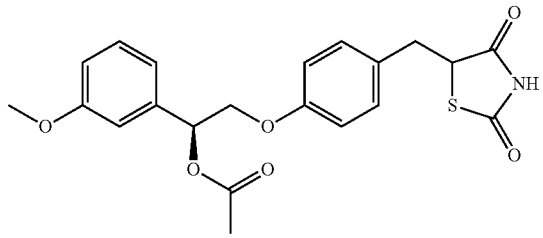 [SMILES: COc1cccc([C@@H](COc2ccc(CC3SC(=O)NC3=O)cc2)OC(C)=O)c1]

¹H-NMR (CDCl₃): δ=8.31 (brs, 1H), 7.29 (m, 1H), 7.17 (m, 1H), 6.99 (m, 2H), 6.88 (m, 3H), 6.12 (dd, J=7.8, 3.4 Hz, 1H), 4.50 (dd, J=9.4, 3.8 Hz, 1H), 4.25 (m, 1H), 4.13 (dd, J=10.4, 3.7 Hz, 1H), 3.83 (s, 3H), 3.45 (dd, J=14.2, 3.8 Hz, 1H), 3.11 (dd, J=14.1, 9.3 Hz, 1H), 2.14 (s, 3H).

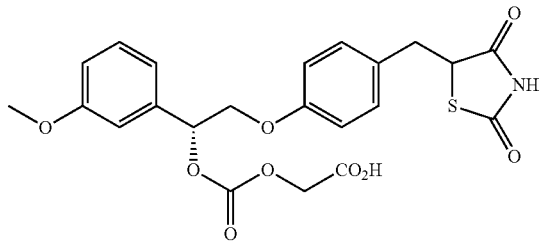 [SMILES: COc1cccc([C@H](COc2ccc(CC3SC(=O)NC3=O)cc2)OC(=O)OCC(=O)O)c1]

¹H-NMR (CDCl₃): δ=8.65 (m, 1H), 7.29 (m, 1H), 7.13 (m, 1H), 6.97 (m, 2H), 6.86 (m, 3H), 6.13 (m, 1H), 4.49 (dd, J=9.1, 3.9 Hz, 1H), 4.24 (m, 1H), 4.14 (m, 1H), 3.82 (s, 3H), 3.40 (m, 1H), 3.12 (dd, J=14.2, 9.0 Hz, 1H), 2.69 (m, 4H).

117

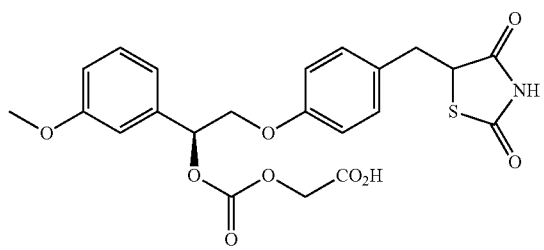

¹H-NMR (CDCl₃): δ=8.78 (brs, 1H), 7.29 (m, 1H), 7.13 (m, 1H), 6.97 (m, 2H), 6.85 (m, 3H), 6.12 (m, 1H), 4.47 (dd, J=8.8, 3.8 Hz, 1H), 4.20 (m, 2H), 3.81 (s, 3H), 3.36 (m, 1H), 3.13 (m, 1H), 2.68 (m, 4H).

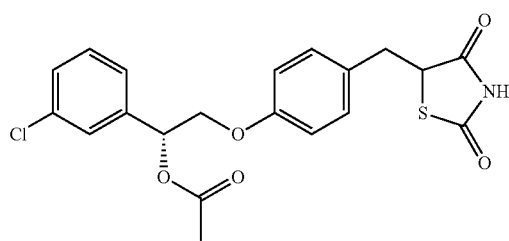 [SMILES: CC(=O)O[C@@H](COc1ccc(CC2SC(=O)NC2=O)cc1)c1cccc(Cl)c1]

¹H-NMR (CDCl₃): δ=8.74 (brs, 1H), 7.42 (s, 1H), 7.31 (m, 2H), 7.15 (d, J=8.7 Hz, 2H), 6.85 (d, J=8.7 Hz, 2H), 6.10 ((dd, J=7.4, 4.0 Hz, 1H), 4.50 (dd, J=9.3, 3.9 Hz, 1H), 4.24 (M, 1H), 4.13 (dd, J=10.4, 4.2 Hz, 1H), 3.45 (dd, J=14.1, 3.7 Hz, 1H), 3.10 (dd, J=14.0, 9.4 Hz, 1H), 2.15 (s, 3H).

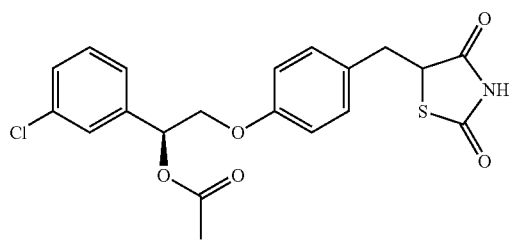 [SMILES: CC(=O)O[C@H](COc1ccc(CC2SC(=O)NC2=O)cc1)c1cccc(Cl)c1]

¹H-NMR (CDCl₃): δ=8.67 (brs, 1H), 7.42 (s, 1H), 7.30 (m, 2H), 7.15 (d, J=7.2 Hz, 2H), 6.85 (d, J=8.5 Hz, 2H), 6.10 (dd, J=7.4, 4.0 Hz, 1H), 4.50 (dd, J=9.3, 3.9 Hz, 1H), 4.24 (m, 1H), 4.13 (dd, J=10.4, 4.2 Hz, 1H), 3.45 (dd, J=14.2, 3.8 Hz, 1H), 3.11 (dd, J=14.2, 9.4 Hz, 1H), 2.15 (s, 3H).

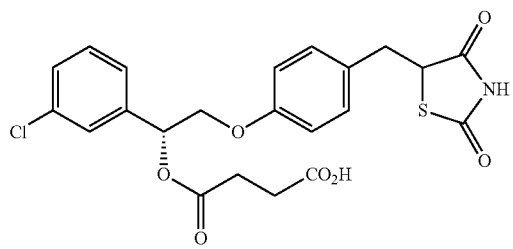 [SMILES: O=C(O)CCC(=O)O[C@@H](COc1ccc(CC2SC(=O)NC2=O)cc1)c1cccc(Cl)c1]

¹H-NMR (CDCl₃): δ=8.94, (d, J=4.8 Hz, 1H), 7.40 (s, 1H), 7.30 (m, 3H), 7.14 (d, J=8.5 Hz, 2H), 6.84 (d, J=8.5 Hz, 2H), 6.11 (m, 1H), 4.49 (dd, J=9.0, 3.8 Hz, 1H), 4.23 (m, 1H), 4.13 (m, 1H), 3.40 (dd, J=14.1, 3.5 Hz, 1H), 3.13 (dd, J=14.1, 9.1 Hz, 1H), 2.71 (m, 4H).

118

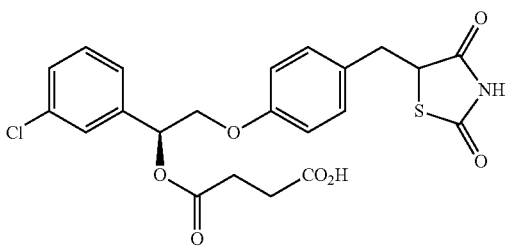 [SMILES: O=C(O)CCC(=O)O[C@H](COc1ccc(CC2SC(=O)NC2=O)cc1)c1cccc(Cl)c1]

¹H-NMR (CDCl₃): δ=8.88 (d, J=6.4 Hz, 1H), 7.40 (s, 1H), 7.30 (m, 3H), 7.14 (d, J=8.5 Hz, 2H), 6.84 (d, J=7.7 Hz, 2H), 6.11 (m, 1H), 4.49 (dd, J=9.1, 3.9 Hz, 1H), 4.24 (m, 1H), 4.14 (m, 1H), 3.40 (dd, J=14.3, 3.7 Hz, 1H), 3.13 (dd, J=14.2, 9.0 Hz, 1H), 2.70 (m, 4H).

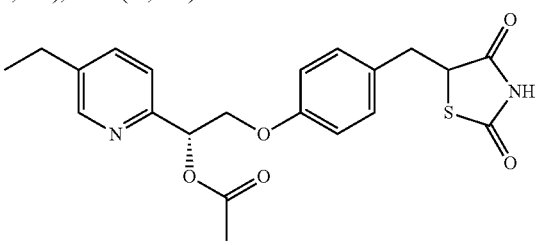

¹H-NMR (CDCl₃): δ=9.34 (brs, 1H), 8.46, s, 1H), 7.56 (dd, J=8.0, 2.0 Hz, 1H), 7.36 (d, J=8.0, 1H), 7.13 (d, J=7.1 Hz, 2H), 6.86 (d, J=8.6, 1.8 Hz, 2H), 6.18 (dd, J=6.4, 4.1 Hz, 1H), 4.48 (m, 1H), 4.41 (m, 1H), 3.44 (m, 1H), 3.09 (m, 1H), 2.67 (q, J=7.6 Hz, 2H), 2.15 (s, 3H), 1.26 (t, J=7.6 Hz, 3H).

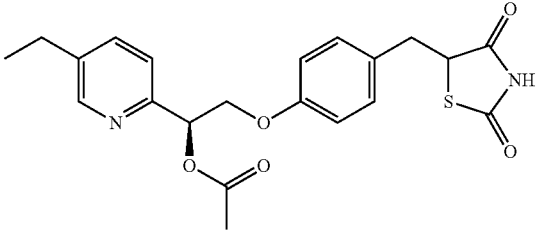 [SMILES: CCc1ccc([C@@H](COc2ccc(CC3SC(=O)NC3=O)cc2)OC(C)=O)nc1]

¹H-NMR (CDCl₃): δ=8.85 (brs, 1H), 8.46 (d, J=1.7 Hz, 1H), 7.56 (dd, J=8.0, 2.0 Hz, 1H), 7.37 (d, J=8.1 Hz, 1H), 7.13 (d, J=8.7 Hz, 2H), 6.86 (d, J=7.1 Hz, 2H), 6.19 (dd, J=6.4, 4.2 Hz, 1H), 4.49 (dd, J=9.1, 3.5 Hz, 1H), 4.41 (m, 2H), 3.44 (m, 1H), 3.10 (m, 1H), 2.67 (q, J=7.5 Hz, 2H), 2.16 (s, 3H), 1.26 (t, 3H).

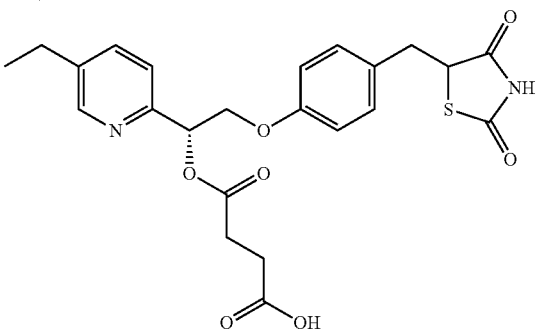 [SMILES: CCc1ccc([C@H](COc2ccc(CC3SC(=O)NC3=O)cc2)OC(=O)CCC(=O)O)nc1]

¹H-NMR (CDCl₃): δ=8.63 (brs, 1H), 8.45 (s, 1H), 7.77 (t, J=7.6 Hz, 1H), 7.56 (dd, J=7.9, 1.9 Hz, 1H), 7.10 (d, J=8.3 Hz, 2H), 6.83 (d, J=8.5 Hz, 2H), 6.19 (t, J=5.1 Hz, 1H), 4.46 (dd, J=9.0, 3.8 Hz, 1H), 4.39 (m, 2H), 3.38 (dd, J=14.2, 3.8 Hz, 1H), 3.10 (dd, J=14.2, 9.2 Hz, 1H), 2.68 (m, 6H), 1.24 (t, J=7.6 Hz, 3H).
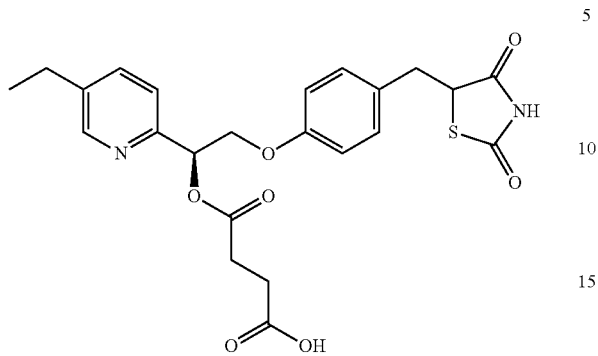
$^1$H-NMR (CDCl$_3$): δ=9.20 (brs, 1H), 8.48 (s, 1H), 7.60 (d, J=1.7 Hz, 1H), 7.40 (d, J=8.1 Hz, 1H), 7.12 (dd, J=8.5, 1.7 Hz, 2H), 6.84 (dd, J=8.7, 2.7 Hz, 2H), 6.20 (m, 1H), 4.49 (dd, J=8.3, 4.2 Hz, 1H), 4.40 (m, 2H), 3.33 (m, 1H), 3.18 (m, 1H), 2.71 (m, 6H), 1.25 (t, J=7.6 Hz), 3H).
Mass Spectra
| Structure | Calc. MW | Found MW |
|---|---|---|
| 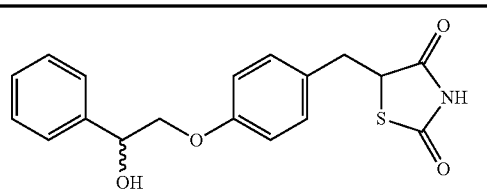 | 343.4 | ES+ 366.0 (M + Na)<br>ES− 342.1 (M − 1) |
| 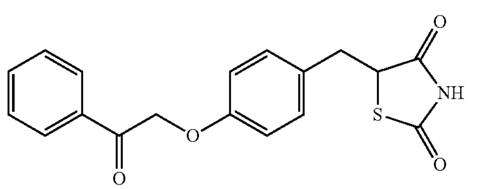 [SMILES: O=C1NC(=O)C(Cc2ccc(OCC(=O)c3ccccc3)cc2)S1] | 341.38 | ES+ 363.9 (M + Na)<br>ES− 340.0 (M − 1) |
| | 361.39 | ES− 360.1 (M − 1) |
| 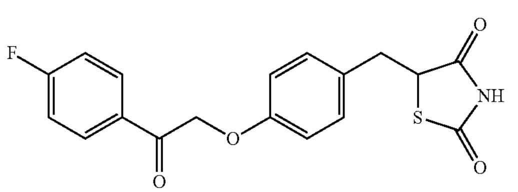 [SMILES: O=C1NC(=O)C(Cc2ccc(OCC(=O)c3ccc(F)cc3)cc2)S1] | 359.37 | ES+ 360.2 (M + 1)<br>ES− 358.2 (M − 1) |
| | 361.39 | ES− 360.1 (M − 1) |

| Structure | Calc. MW | Found MW |
|---|---|---|
| | 343.4 | ES− 342.2 (M − 1) |
| | 343.4 | ES− 342.1 (M − 1) |
| | 359.37 | ES− 358.0 (M − 1) |
| | 373.42 | ES− 372.1 (M − 1) |
| 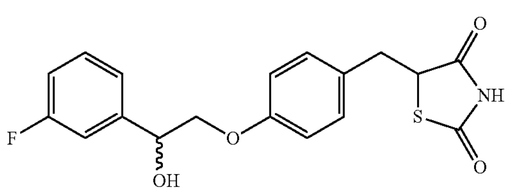 [SMILES: O=C1NC(=O)C(Cc2ccc(OCC(O)c3cccc(F)c3)cc2)S1] | 361.39 | ES+ 384.0 (M + Na)<br>ES− 360.1 (M − 1) |
| | 373.42 | ES− 372.0 (M − 1) |
| | 359.37 | ES− 358.2 (M − 1) |
| 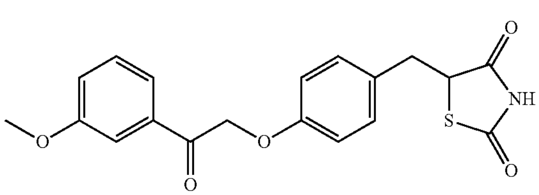 [SMILES: COc1cccc(C(=O)COc2ccc(CC3SC(=O)NC3=O)cc2)c1] | 371.41 | ES+ 372.0 (M + 1)<br>ES− 370.1 (M − 1) |

| Structure | Calc. MW | Found MW |
|---|---|---|
| 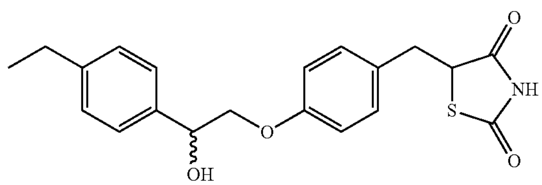 [SMILES: CCc1ccc(C(O)COc2ccc(CC3SC(=O)NC3=O)cc2)cc1] | 371.45 | ES− 370.2 (M − 1) |
| 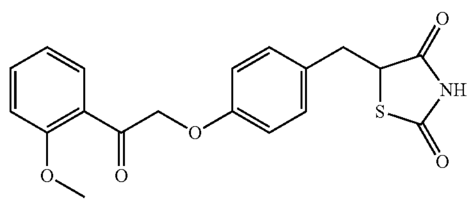 [SMILES: COc1ccccc1C(=O)COc1ccc(CC2SC(=O)NC2=O)cc1] | 371.41 | ES− 370.1 (M − 1) |
| 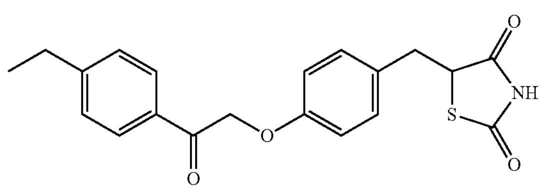 | 369.43 | ES+ 370.0 (M + 1)<br>ES− 368.1 (M − 1) |
| 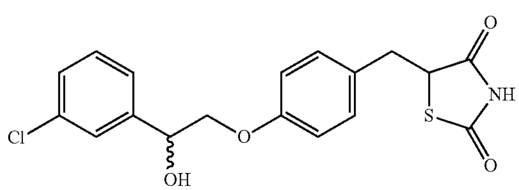 [SMILES: O=C1NC(=O)C(Cc2ccc(OCC(O)c3cccc(Cl)c3)cc2)S1] | 377.84 | ES− 376.0 (M − 1) |
| 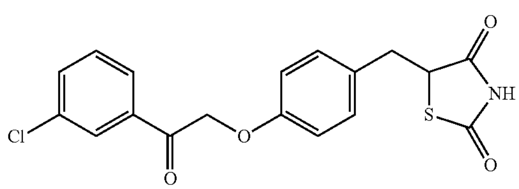 [SMILES: O=C1NC(=O)C(Cc2ccc(OCC(=O)c3cccc(Cl)c3)cc2)S1] | 375.83 | ES− 374.0 (M − 1) |
| 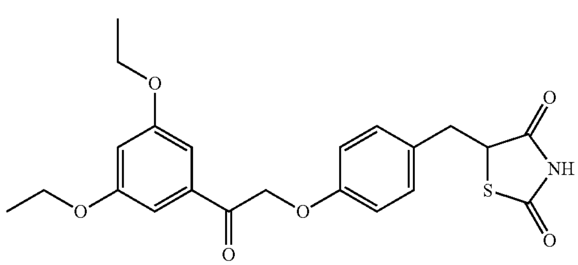 [SMILES: CCOc1cc(OCC)cc(C(=O)COc2ccc(CC3SC(=O)NC3=O)cc2)c1] | 429.49 | ES+ 430.1 (M + 1)<br>ES− 428.2 (M − 1) |
| 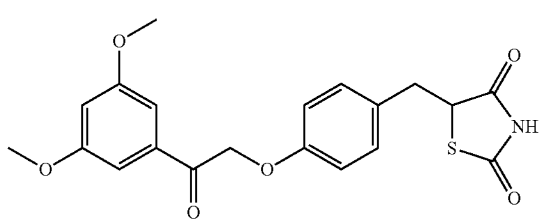 [SMILES: COc1cc(OC)cc(C(=O)COc2ccc(CC3SC(=O)NC3=O)cc2)c1] | 401.43 | ES+ 402.1 (M + 1)<br>ES− 400.2 (M − 1) |

-continued

| Structure | Calc. MW | Found MW |
|---|---|---|
| (3-trifluoromethoxyphenyl-C(O)-CH2-O-C6H4-CH2-thiazolidine-2,4-dione) | 425.38 | ES+ 426.0 (M + 1)<br>ES− 424.1 (M − 1) |
| (4-trifluoromethoxyphenyl-C(O)-CH2-O-C6H4-CH2-thiazolidine-2,4-dione) | 425.38 | ES+ 425.9 (M + 1)<br>ES− 424.2 (M − 1) |
| (3-chlorophenyl-CH(OH)-CH2-O-C6H4-CH2-thiazolidine-2,4-dione) | 377.84 | ES− 376.2 (M + 1) |
| (4-trifluoromethoxyphenyl-CH(OH)-CH2-O-C6H4-CH2-thiazolidine-2,4-dione) | 427.39 | ES− 426.3 (M+) |
| (4-methoxyphenyl-C(O)-CH2-O-C6H4-CH2-thiazolidine-2,4-dione) | 371.41 | ES− 370.2 (M − 1) |
| (4-chlorophenyl-C(O)-CH2-O-C6H4-CH2-thiazolidine-2,4-dione) | 375.83 | ES+ 376.2 (M + 1) |
| (3-trifluoromethylphenyl-C(O)-CH2-O-C6H4-CH2-thiazolidine-2,4-dione) | 409.38 | ES− 408.3 (M − 1) |
| (4-trifluoromethylphenyl-C(O)-CH2-O-C6H4-CH2-thiazolidine-2,4-dione) | 409.38 | ES− 408.1 (M − 1) |

-continued

| Structure | Calc. MW | Found MW |
|---|---|---|
| 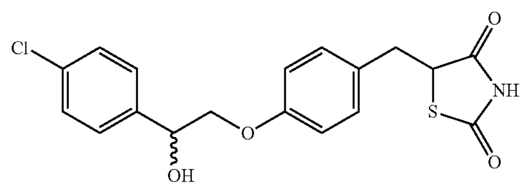 [SMILES: O=C1NC(=O)C(Cc2ccc(OCC(=O)c3ccc(Cl)cc3)cc2)S1] | 377.84 | ES− 376.1 (M − 1) |
| | 373.42 | ES− 372.1 (M − 1) |
| | 411.39 | ES− 410.2 (M − 1) |
| | 411.39 | ES− 410.2 (M − 1) |
| | 373.42 | ES− 372.1 (M − 1) |
| | 373.42 | ES− 372.1 (M − 1) |
| 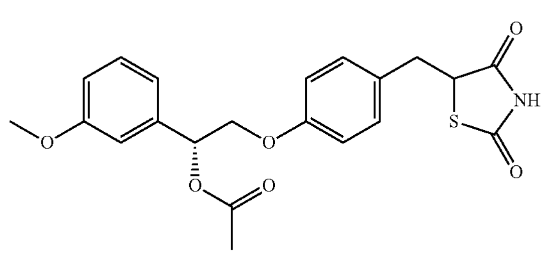 [SMILES: COc1cccc([C@H](COc2ccc(CC3SC(=O)NC3=O)cc2)OC(C)=O)c1] | 415.46 | ES− 414.10 (M − 1) |

-continued

| Structure | Calc. MW | Found MW |
|---|---|---|
| 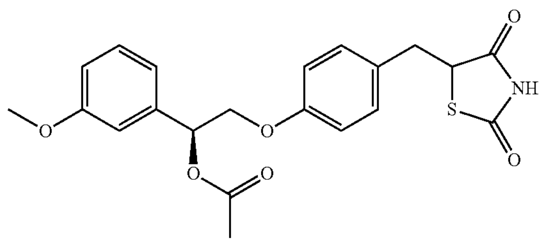 [SMILES: COc1cccc([C@@H](COc2ccc(CC3SC(=O)NC3=O)cc2)OC(C)=O)c1] | 415.46 | ES− 414.1 m/z (M − 1) |
| | 473.5 | ES− 472.0 m/z (M − 1) |
| | 473.5 | ES− 472.0 m/z (M − 1) |
| | 419.88 | ES− 418.0 m/z (M − 1) |
| | 419.88 | ES− 418 m/z (M − 1) |
| 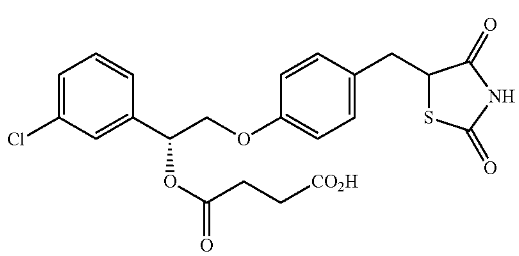 [SMILES: O=C(O)CCC(=O)O[C@@H](COc1ccc(CC2SC(=O)NC2=O)cc1)c1cccc(Cl)c1] | 477.19 | ES− 476.0 m/z (M − 1) |

| Structure | Calc. MW | Found MW |
|---|---|---|
| 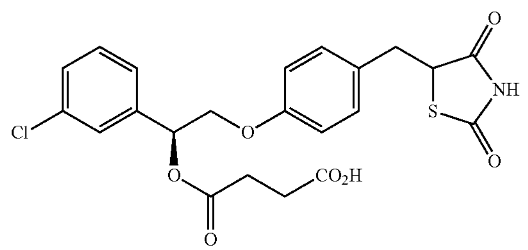 [SMILES: O=C(O)CCC(=O)O[C@H](COc1ccc(CC2SC(=O)NC2=O)cc1)c1cccc(Cl)c1] | 477.19 | ES− 476.0 m/z (M − 1) |
| | 414.47 | ES+ 415.0 m/z (M + 1); ES− 413.0 m/z (M − 1) |
| | 414.47 | ES+ 415.0 m/z (M − 1); ES− 413.0 m/z (M − 1) |
| | 472.51 | ES+ 473.0 m/z (M + 1); ES− 471.0 m/z (M − 1) |
| | 472.51 | ES+ 472.9 m/z (M + 1) ES− 471.0 m/z (M − 1) |

-continued

| Structure | Calc. MW | Found MW |
|---|---|---|
| 5-ethylpyridin-2-yl-C(O)-CH₂-O-C₆H₄-CH₂-(thiazolidine-2,4-dione) | 370.42 | ES+ 371.1 m/z (M + 1)<br>ES− 369.1 (M − 1) |
| 5-ethylpyridin-2-yl-CH(OH)-CH₂-O-C₆H₄-CH₂-(thiazolidine-2,4-dione), (S) | 372.11 | ES+ 373.1 m/z (M + 1)<br>ES− 371.1 (M − 1) |
| 5-ethylpyridin-2-yl-CH(OH)-CH₂-O-C₆H₄-CH₂-(thiazolidine-2,4-dione), (R) | 372.11 | ES+ 373.0 m/z (M + 1)<br>ES− 371.1 (M − 1) |
| 5-ethylpyridin-2-yl-CH₂CH₂-O-C₆H₄-CH₂-(5-methyl-thiazolidine-2,4-dione) | 370.47 | ES+ 371.2 m/z (M + 1)<br>ES− 369.2 (M − 1) |
| 5-ethylpyridin-2-yl-CH(OH)-CH₂-O-C₆H₄-CH₂-(5-methyl-thiazolidine-2,4-dione), racemic | 386.46 | ES+ 387.3 m/z (M + 1)<br>ES− 385.3 (M − 1) |
| 5-ethylpyridin-2-yl-CH₂CH₂-O-C₆H₄-CH₂-(5-methyl-thiazolidine-2,4-dione) (+)-enantiomer | 370.47 | ES+ 371.2 m/z (M + 1)<br>ES− 369.2 (M − 1) |
| 5-ethylpyridin-2-yl-CH₂CH₂-O-C₆H₄-CH₂-(5-methyl-thiazolidine-2,4-dione) (−)-enantiomer | 370.47 | ES+ 371.2 m/z (M + 1)<br>ES− 369.2 (M − 1) |
| 5-ethylpyridin-2-yl-CH(OH)-CH₂-O-C₆H₄-CH₂-(5-methyl-thiazolidine-2,4-dione), (S) | 386.46 | ES+ 387.3 m/z (M + 1)<br>ES− 385.3 (M − 1) |

-continued

| Structure | Calc. MW | Found MW |
|---|---|---|
| [structure: 5-ethylpyridin-2-yl with CH(OH)CH2O-phenyl-CH2-thiazolidine-2,4-dione] | 386.46 | ES+ 387.2 m/z (M + 1)<br>ES− 385.2 (M − 1) |
| [structure: 5-ethylpyridin-2-yl with C(=O)CH2O-phenyl-CH2-thiazolidine-2,4-dione] | 384.45 | ES+ 385.1 m/z (M + 1)<br>ES− 383.1 (M − 1) |
| [structure: 5-ethylpyridin-2-yl with CH(OH)CH2O-phenyl-CH2-thiazolidine-2,4-dione] | 386.46 | ES+ 373.2 (M + 1)<br>ES− 371.2 (M − 1) |

Example 10A

Preparation of Acid Salts of Compounds of Formula I

A compound of Formula I may be converted to a salt by dissolving the compound in a solvent in which the acid salt of the organic compound is insoluble or is only sparingly soluble; adding one or more molar equivalents of an acid, such as HCl, HBr, acetic acid, trifluoroacetic acid, or $H_2SO_4$, methane sulfonic acid, p-toluene sulfonic acid, trifluoromethanesulfonic acid, or the like, to the solvent containing the dissolved compound of Formula I to form a precipitate of the organic compound salt; and collecting the precipitate using filtration, decanting or some similar method to produce the salt of the organic compound of Formula I in a pure form.

Example 10A1

5-{4-[2-(5-ethylpyridin-2-yl)-2-oxoethoxy]benzyl}-1,3-thiazolidine-2,4-dione hydrochloride 1M solution of HCl in EtOH was prepared by diluting 0.70 ml acetyl chloride (10 mmol) to 10 ml with anhydrous EtOH. Suspended 5-((4-(2-(5-ethyl-2-pyridyl)-1-oxoethoxy)phenyl)methyl)-2,4-thiazolidinedione (Compound A) (100 mg, 0.27 mmol) in anhydrous EtOH (5 ml) and heated with heat gun until all solids dissolved. Added 0.27 ml of the 1M solution of HCl in EtOH. Stirred for 2 hours at RT. Evaporated in vacuo (ca. 50° C.) for 2 hours to give of yellow solid, (110 mg).

Analytical Calc. for $C_{19}H_{19}ClN_2O_4S$ plus 5.25% $H_2O$: C, 53.14; H, 5.05; N, 6.52; Cl, 8.26. Found: C, 53.48; H, 4.98; N, 6.26; Cl, 8.62.

Example 10A2

5-{4-[2-(5-ethylpyridin-2-yl)-2-oxoethoxy]benzyl}-1,3-thiazolidine-2,4-dione sulfate 5-{4-[2-(5-ethylpyridin-2-yl)-2-oxoethoxy]benzyl}-1,3-thiazolidine-2,4-dione (Compound A) (100 mg, 0.27 mmol) was suspended in anhydrous abs. EtOH (3 ml) and the mixture was heated with a heat gun until all solids dissolved. Added 1M aq. $H_2SO_4$ (0.27 ml, commercial stock solution). Stirred for 1 hour at RT. Evaporated in vacuo and dried under high vac. (ca. 50° C.) for 2 hours to give a yellow oil (130 mg).

Analytical Calc. for $C_{19}H_{18}N_2O_4S$ plus 5.12% $H_2O$ and 25.07% $H_2O_4S$: C, 43.21; H, 4.49; N, 5.30; S, 14.27. Found: C, 43.30; H, 4.46; N, 4.96; S, 14.16.

Example 10B

Preparation of Alkali Earth Metal Salts of Compounds of Formula I

A compound of Formula I may be converted to a salt by dissolving the compound in a solvent in which the alkali earth metal salt of the organic compound is insoluble or is only sparingly soluble; adding one or more molar equivalents of a base, such as NaOH, KOH, or the like, to the solvent containing the dissolved compound of Formula I to form a precipitate of the organic compound salt; and collecting the precipitate using filtration, decanting or some similar method to produce the salt of the organic compound of Formula I in a pure form.

Alternatively, a compound of Formula I may be converted to a salt by dissolving the compound in a solvent in which the salt of the organic compound is also soluble; adding one or more molar equivalents of a base with a relatively low boiling point, such as NaOH, KOH, or the like, to the solvent containing the dissolved compound of Formula I; and then evaporating the solvent and any excess base contained in the solution to produce the salt of the organic compound in a pure form.

Example 10B1

Sodium 5-{4-[2-(5-ethylpyridin-2-yl)-2-oxoethoxy]benzyl}-2,4-dioxo-1,3-thiazolidin-3-ide 5-{4-[2-(5-ethylpyridin-2-yl)-2-oxoethoxy]benzyl}-1,3-thiazolidine-2,4-dione (100 mg, 0.27 mmol) was suspended in anhydrous abs. EtOH (3 ml) and the mixture was heated with a heat gun until all solids dissolved. Added sodium ethoxide (18 mg, 0.27 mmol). Stirred for 1 hour. Evaporated in vacuo and dried under high vac. (ca. 50° C.) for 2 hours to give a white solid (110 mg, 100%).

Analytical Calc. for $C_{19}H_{17}N_2NaO_4S$ plus 2.38% $H_2O$: C, 56.77; H, 4.53; N, 6.97. Found: C, 57.08; H, 4.33; N, 6.85.

Example 10B2

Potassium 5-{4-[2-(5-ethylpyridin-2-yl)-2-oxoethoxy]benzyl}-2,4-dioxo-1,3-thiazolidin-3-ide 5-{4-[2-(5-ethylpyridin-2-yl)-2-oxoethoxy]benzyl}-1,3-thiazolidine-2,4-dione (100 mg, 0.27 mmol) in THF (3 ml) was added a 1M solution of potassium tert-butoxide in THF (0.27 ml, 0.27 mmol). Stirred at RT for 2 hours. Evaporated in vacuo. Dried under high vac. (ca. 50° C.) for 2 hours to give a salmon-colored solid (110 mg, 100%).

Analytical Calc. for $C_{19}H_{17}KN_2O_4S$ plus 2.88% $H_2O$ and 7.95% KOH: C, 49.74; H, 4.21; N, 6.11. Found: C, 49.98; H, 3.79; N, 5.90.

Example 10B3

Sodium 5-{4-[2-(3-methoxyphenyl)-2-oxoethoxy]benzyl}-2,4-dioxo-1,3-thiazolidin-3-ide 5-{4-[2-(3-methoxyphenyl)-2-oxoethoxy]benzyl}-1,3-thiazolidine-2,4-dione (100 mg, 0.27 mmol) was suspended in THF (3 ml) and the mixture was heated with a heat gun until all solids dissolved. Added sodium tert-butoxide (26 mg, 0.27 mmol). Stirred at RT for 2 hours. Evaporated in vacuo. Dried under high vac. (ca. 50° C.) for 2 hours to give an off-white solid (110 mg, 100%).

Analytical Calc. for $C_{19}H_{16}NNaO_5S$ plus 1.60% $H_2O$: C, 57.08; H, 4.21; N, 3.50. Found: C, 56.91; H, 4.01; N, 3.30.

Example 10B4

Potassium 5-{4-[2-(3-methoxyphenyl)-2-oxoethoxy]benzyl}-2,4-dioxo-1,3-thiazolidin-3-ide A stirring suspension of 5-{4-[2-(3-methoxyphenyl)-2-oxoethoxy]benzyl}-1,3-thiazolidine-2,4-dione in THF (3 ml) was heated with a heat gun until all solids dissolved. Added a 1M solution of potassium tert-butoxide in THF (0.27 ml, 0.27 mmol). Stirred for 2 hours at RT. Evaporated in vacuo. Dried under high vac (ca. 50° C.) for 2 hours to give a salmon-colored solid (110 mg, 100%).

Analytical Calc. for $C_{19}H_{16}K_1N_1O_5S$ plus 2.50% $H_2O$ and 7.96% KOH: C, 49.84; H, 3.96; N, 3.06. Found: C, 49.65; H, 3.58; N, 3.07.

Example 10B5

Potassium 5-{4-[2-(3-methoxyphenyl)-2-oxoethoxy]benzyl}-2,4-dioxo-1,3-thiazolidin-3-ide A mixture of methanol (1.0 lit) and potassium hydroxide flakes (85% w/w) (35.5 gm, 0.539 mol) is stirred to get a clear solution at 25-30° C. To this solution is added 5-{4-[2-(3-methoxyphenyl)-2-oxoethoxy]benzyl}-1,3-thiazolidine-2,4-dione (200 gm, 0.539 mol) in single lot under stirring along with methanol (200 ml). A clear solution is formed and precipitate begins to form within 10-15 min. Stirred the reaction mixture for 6 hr. Filtered the solid obtained and washed with methanol (200 ml) and dried in oven at 50-55° C. to yield potassium salt of 5-{4-[2-(3-methoxyphenyl)-2-oxoethoxy]benzyl}-1,3-thiazolidine-2,4-dione (185 gm).

Example 10C

Characterization of Metal Salts of Compounds of Formula I

Metal salts of compounds of Formula I were characterized using XRPD, DSC, thermogravimetry, and moisture sorption analyses. Note that XRPD patterns described below, and provided in FIGS. 1 and 5 were obtained using a Bruker Model D8 X-Ray Diffractometer. Thermogravimetric analyses, DSC analyses, and moisture sorption analyses were performed using a TA Instruments Universal V4.4A instrument.

Example 10C1

Figure 2:
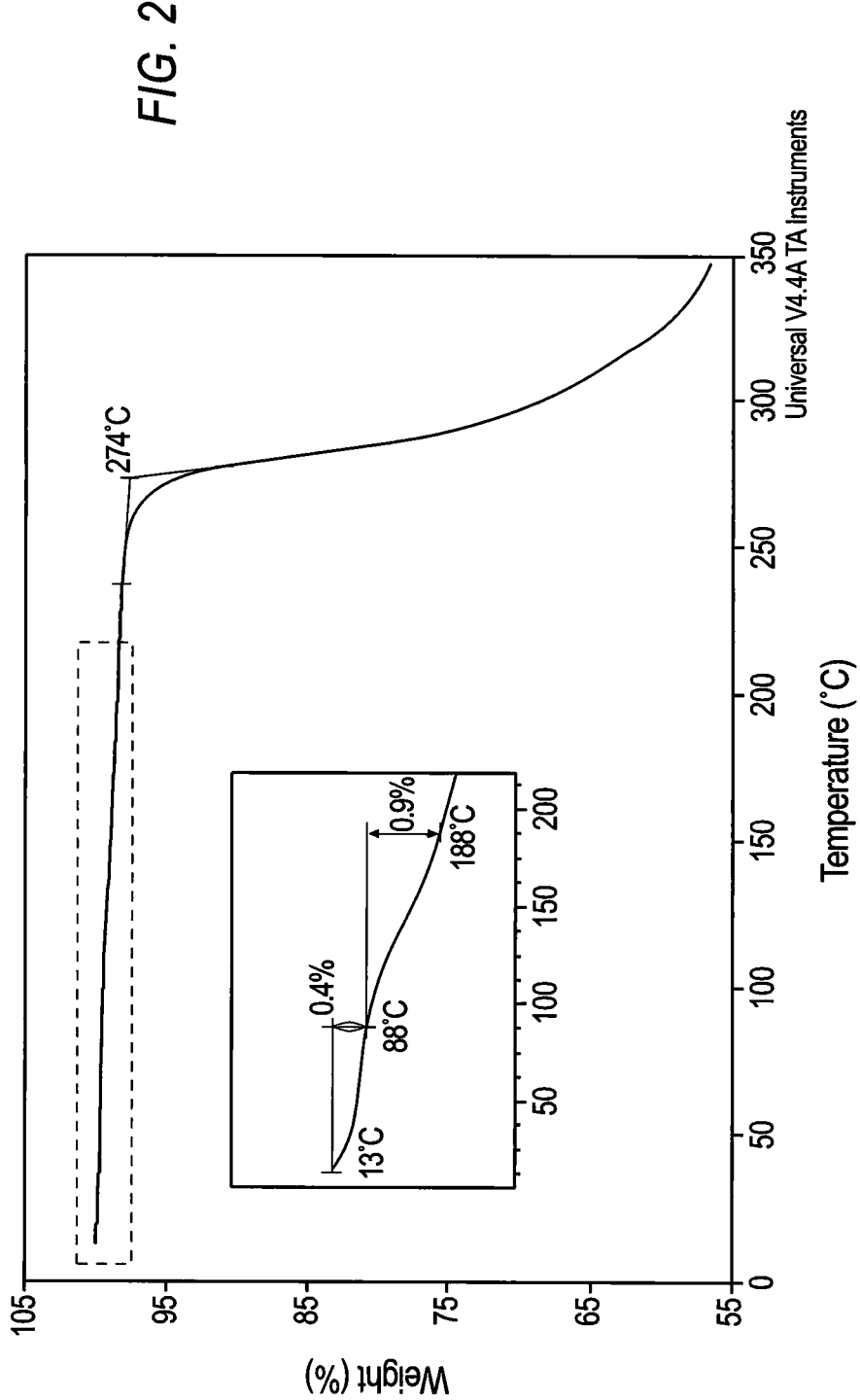
FIG. 2 is a graph of weight (%) as a function of temperature for a sodium salt of a compound of Formula I under thermogravimetric analysis.
Figure 3:
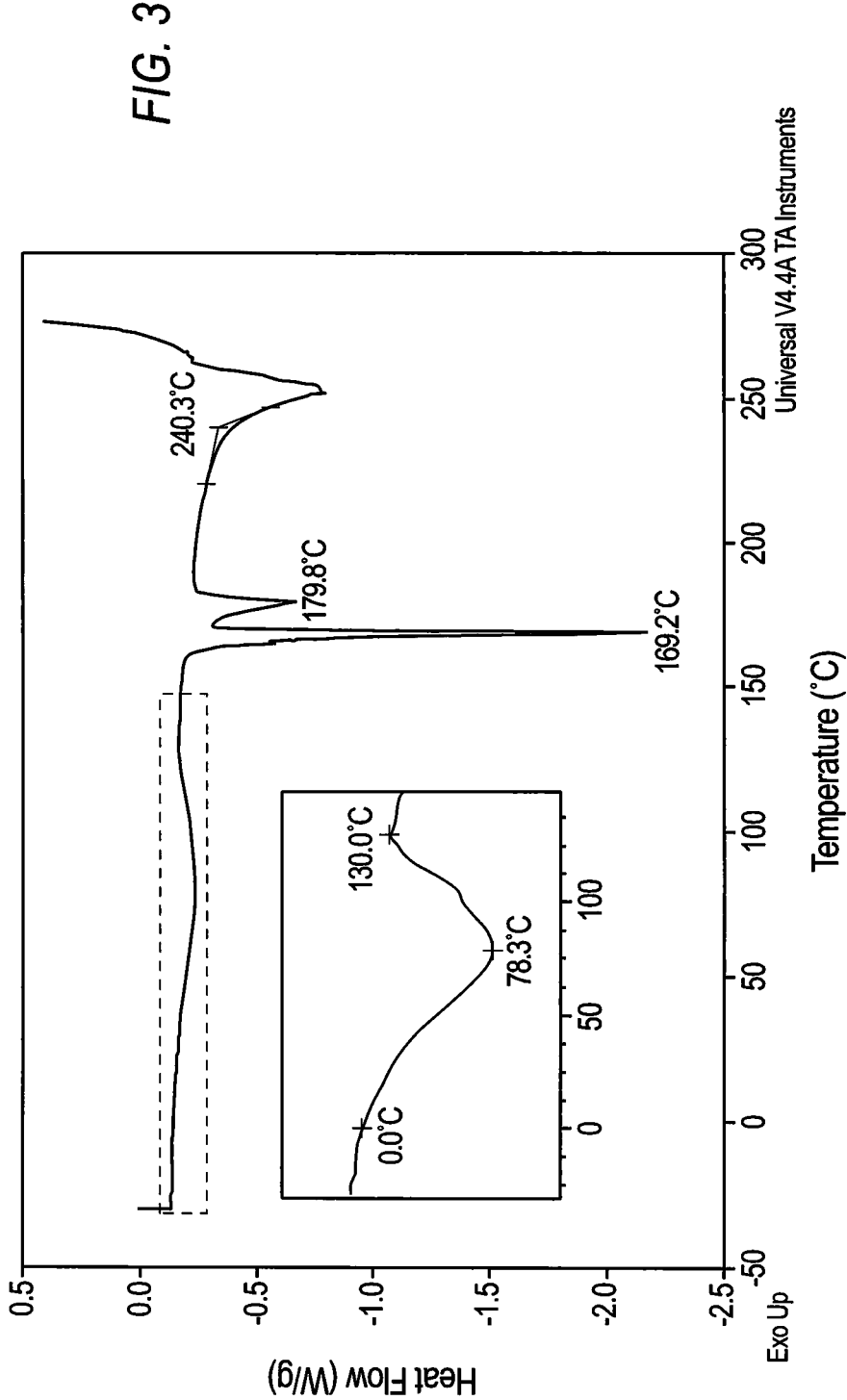
FIG. 3 is a graph of heat flow as a function of temperature for a sodium salt of a compound of Formula I under DSC analysis.
Figure 4:
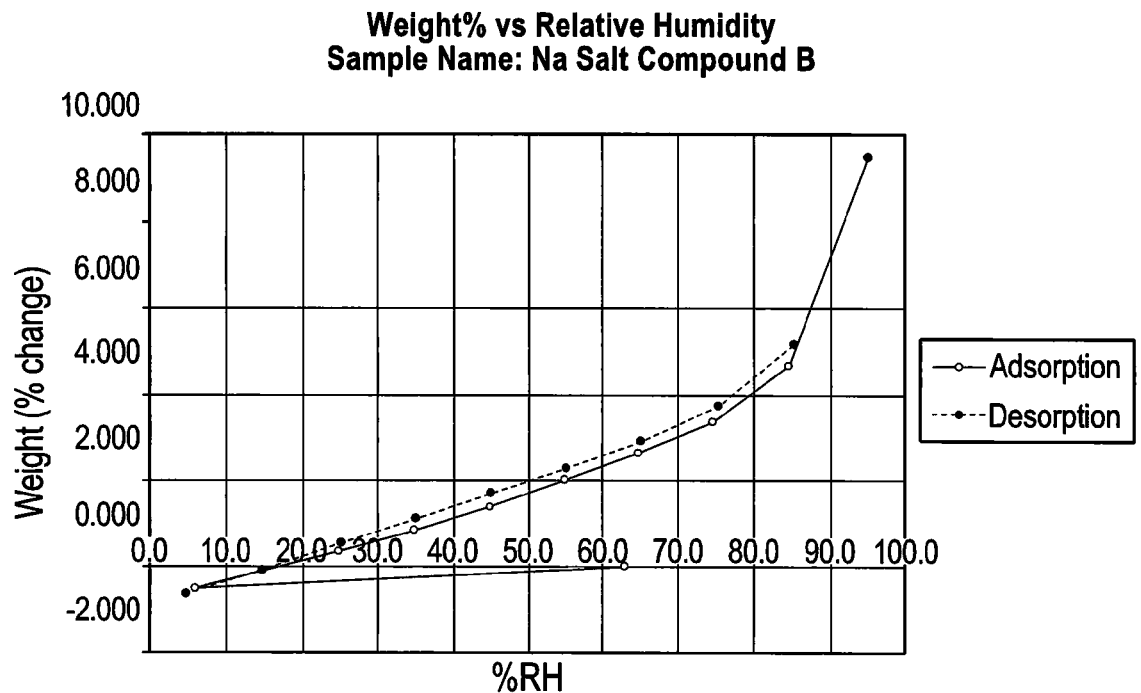
FIG. 4 is a graph of weight change (%) as a function of percent relative humidity for a sodium salt of a compound of Formula I under moisture sorption analysis.

Characterization of Sodium Salt of 5-{4-[2-(3-methoxyphenyl)-2-oxoethoxy]benzyl}-1,3-thiazolidine-2,4-dione FIG. 1 provides the XRPD pattern of a sample of a sodium salt of Compound B Referring to FIGS. 2-4, thermogravimetric, DSC, and moisture sorption analyses were performed on a sodium salt of Compound B. Thermogravimetric analysis was conducted using 7.5450 mg of the sodium salt and an instrument setting of 10° C./min. The DSC analysis was performed using a 2.00 mg sample of the sodium salt and an instrument setting of 10° C./min. The moisture sorption analysis was performed on 14.07 mg of sodium salt over a relative humidity range of 5% to 95% at 25° C. with 180 minute max. equilibration time and data sampling every 2 minutes.

It is noted that the sodium salt was produced as a single polymorph.

Example 10B6a

Figure 5:
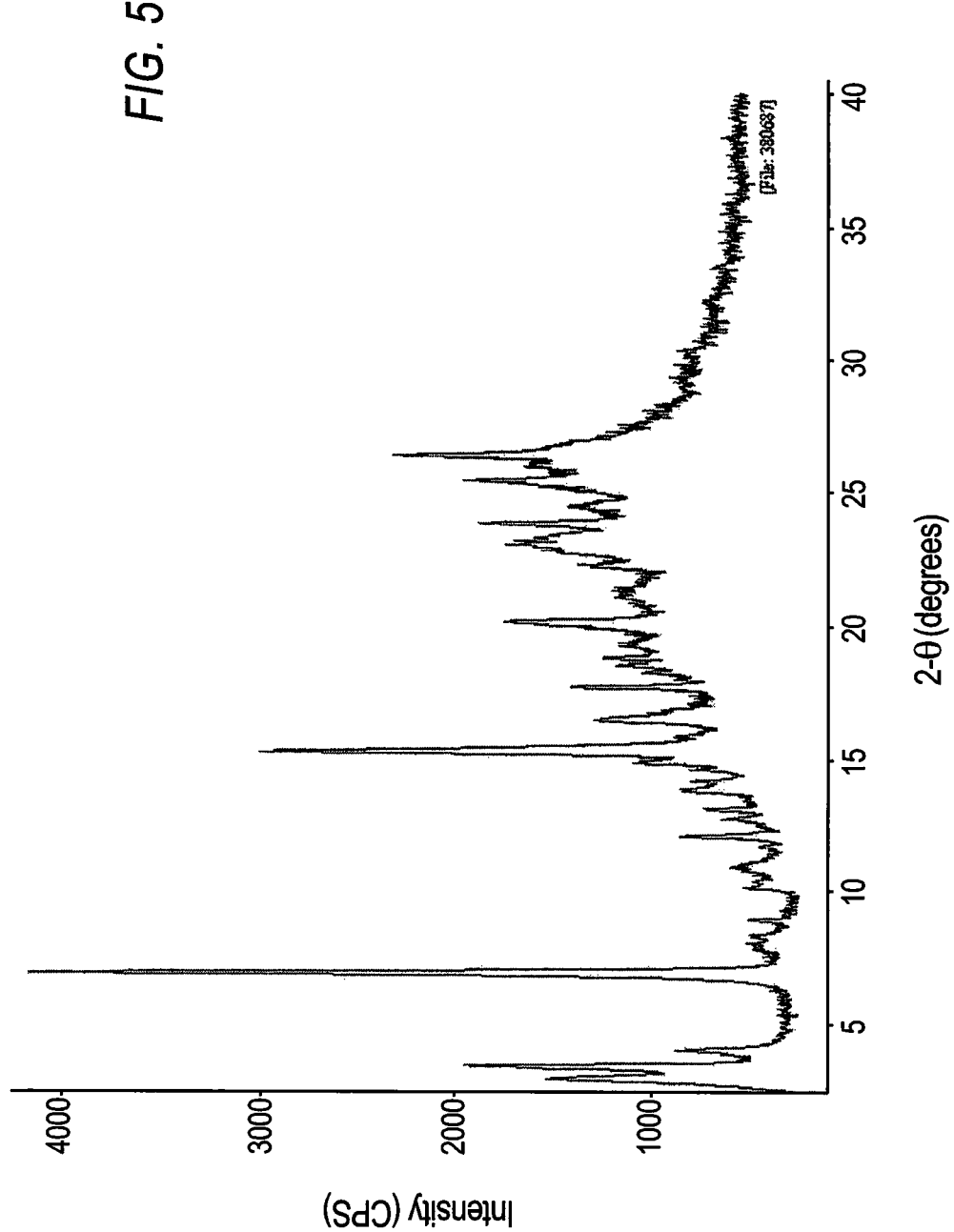
FIG. 5 is an XRPD pattern for a potassium salt of a compound of Formula I.
Figure 6:
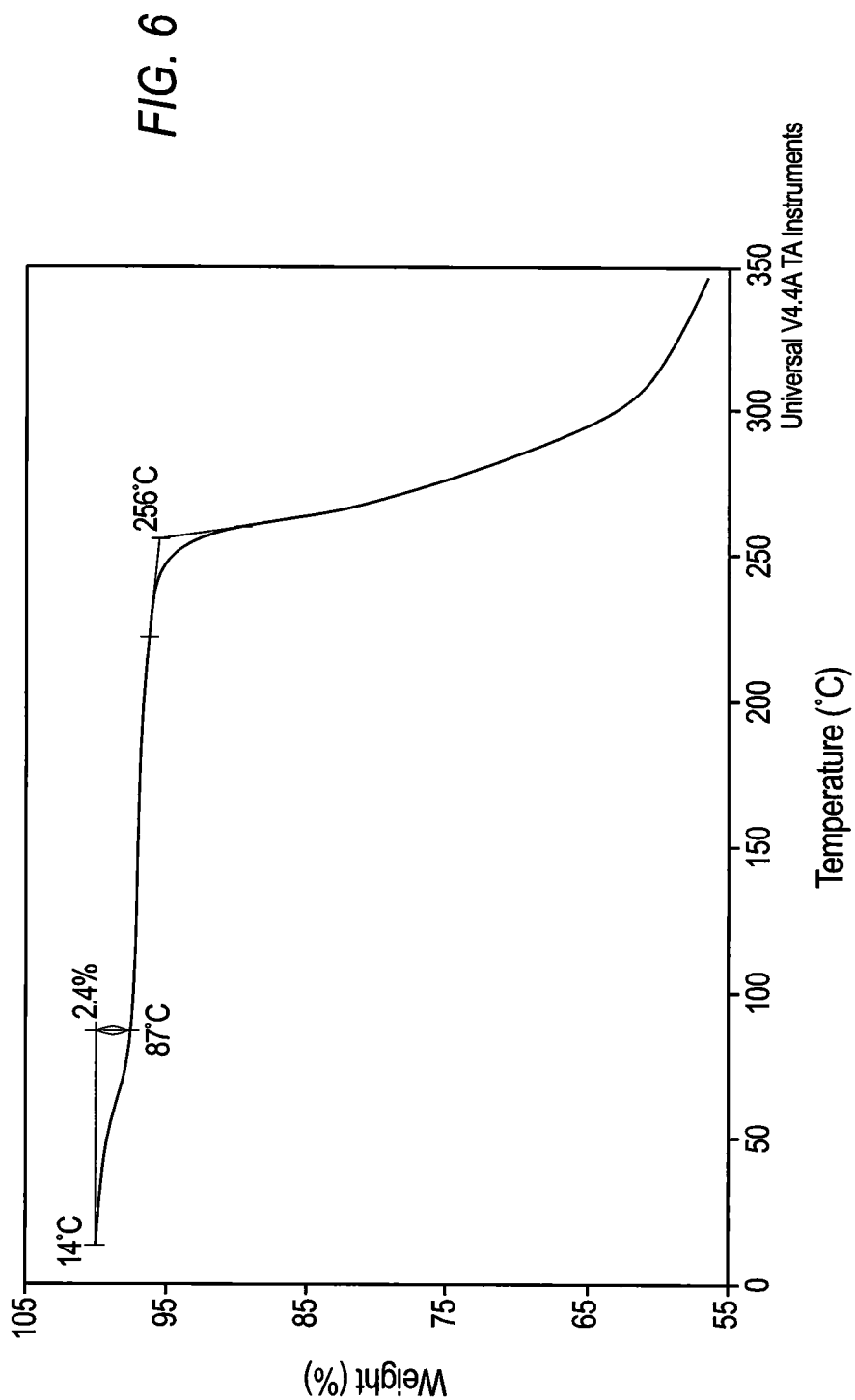
FIG. 6 is a graph of weight (%) as a function of temperature for a potassium salt of a compound of Formula I under thermogravimetric analysis.
Figure 7:
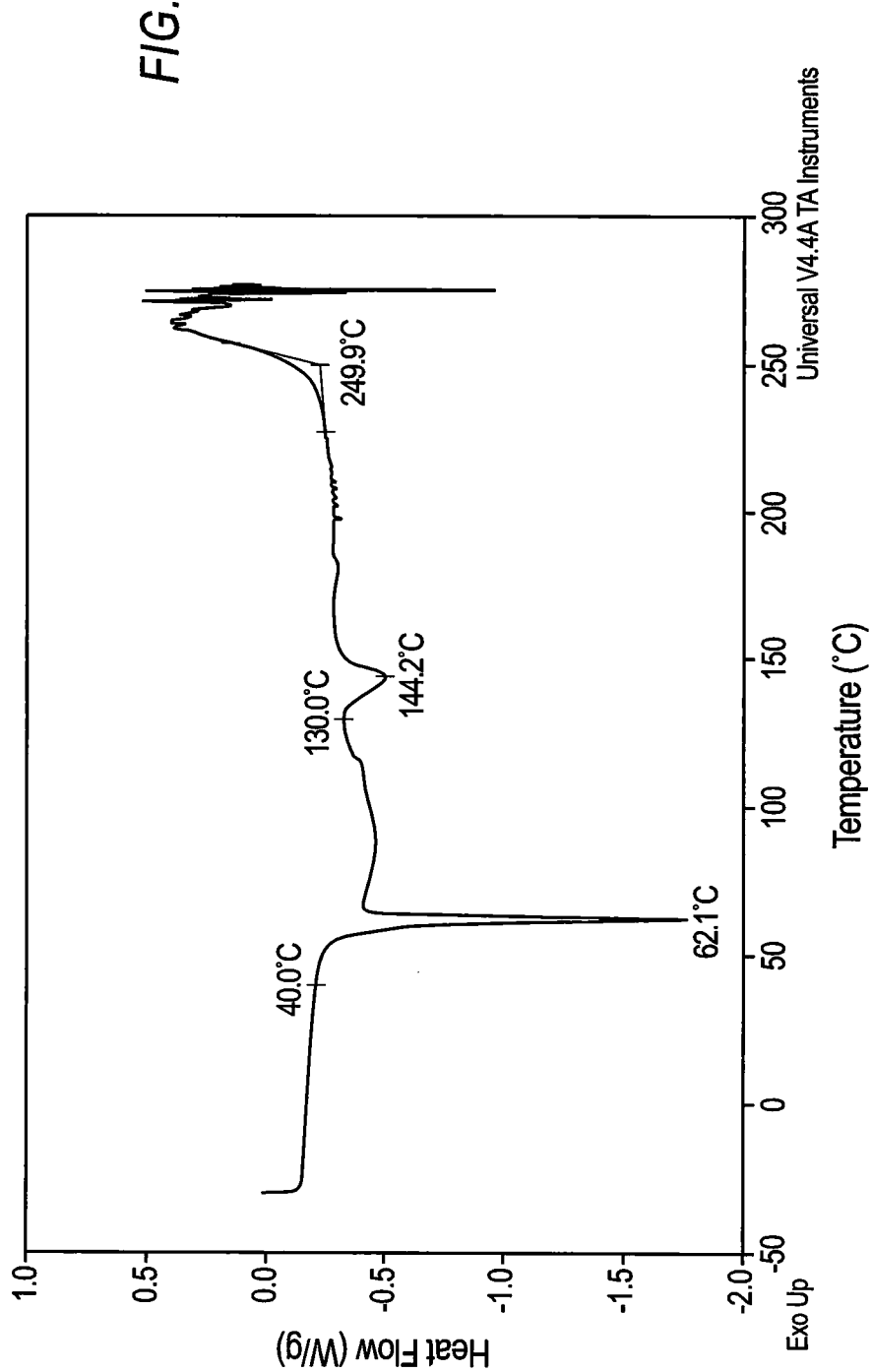
FIG. 7 is a graph of heat flow as a function of temperature for a potassium salt of a compound of Formula I under DSC analysis.
Figure 8:
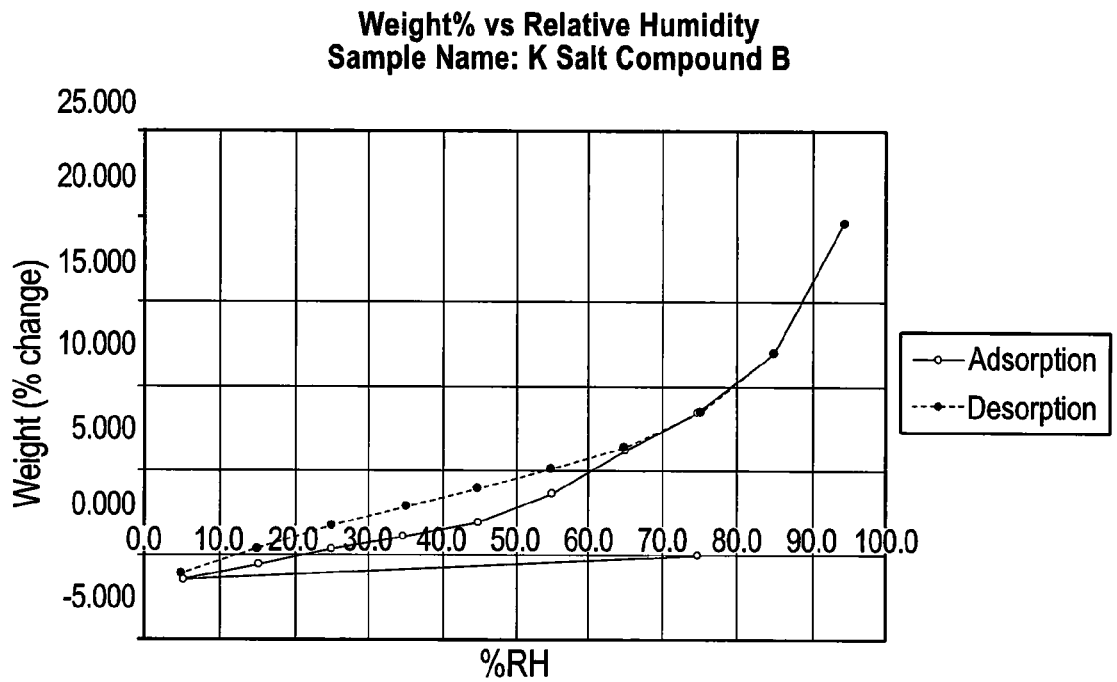
FIG. 8 is a graph of weight change (%) as a function of percent relative humidity for a potassium salt of a compound of Formula I under moisture sorption analysis.

Characterization of a Potassium Salt of 5-{4-[2-(3-methoxyphenyl)-2-oxoethoxy]benzyl}-1,3-thiazolidine-2,4-dione FIG. 5 provides the XRPD pattern of a sample of a potassium salt of Compound B Referring to FIGS. 6-8, thermogravimetric, DSC, and moisture sorption analyses were performed on a potassium salt of Compound B. Thermogravimetric analysis was conducted using 15.9290 mg of the potassium salt and an instrument setting of 10° C./min. The DSC analysis was performed using a 4.66 mg sample of the sodium salt and an instrument setting of 10° C./min. The moisture sorption analysis was performed on 12.934 mg of sodium salt over a relative humidity range of 5% to 95% at 25° C. with 180 minute max. equilibration time and data sampling every 2 minutes.

The data for the sodium and potassium salts of Compound B are consistent with crystalline materials showing significant hygroscopicity. The sodium salt exhibited a ~10.0 wt % progressive moisture uptake between ~6% and ~95% RH. A ~21.1 wt % water uptake was observed for the potassium salt upon increasing relative humidity from ~5% to ~95% RH.

Example 11

Biological Properties of Compound Salts

Example 11A

Bioavailability of Sodium Salt of Compound A

Figure 9:
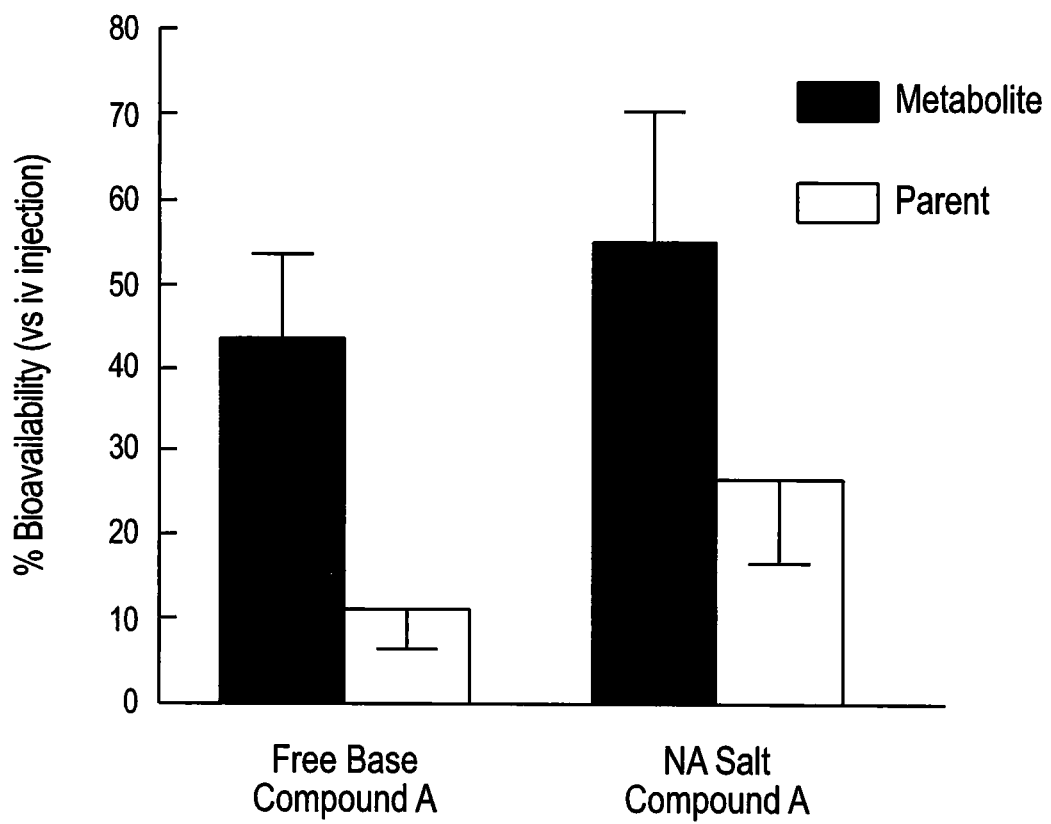
FIG. 9 is a graph comparing bioavailability of Compound A and its metabolite to sodium salts thereof.

Referring to FIG. 9, the bioavailability of the sodium salt of Compound A was evaluated by crossover design in 4 male cynomolgus monkeys having weights ranging from 4.52 to 5.12 kg. The monkeys fasted overnight and were dosed by oral gavage washed down with 10 ml tap water. Blood samples were taken at 0.25, 0.5, 1, 2, 3, 4, 6, 9, 12, 24, and 48 hours after a single dosage was administered and assayed for drug related materials with a LCMS assay using an internal standard. 90 mg of drug was put in 00 gelatin capsules containing 90 mg of free base equivalents. This was compared to an iv injection of 2 ml/kg and 45 mg of free base solution in 50% hydroxypropyl b-cyclodextran. The absolute availability versus an iv injection was determined for both parent compound and major metabolite. It is noted that the sodium salt of Compound A, for both the metabolite and the parent compound, had significantly higher bioavailability that their free base counterparts.

Example 11B

Bioavailability of Potassium and Sodium Salts of Compound B

Figure 10:
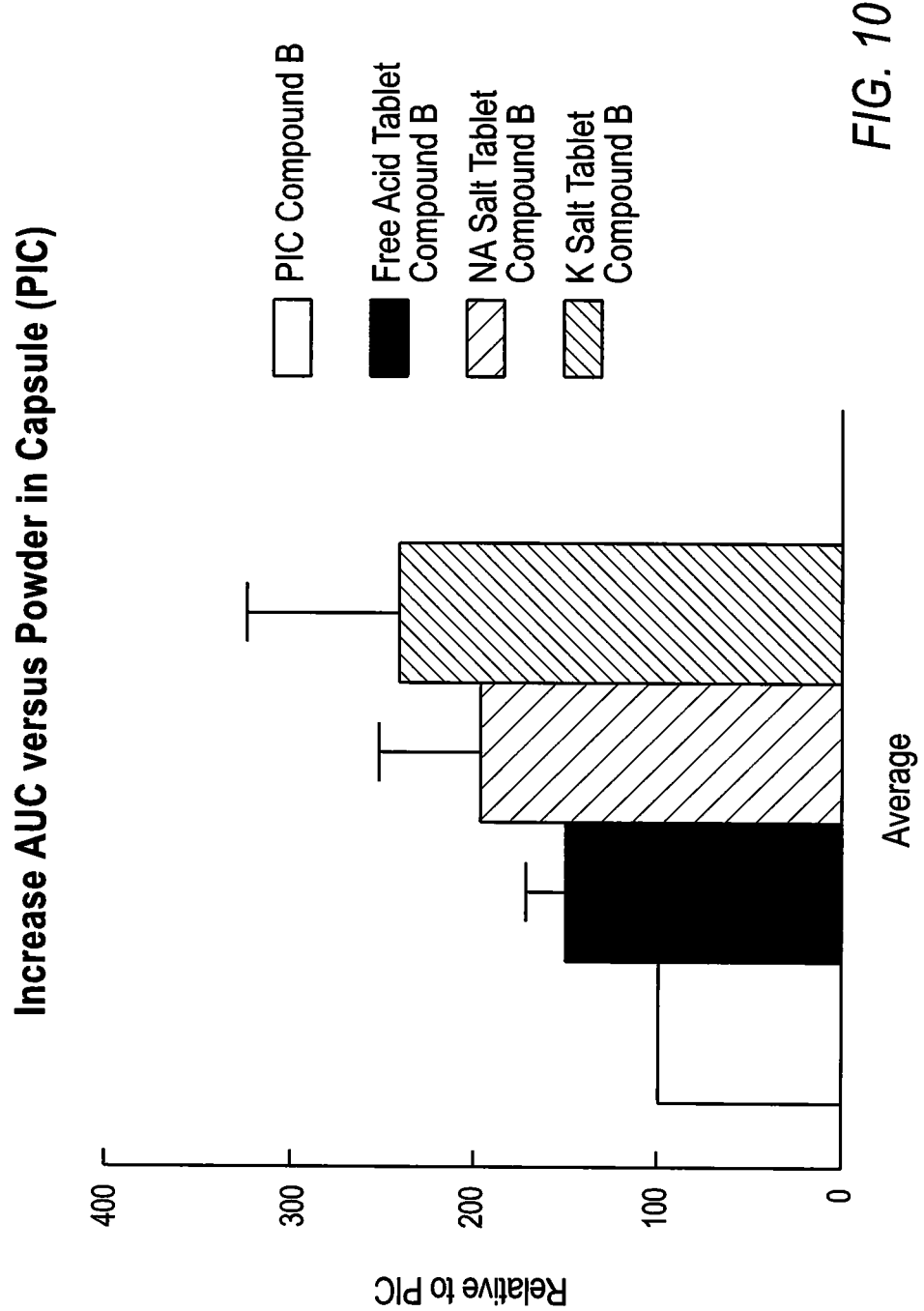
FIG. 10 is a graph of the area under the curve (AUC) of Compound B and its metal salts.

Referring to FIG. 10, the area under the curve (AUC) of compound related materials was compared following dosing of 250 mg of Compound B as powder in capsules of free acid (PIC), formulated tablets of micronized free acid, or formulated tablets of the Na or K salt of Compound B given at the same free acid equivalents. (N=4 cynomolgus monkeys). The formulated, compressed tablet also contained in each case approximately 40.5% lactose, 16.8% microcrystalline cellulose, 1.9% Croscarmellose sodium, 0.5% colloidal silicon dioxide, and 0.9% magnesium stearate. It is noted that both the sodium and potassium salts of Compound B had significantly higher bioavailability that their free acid counterparts. Also, the salts of the bulk acid showed great advantage over the compressed tablet with micronized free acid.

Example 11C

Pharmacological Activity of Sodium Salt of Compound A

Figure 11:
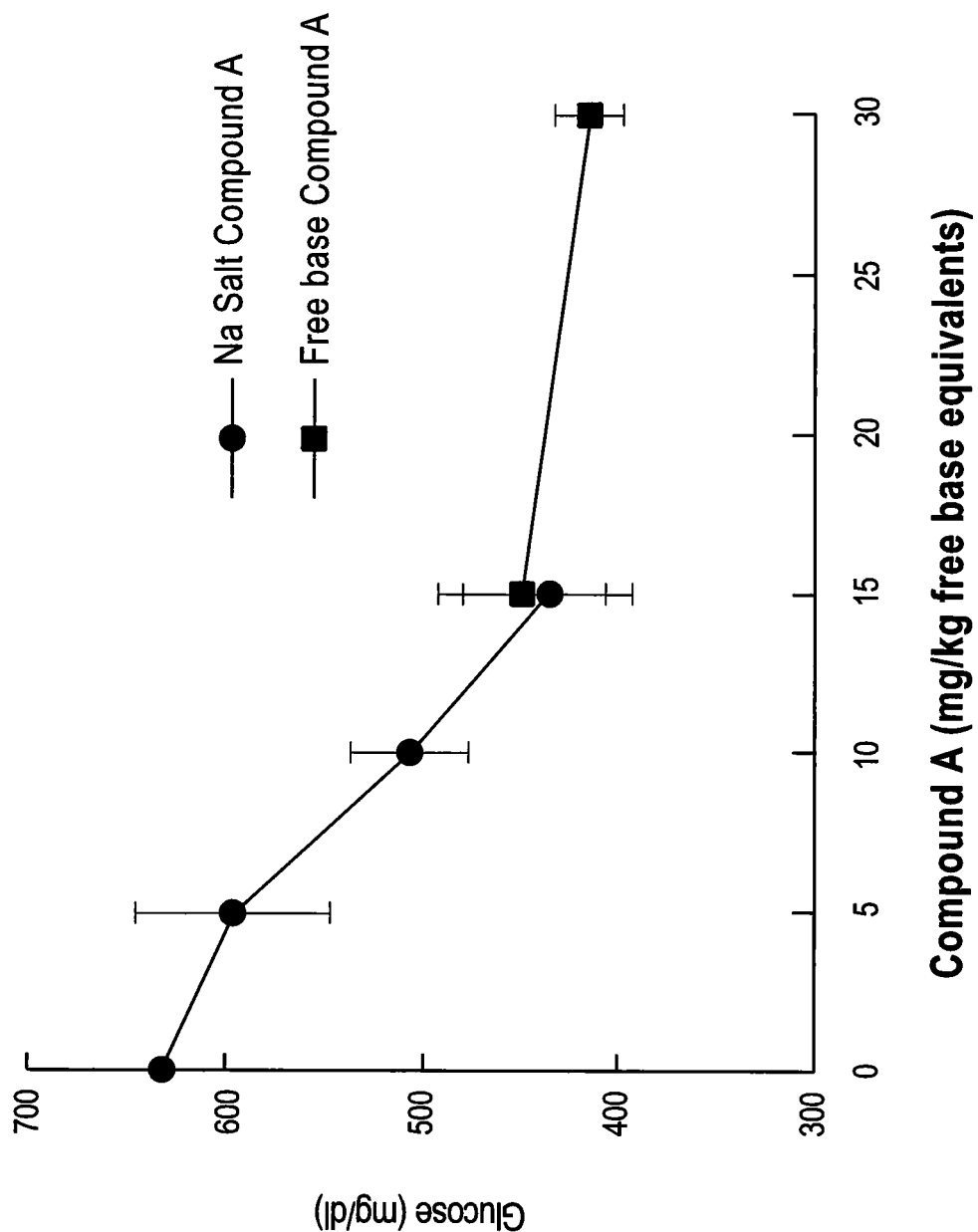
FIG. 11 is a graph of glucose concentration as a function of dosage of Compound A or a sodium salt thereof in a mouse model.
Figure 12:
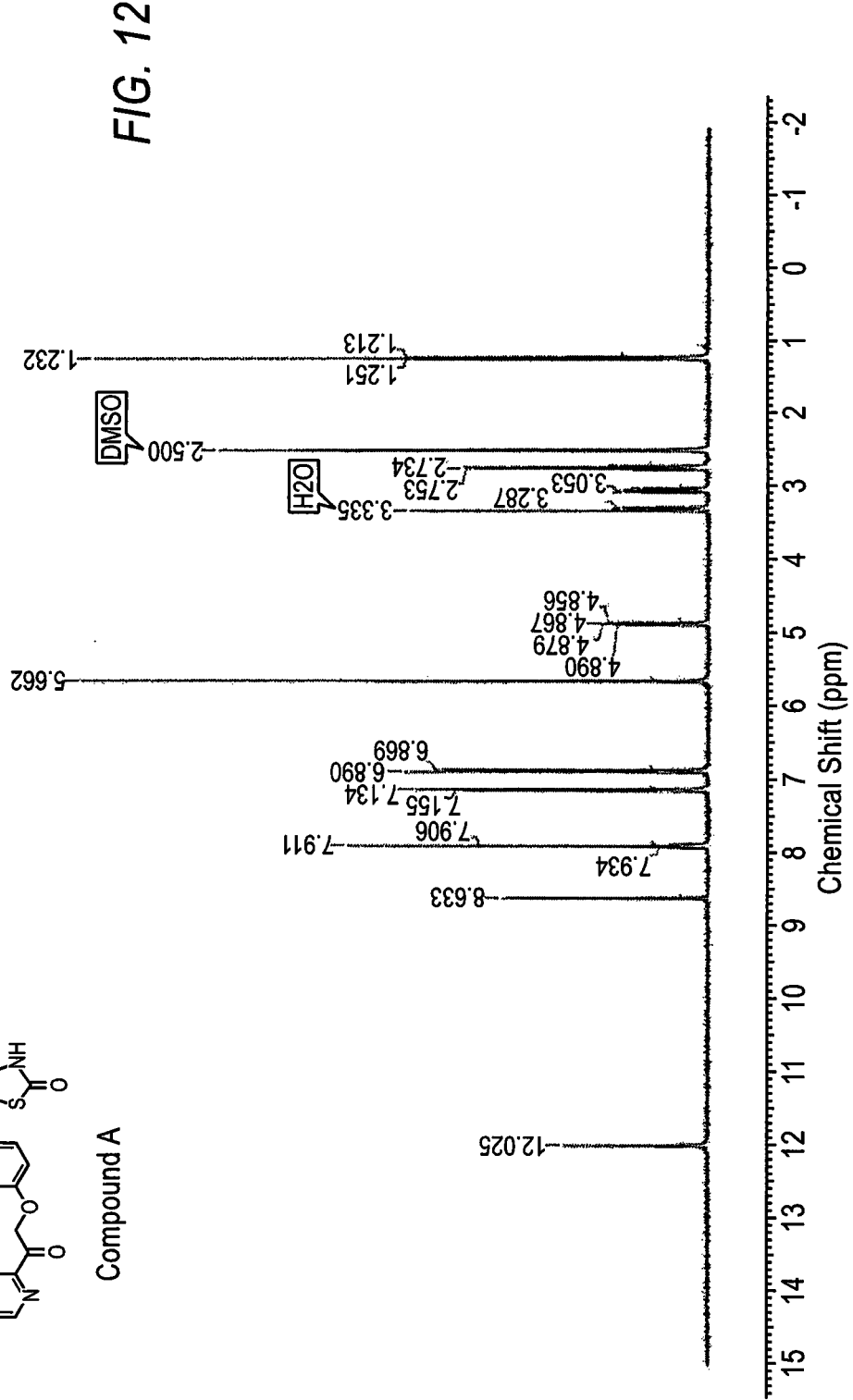
FIG. 12 is a $^1$H NMR spectrum for 5-(4-(2-(5-ethylpyridin-2-yl)-2-oxoethoxy)benzyl)-1,3-thiazolidine-2,4-dione (Compound A)
Figure 13:
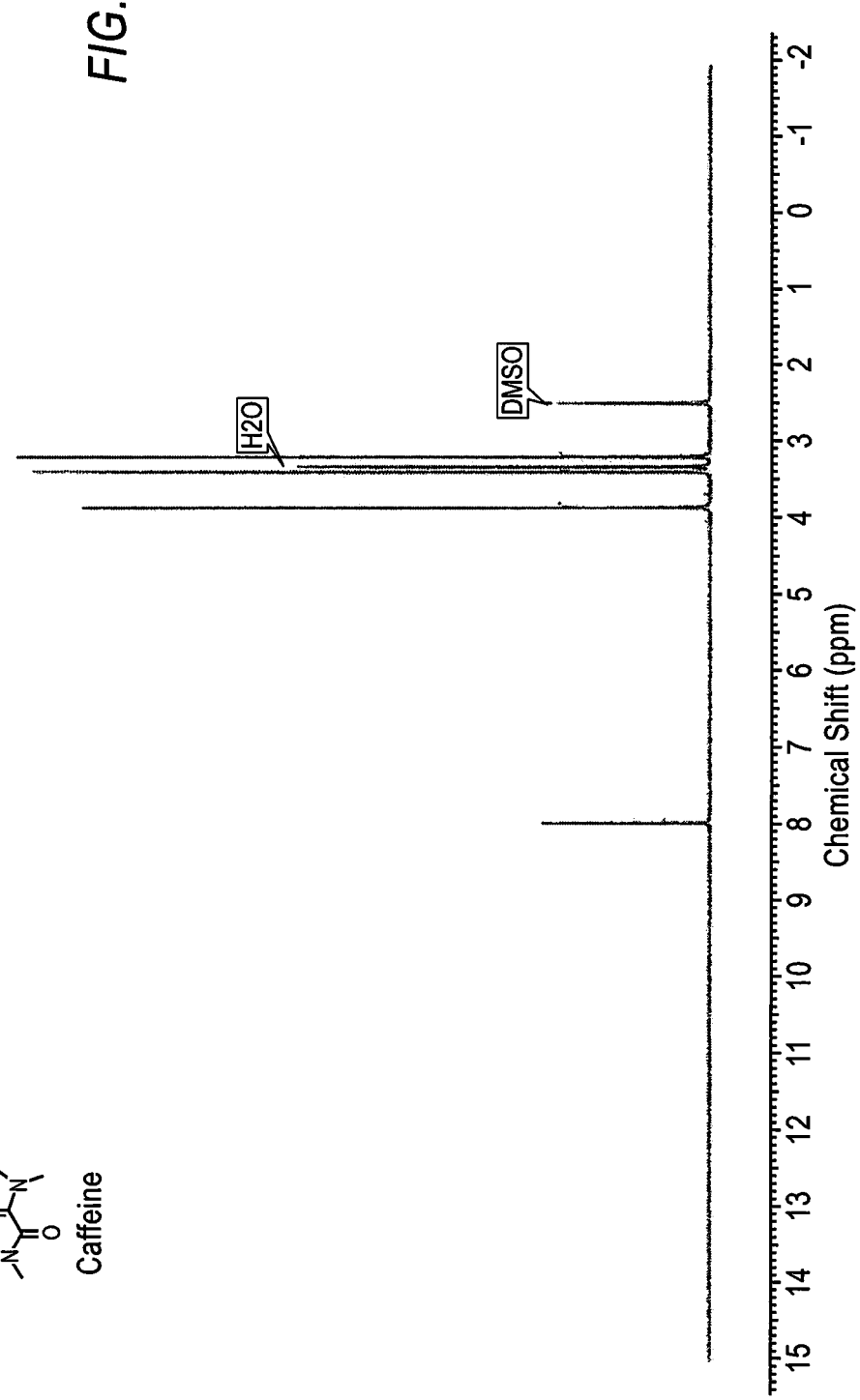
FIG. 13 is a NMR spectrum for caffeine.
Figure 14:
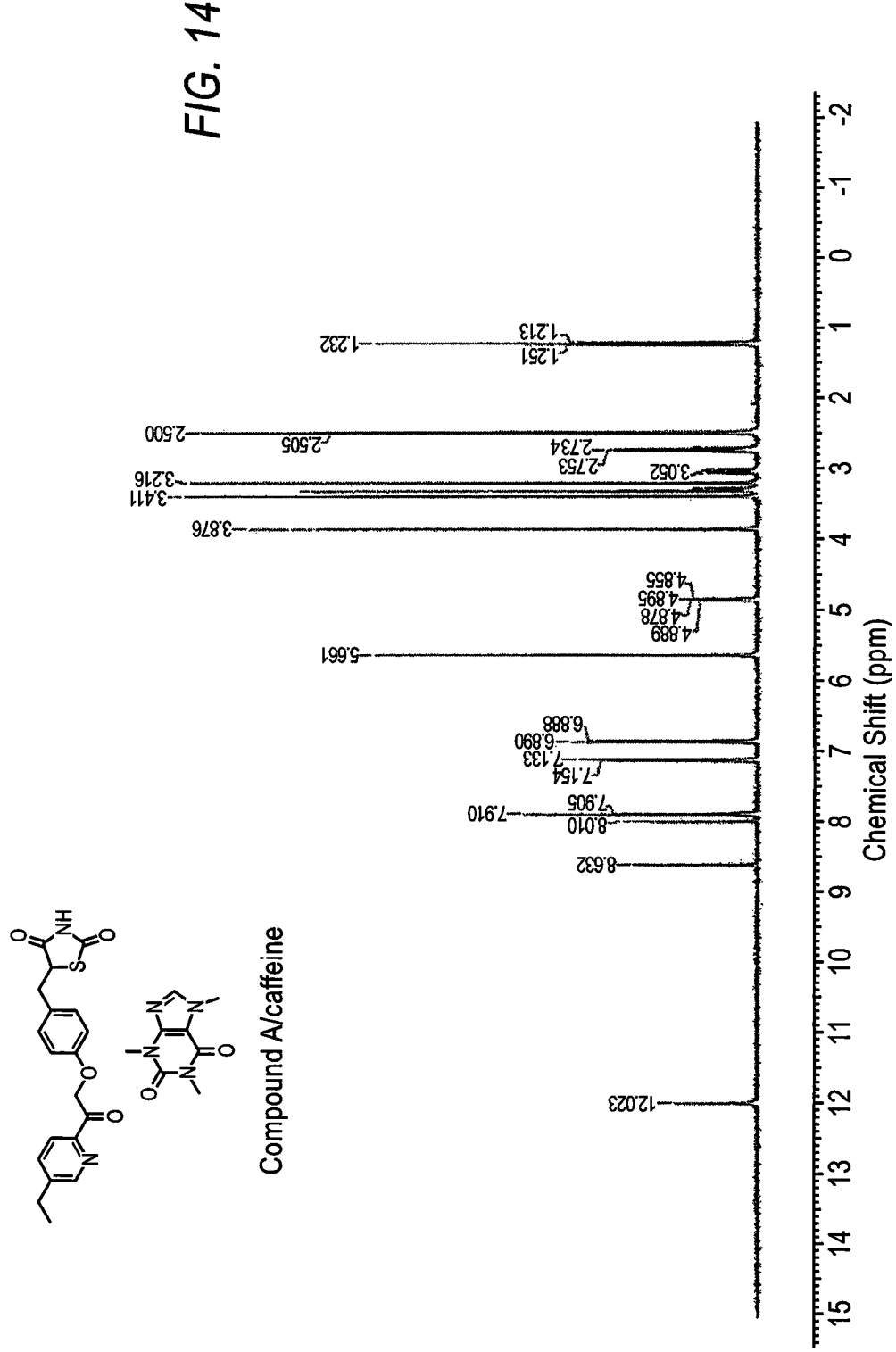
FIG. 14 is a $^1$H NMR spectrum for an exemplary co-crystal of 5-(4-(2-(5-ethylpyridin-2-yl)-2-oxoethoxy)benzyl)-1,3-thiazolidine-2,4-dione and caffeine.

Referring to FIG. 11, the Na salt of Compound A demonstrated an excellent dose response for lowering blood glucose in the diabetic KKAy mouse. In these experiments, free base or sodium salt was given to diabetic KKAy mice (N=6) and blood glucose was measured after 4 days of daily treatment at the doses indicated. KKAy mice, 8-12 weeks of age, were given the doses of the compounds according to the dosages on the X axis of FIG. 11. The compounds were given by gavage once daily at 10 mg/kg. On the fifth day (after 4 daily doses at the levels show) a blood sample was taken to measure plasma glucose.

Example 12A

Exemplary Biological Property of Co-Crystal

The effectiveness of the co-crystals of compound salts is demonstrated in cell systems designed to evaluate their effectiveness in the differentiation of brown adipose tissue (BAT) in a cell culture. Co-crystals formulated with compound salts that show efficacy in the cell systems will also be effective and preventing weight gain in vivo and preserving pancreatic b-cells, the loss of which leads to the development of diabetes.

Example 12B

Preparation of Co-Crystals

Co-Crystal A:
To caffeine (0.194 g, 1 mmol) and 5-(4-(2-(5-ethylpyridin-2-yl)-2-oxoethoxy)benzyl)-1,3-thiazolidine-2,4-dione (0.370 g, 1 mmol) was added acetonitrile (20 mL). The mixture was warmed in a 75° C. oil bath until the solids dissolved. Warming was continued for about 109 minutes, then the solution was filtered and allowed to cool to room temperature. The solvent was allowed to evaporate until crystallization was complete. Co-crystalline solid was isolated by filtration and was dried in vacuo. The melting point of the resulting crystalline material was measure to be from about 123° C. to about 131° C. Note that melting point for pure caffeine is reported to be from about 234° C. to about 236° C., and the melting point for pure 5-(4-(2-(5-ethylpyridin-2-yl)-2-oxoethoxy)benzyl)-1,3-thiazolidine-2,4-dione was measured to be from about 140° C. to about 142° C.

The $^1$H NMR spectra of 5-(4-(2-(5-ethylpyridin-2-yl)-2-oxoethoxy)benzyl)-1,3-thiazolidine-2,4-dione, caffeine, and the co-crystal are provided in FIGS. 15-17. These spectra were obtained using a Bruker 400 mHz NMR spectrometer, wherein the analyte was dissolved in D6-DMSO.

Co-Crystal B:
To caffeine (0.194 g, 1 mmol) and 5-(4-(2-(3-methoxyphenyl)-2-oxoethoxy)benzyl)thiazolidine-2,4-dione having the structure:

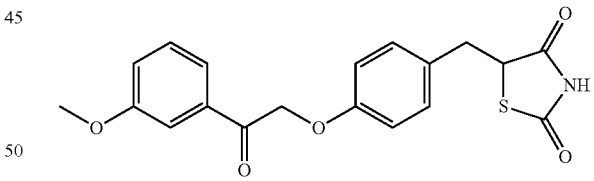

(0.371 g, 1 mmol) is added acetonitrile (20 mL). The mixture is warmed in a 75° C. oil bath until the solids dissolved. Warming continues for about 109 minutes, then the solution is filtered and cooled to room temperature. The solvent is evaporated until crystallization was complete. Co-crystalline solids are isolated by filtration and dried in vacuo.

Example 13

Assays

Assays for Measuring Reduced PPARγ Receptor Activation

Whereas activation of the PPARγ receptor is generally believed to be a selection criteria to select for molecules that may have anti-diabetic and insulin sensitizing pharmacology, this invention finds that activation of this receptor should be a negative selection criterion. Molecules will be chosen from this chemical space because they have reduced, not just selective, activation of PPARγ. The optimal compounds have at least a 10-fold reduced potency as compared to pioglitazone and less than 50% of the full activation produced by rosiglitazone in assays conducted in vitro for transactivation of the PPARγ receptor. The assays are conducted by first evaluation of the direct interactions of the molecules with the ligand binding domain of PPARγ. This can be performed with a commercial interaction kit that measures the direct interaction by florescence using rosiglitazone as a positive control.

PPARγ binding is measured by a TR-FRET competitive binding assay using Invitrogen LanthaScreen™ TR-FRET PPARγ Competitive Binding Assay (Invitrogen #4894). This assay uses a terbium-labeled anti-GST antibody to label the GST tagged human PPARγ ligand binding domain (LBD). A fluorescent small molecule pan-PPAR ligand tracer binds to the LBD causing energy transfer from the antibody to the ligand resulting in a high TR-FRET ratio. Competition binding by PPARγ ligands displace the tracer from the LBD causing a lower FRET signal between the antibody and tracer. The TR-FRET ratio is determined by reading the fluorescence emission at 490 and 520 nm using a Synergy2 plate reader (BioTek). The ability of several exemplary compounds of the present invention to bind to PPARγ was also measured using a commercial binding assay (Invitrogen Corporation, Carlsbad, Calif.) that measures the test compounds ability to bind with PPAR-LBD/Fluormone PPAR Green complex. These assays were performed on three occasions with each assay using four separate wells (quadruplicate) at each concentration of tested compound. The data are mean and SEM of the values obtained from the three experiments. Rosiglitazone was used as the positive control in each experiment. Compounds were added at the concentrations shown, which ranged from 0.1-100 micromolar.

PPARγ activation in intact cells may be measured by a cell reporter assay using Invitrogen GeneBLAzer PPARγ Assay (Invitrogen #1419). This reporter assay uses the human PPARγ ligand binding domain (LBD) fused to the GAL4 DNA binding domain (DBD) stably transfected into HEK 293H cells containing a stably expressed beta-lactamase reporter gene under the control of an upstream activator sequence. When a PPARγ agonist binds to the LBD of the GAL4/PPAR fusion protein, the protein binds to the upstream activator sequence activating the expression of beta-lactamase. Following a 16 hour incubation with the agonists the cells are loaded with a FRET substrate for 2 hours and fluorescence emission FRET ratios are obtained at 460 and 530 nm in a Synergy2 plate reader (BioTek).

In addition to showing the reduced activation of the PPARγ receptor in vitro, the compounds will not produce significant activation of the receptor in animals. Compounds dosed to full effect for insulin sensitizing actions in vivo (see below) will be not increase activation of PPARγ in the liver as measured by the expression of a P2, a biomarker for ectopic adipogenesis in the liver [Matsusue K, Haluzik M, Lambert G, Yim S-H, Oksana Gavrilova O, Ward J M, Brewer B, Reitman M L, Gonzalez F J. (2003) Liver-specific disruption of PPAR in leptin-deficient mice improves fatty liver but aggravates diabetic phenotypes. J. Clin. Invest.; 111: 737] in contrast to pioglitazone and rosiglitazone, which do increase a P2 expression under these conditions.

Mitochondrial Membrane Competitive Binding Crosslinking Assay

A photoaffinity crosslinker was synthesized by coupling a carboxylic acid analog of pioglitazone to a p-azido-benzyl group containing ethylamine as in Amer. J. Physiol 256: E252-E260. The crosslinker was iodinated carrier free using a modification of the Iodogen (Pierce) procedure and purified using open column chromatography (PerkinElmer). Specific crosslinking is defined as labeling that is prevented by the presence of competing drug. Competitive binding assays are conducted in 50 mM Tris, pH8.0. All crosslinking reactions are conducted in triplicate using 8 concentrations of competitor ranging from 0-25 µM. Each crosslinking reaction tube contains 20 µg of crude mitochondrial enriched rat liver membranes, 0.1 µCi of 125I-MSDC-1101, and −/+ competitor drug with a final concentration of 1% DMSO. The binding assay reaction is nutated at room temperature in the dark for 20 minutes and stopped by exposure to 180,000 µJoules. Following crosslinking, the membranes are pelleted at 20,000×g for 5 minutes, the pellet is resuspended in Laemmli sample buffer containing 1% BME and run on 10-20% Tricine gels. Following electrophoresis the gels are dried under vacuum and exposed to Kodak BioMax MS film at −80° C. The density of the resulting specifically labeled autoradiography bands are quantitated using ImageJ software (NIH) and $IC_{50}$ values determined by non-linear analysis using GraphPad Prism™. Selected compounds in this assay demonstrated an $IC_{50}$ of less than 20 µM, less than 5 µM or less than 1 µM. The crosslinking to this protein band is emblematic of the ability of the ability of the PPAR-sparing compounds to bind to the mitochondria, the key organelle responsible for the effectiveness of these compounds for this utility.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A sodium salt of a compound having the structure:

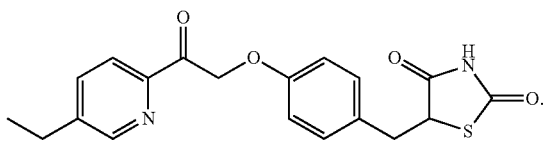 [SMILES: CCc1ccc(C(=O)COc2ccc(CC3SC(=O)NC3=O)cc2)nc1]

* * * * *